US006822141B2

(12) United States Patent
Lardizabal et al.

(10) Patent No.: US 6,822,141 B2
(45) Date of Patent: Nov. 23, 2004

(54) DIACYLGLYCEROL ACYL TRANSFERASE PROTEINS

(75) Inventors: Kathryn Dennis Lardizabal, Woodland, CA (US); Gregory A. Thompson, Clarkston, WA (US); Deborah Hawkins, Davis, CA (US)

(73) Assignee: Calgene LLC, Davis, CA (US)

( * ) Notice: Subject to any disclaimer, the term of this patent is extended or adjusted under 35 U.S.C. 154(b) by 28 days.

(21) Appl. No.: 10/121,857

(22) Filed: Apr. 15, 2002

(65) Prior Publication Data

US 2003/0028923 A1 Feb. 6, 2003

Related U.S. Application Data

(63) Continuation of application No. 09/345,461, filed on Jun. 30, 1999.
(60) Provisional application No. 60/130,829, filed on Apr. 23, 1999, and provisional application No. 60/091,631, filed on Jul. 2, 1998.
(51) Int. Cl.$^7$ .......................... A01H 5/00; C12N 15/31; C12N 15/52; C12N 15/54; C12N 15/82
(52) U.S. Cl. ....................... 800/281; 800/288; 800/298; 536/23.1; 536/23.2; 536/23.6; 536/23.7; 435/419
(58) Field of Search ................................. 800/281, 288, 800/278, 298; 536/23.7, 23.1, 23.2, 23.6

(56) References Cited

FOREIGN PATENT DOCUMENTS

WO     98 55631     12/1998

OTHER PUBLICATIONS

Broun P. et al. Science vol. 282; Nov. 13, 1998, pp. 1315–1317.*
Waterhouse P. et al., Trends in Plant Sciences, Nov. 1999, vol. 4, No. 11, pp. 452–457.*
Boyer et al.: "S.cerevisiae chromosome XV reading frame ORF YOR245c", EMBL Accession NO. SCYOR245c (XP002146447). Abstract, Jul. 9, 1996.
Andersson et al., "Purification of diacylglycerol:acyltransferase from rat liver to near homegeneity", Journal of Lipid Research. U.S., Bethesda, MD., No. 35:535–545 (1994), (XP002079127). Abstract.
Cases, S. et al.: "Identification of a gene encoding an acyl CoA diacyllycerol acyltransferase, a key enzyme in triacylglycerol synthesis", Proceedings of the National Academy of Sciences of USA. US. National Academy of Science, Washington, vol. 95. No. 22:13018–13023 (1998), (XP002122745), Abstract.

Hillier et al.: ". . . Homo sapiens cDNA clone IMAGE:488805 . . . ", EMBI. Accession No. HS84166 (XP002146442). Abstract, Jul. 3, 1995.
Kamisaka et al.: "Purification and Characterization of Diacylglycerol Acyltransferse from the Lipid Body Fraction of An Oleaginous Fungus" Journal of Biochemistry, JP. Japanese Biochemical Society, Tokyo, vol. 6, No. 121:1107–1114, (1997), (XP002079124), Abstract: Table 1.
Kwanyuen et al "Isolation and purification of diacylglycerol acyltransferse from germinating soybean cotyledons", BBA Lipids and Lipid Metabolism, NI Elsevier Science BV. Amsterdam. No. 877:238–245 (1986), (XP002079128).
Little et al.: "Solubilization and characterization of diacylglycerol acyltransferase from microspore–derived cultures of oilseed rape", Biochemical Journal. GB. Portland Press, London, No. 304:951–958 (1994), (XP002079126).
Marra et al.: ". . . Mus musculus cDNA clone IMAGE:1277098 . . . ", EMBL Accession No. AA880955 (XP002146445), Abstract, Mar. 30, 1998.
Marra et al.: ". . . Mus musculus cDNA clones IMAGE:1243243 . . . ", EMBL Accession No. AA822348 (XP002146444), Abstract, Feb. 18, 1998.
Marra et al.: ". . . Mus musculus cDNA clone IMAGE:1276709 . . . ", EMBL Accession No. AA880703 (XP002146443), Iabstract, Mar. 30, 1998.
Newman et al.: ". . . Arabidopsis thaliana cDNA clone 16101T7 . . . ", EMBL Accession No. AT83514 (XP002146441), Abstract, Aug. 11, 1995.
Wilson et al.: "Caenorhabditis elegans cosmid K07B1", EMBL Accession No. CEAF3384 (XP002146446), Abstract, May 16, 1997.

* cited by examiner

Primary Examiner—Phuong T. Bui
Assistant Examiner—Russell Kallis
(74) Attorney, Agent, or Firm—Renessen LLC

(57) ABSTRACT

The invention provides diacylglycerol acyltransferase (DAGAT) proteins, wherein said proteins are active in the formation of triacylglycerol from fatty acyl and diacylglycerol substrates. In one aspect, Mortierella ramanniana DAGAT proteins have been isolated and have molecular weights of between approximately 36 and 37 kDa as measured by SDS-PAGE. The invention also provides novel DAGAT polynucleotide and polypeptide sequences and to methods of producing such polypeptides using recombinant techniques. In addition, methods are provided for using such sequences to alter triacylglycerol levels in plants and to treat diseases associated with altered DAGAT activity or expression.

9 Claims, 16 Drawing Sheets

Figure 13

```
              1                                                           60
MR1           MASKDQHLQQKVKHTLEAIPSPRYAPLR-VPLRRRLQTLAVLLWCSMMSICMFIFFFLCS
MR2           ......MEQVQVTALLDHIPKVHWAPLRGIPLKRRLQTSAIVTWLALLPICLIIYLYLFT 61                                                         120
MR1           IPVLLWFPIILYLTWILVWDKAPENGGRPIRWLRNAAWWKLFAGYFPAHVIKEADLDPSK
MR2           IP-LLWPILIMYTIW-LFFDKAPENGGRRISLVRKLPLWKHFANYFPVTLIKEGDLDPKG 121                                                        180
MR1           NYIFGYHPHGIISMGSFCTFSTNATGFDDLFPGIRPSLLTLTSNFNIPLYRDYLMACGLC
MR2           NYIMSYHPHGIISMAAFANFATEATGFSEQYPGIVPSLLTLASNFRLPLYRDFMMSLGMC 181                                                        240
MR1           SVSKTSCQNILTKGGPGRSIATVVGGASESLNARPGVMDLVLKRRFGFIKIAVQTGASLV
MR2           SVSRHSCEAIL-RSGPGRSIVIVTGGASESLSARPGTNDLTLKKRLGFIRLAIRNGASLV 241                                                        300
MR1           PTISFGENELYEQIESNENSKLHRWQKKIQHALGFTMPLFHGRGVFNYDFGLLPHRHPIY
MR2           PIFSFGENDIYEQYDNKKGSLIWRYQKWFQKITGFTVPLAHARGIFNYNAG.........

301                                              357
MR1           TIVGKPIPVPSIKYGQTKDEIIRELHDSYMHAVQDLYDRYKDIYAKDRVKELEFVE.
MR2           ........................................................
```

DIACYLGLYCEROL ACYL TRANSFERASE PROTEINS

CROSS-REFERENCE TO RELATED APPLICATIONS

This application is a continuation of co-pending U.S. application Ser. No. 09/345,461, filed Jun. 30, 1999, which claims the benefit of U.S. Provisional Application No. 60/091,631, filed Jul. 2, 1998, and U.S. Provisional Application No. 60/130,829, filed Apr. 23, 1999, all of which are herein incorporated by reference in their entireties.

INCORPORATION OF SEQUENCE LISTING

A paper copy of the Sequence Listing and a computer readable form (CRF) of the sequence listing on diskette, containing the file named "seqlisting 16515-143.txt", which is 51.344 bytes in size (measured in MS-DOS), and which was recorded on Apr. 15, 2002, are herein incorporated by reference.

TECHNICAL FIELD

The present invention is directed to enzymes, methods to purify, and obtain such enzymes, amino acid and nucleic acid sequences related thereto, and methods of use for such compositions in genetic engineering applications.

BACKGROUND OF THE INVENTION

Triacylglycerol (TAG) is thought to be the most important storage of energy for cells. Diacylglycerol acyl transferase is an enzyme which is believed to regulate TAG structure and direct TAG synthesis. The reaction catalyzed by DAGAT is at a critical branchpoint in glycerolipid biosynthesis. Enzymes at such branchpoints are considered prime candidates for sites of metabolic regulation. There are several enzymes which are common to the synthesis of diacylglycerol, TAG and membrane lipids, however, the DAGAT reaction is specific for oil synthesis.

In plants, TAG is the primary component of vegetable oil that is used by the seed as a stored form of energy to be used during seed germination. Higher plants appear to synthesize oils via a common metabolic pathway. Fatty acids are made in plastids from acetyl-CoA through a series of reactions catalyzed by enzymes known collectively as Fatty AcidSynthetase (FAS). The fatty acids produced in plastids are exported to the cytosolic compartment of the cell, and are esterified to coenzyme A. These acyl-CoAs are the substrates for glycerolipid synthesis in the endoplasmic reticulum (ER). Glycerolipid synthesis itself is a series of reactions leading first to phosphatidic acid (PA) and diacylglycerol (DAG). Either of these metabolic intermediates may be directed to membrane phospholipids such as phosphatidylglycerol (PG), phosphatidylethanolamine (PE) or phosphatidylcholine (PC), or they may be directed on to form neutral triacylglycerol (TAG).

Diacylglycerol (DAG) is synthesized from glycerol-3-phosphate and fatty acyl-CoAs in two steps catalyzed sequentially by glycerol-3-phosphate acyltransferase (G3PAT), and lysophosphatidic acid acyltransferase (LPAAT) to make PA, and then an additional hydrolytic step catalyzed by phosphatidic acid phosphatase (PAP) to make DAG. In most cells, DAG is used to make membrane phospholipids, the first step being the synthesis of PC catalyzed by CTP-phosphocholine cytidylyltransferase. In cells producing storage oils, DAG is acylated with a third fatty acid in a reaction catalyzed by diacylglycerol acyltransferase (DAGAT). Collectively, the reactions make up part of what is commonly referred to as the Kennedy Pathway.

The structure of the TAG, as far as positional specificity of fatty acids, is determined by the specificity of each of the three acyltransferases for the fatty acyl-CoA and the glycerol backbone substrates. Thus, for example, there is a tendency for the acyltransferases from many temperate zone species of seeds to allow either a saturated or an unsaturated fatty acid at the sn-1 or the sn-3 position, but only an unsaturated fatty acid at the sn-2. The absolute specificity for an unsaturated fatty acid at sn-2 is determined by the substrate preference of LPAAT enzyme. In some species such as cocoa, TAG compositions suggest that this tendency is carried further in that there is an apparent preference for acylation of the sn-3 position with a saturated fatty acid, if the sn-1 position is esterified to a saturated fatty acid. Thus, there is a higher percentage of structured TAG of the form SUS (where S=saturated fatty acid and U=unsaturated fatty acid), than would be expected from a random distribution based on the overall fatty acid composition with the sn-2 position fixed with an unsaturated fatty acid. This suggests that DAGAT also plays an important role in the regulation of TAG structure, if not also in the control of TAG synthesis.

Obtaining nucleic acid sequences capable of producing a phenotypic result in the incorporation of fatty acids into a glycerol backbone to produce an oil is subject to various obstacles including but not limited to the identification of metabolic factors of interest, choice and characterization of a protein source with useful kinetic properties, purification of the protein of interest to a level which will allow for its amino acid sequencing, utilizing amino acid sequence data to obtain a nucleic acid sequence capable of use as a probe to retrieve the desired DNA sequence, and the preparation of constructs, transformation and analysis of the resulting plants.

Thus, the identification of enzyme targets and useful tissue sources for nucleic acid sequences of such enzyme targets capable of modifying oil structure and quantity are needed. Ideally an enzyme target will be amenable to one or more applications alone or in combination with other nucleic acid sequences relating to increased/decreased oil production, TAG structure, the ratio of saturated to unsaturated fatty acids in the fatty acid pool, and/or to other novel oils compositions as a result of the modifications to the fatty acid pool.

For example, in some instances having an oilseed with a higher ratio of oil to seed meal would be useful to obtain a desired oil at lower cost. This would be typical of a high value oil product. Or such an oilseed might constitute a superior feed for animals. In some instances having an oilseed with a lower ratio of oil to seed meal would be useful to lower caloric content. In other uses, edible plant oils with a higher percentage of unsaturated fatty acids are desired for cardiovascular health reasons. And alternatively, temperate substitutes for high saturate tropical oils such as palm, coconut, or cocoa would also find uses in a variety of industrial and food applications.

In mammals, DAGAT plays an important role in the metabolism of cellular diacylglycerol and is important in processes involving triacylglycerol metabolism including intestinal fat absorption, lipoprotein assembly, adipose tissue formation and lactation. As such, identification and isolation of the DAGAT protein and of polynucleotide and polypeptide sequences is desired.

Several putative isolation procedures have been published for DAGAT. Polokoff and Bell (1980) reported solubilization and partial purification of DAGAT from rat liver microsomes. This preparation was insufficiently pure to identify a specific protein factor responsible for the activity. Kwanyuen and Wilson (1986, 1990) reported purification and characterization of the enzyme from soybean cotyledons. However, the molecular mass (1843 kDa) suggests that this preparation was not extensively solubilized and any DAGAT protein contained therein was part of a large aggregate of many proteins. Little et al (1993) reported solubilization of DAGAT from microspore-derived embryos from rapeseed, but as with Kwanyuen and Wilson, the molecular mass of the material that was associated with activity was so high, that complete solubilization is unlikely. Andersson et al (1994) reported solubilization and a 415-fold purification of DAGAT from rat liver using immunoaffinity chromatography. However, there is no evidence that the antibodies they used recognize DAGAT epitopes, nor that the protein that they purified is truly DAGAT. Indeed, as with Kwanyuen and Wilson, the DAGAT activity in their preparations exhibited a molecular mass typical of aggregated membrane proteins. Finally, Kamisaka et al (1993, 1994, 1996, 1997) report solubilization of DAGAT from *Mortierella rammaniana* and subsequent purification to homogeneity. They suggest that DAGAT solubilized from this fungal species has an apparent molecular mass of 53 kDa by SDS-PAGE. However, as shown in Example 4 below, fractions obtained using the protocol described by Kamisaka et al. did not provide abundant 53-kDa polypeptide which correlated with DAGAT activity.

SUMMARY OF THE INVENTION

The present invention is directed to diacyglycerol acyl transferase (DAGAT), and in particular to DAGAT polypeptides and polynucleotides. The polypeptides and polynucleotides of the present invention include those derived from plant, mammalian, including human, nematode and fungal sources.

In another aspect, the invention provides DAGAT proteins having molecular weights between approximately 36 kDa and 37 kDa, based on SDS-PAGE analysis, and particularly molecular weights of 36 kDa and 36.5 kDa. The preferred DAGAT proteins of the invention are obtainable from *Mortierella ramanniana*.

In a further aspect the invention relates to oligonucleotides derived from the DAGAT proteins and oligonucleotides which include partial or complete DAGAT encoding sequences.

It is also an aspect of the present invention to provide recombinant DNA constructs which can be used for transcription or transcription and translation (expression) of DAGAT. In particular, constructs are provided which are capable of transcription or transcription and translation in plant and mammalian host cells. Particularly preferred constructs are those capable of transcription or transcription and translation in plant cells.

In another aspect of the present invention, methods are provided for production of DAGAT in a host cell or progeny thereof. In particular, host cells are transformed or transfected with a DNA construct which can be used for transcription or transcription and translation of DAGAT. The recombinant cells which contain DAGAT are also part of the present invention.

In a further aspect, the present invention relates to methods of using polynucleotide and polypeptide sequences to modify the ratios of oils to other constituents, as well as to modify the composition and/or structure of triglyceride molecules, particularly in seed oil of oilseed crops. Plant cells having such a modified triglyceride are also contemplated herein.

The modified plants, seeds and oils obtained by the expression of the plant DAGAT proteins are also considered part of the invention.

In a further aspect, the invention relates to methods for using such polypeptides and polynucleotides in mammals are provided. Such methods include treating or ameliorating diseases associated with DAGAT activity, including diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis. In addition, methods are provided for altering the levels of DAGAT activity.

In another aspect of the present invention, methods for identifying agonists and antagonists/inhibitors of DAGAT, and treating conditions associated with DAGAT activity or altering levels of DAGAT activity with such agonists or antagonists are provided.

It is also an aspect of the present invention to provide diagnostic assays for detecting alterations in the level of DAGAT activity and for diagnosing conditions associated with DAGAT activity.

BRIEF DESCRIPTION OF THE DRAWINGS

FIG. 6 presents results of analysis of *Mortierella ramanniana* DAGAT activity in column fractions from a DAGAT purification protocol.

FIG. 13 shows the protein alignments of the two DAGAT proteins identified in *Mortierella ramanniana*. Full-length protein sequence of the 36 kDa candidate is shown while partial sequence of the 36.5 kDa protein is shown.

DETAILED DESCRIPTION OF THE INVENTION

Figure 1:
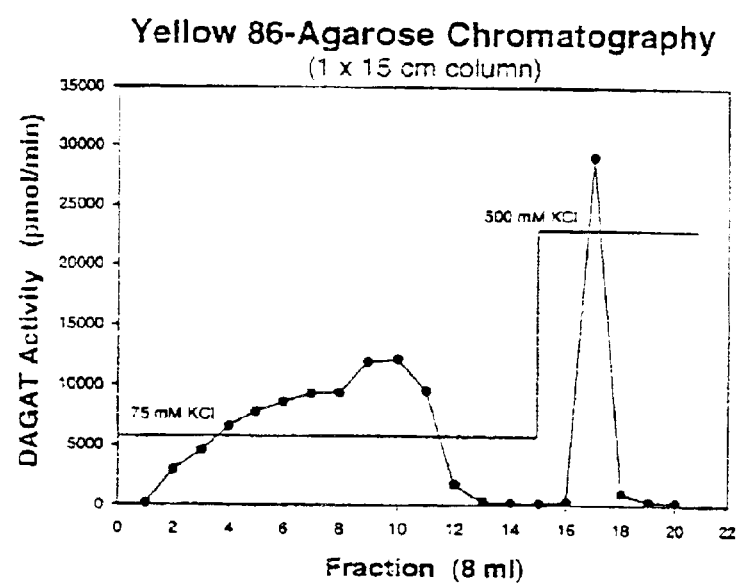
FIG. 1 shows the results of chromatography of *Mortierella ramanniana* DAGAT activity on a Yellow 86-Agarose column.

The present invention relates to diacylglycerol acyltransferase (referred to herein as DAGAT), particularly the isolated DAGAT protein and nucleic acid sequences encoding the DAGAT protein. A diacylglycerol acyltransferase of this invention includes any nucleic acid sequence encoding amino acids, such as a protein, polypeptide or peptide, obtainable from a cell source, which demonstrates the ability to catalyze the production of triacylglycerol from 1,2-diacylglycerol and fatty acyl substrates under enzyme reactive conditions. By "enzyme reactive conditions" is meant that any necessary conditions are available in an environment (i.e., such factors as temperature, pH, lack of inhibiting substances) which will permit the enzyme to function.

Isolated Proteins, Polypeptides and Polynucleotides

A first aspect of the present invention relates to isolated DAGAT proteins. As used herein, "isolated" means altered "by the hand of man" from its natural state. For example, if it occurs in nature, it has been changed or removed from its original environment, or both. For example, a polynucleotide or a polypeptide naturally present in a living organism is not "isolated," but the same polynucleotide or polypeptide when separated from the materials of its natural state is "isolated". In particular, DAGAT proteins were identified which have a molecular weight between approximately 36 kDa and approximately 37 kDa, according to SDS-PAGE analysis. In particular, DAGAT proteins are provided which have molecular weights of approximately 36 kDa and 36.5 kDa and are obtainable from *Mortierella ramanniana*. Further, the DAGAT proteins have been solubilized. "Solubilization" refers to extraction of the DAGAT enzyme from the membranes in such a way that it then behaves in a manner typical of enzymes that are not membrane-associated.

The DAGAT protein of the subject invention may utilize a variety of acyl substrates in a host cell, including fatty acyl-CoA and fatty acyl-ACP molecules. In addition, the acyl substrates acted upon by the DAGAT may have varying carbon chain lengths and degrees of saturation, although the DAGAT may demonstrate preferential activity towards certain molecules.

Another aspect of the present invention relates to DAGAT polypeptides. Such polypeptides include isolated polypeptides set forth in the Sequence Listing, as well as polypeptides and fragments thereof, particularly those polypeptides which exhibit DAGAT activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403–410 (1990)). The well known Smith Waterman algorithm can also be used to determine identity.

Parameters for polypeptide sequence comparison typically include the following:

Algorithm: Needleman and Wunsch, *J. Mol. Biol.* 48:443453 (1970)

Comparison matrix: BLOSSUM62 from Hentikoff and Hentikoff, *Proc. Natl. Acad. Sci USA* 89:10915–10919 (1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, J. Mol. Biol. 48:443–453 (1970)

Comparison matrix: matches=+10; mismatches=0

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

$$X\text{-}(R_1)_n\text{-}(R_2)\text{-}(R_3)_n\text{-}Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing and preferably SEQ ID NOs: 38 and 45. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising a sequence selected from the group of a sequence contained in SEQ ID NOs: 37, 44 and 46–72.

Polypeptides of the present invention have been shown to have DAGAT activity and are of interest because DAGAT is involved in the metabolism of cellular glycerolipids, and particularly catalyzes the formation of triacylglycerol from sn-1,2-diacylglycerol and fatty acyl-CoAs. DAGAT is the only enzyme unique to the triacylglycerol biosynthetic pathway (Coleman R. A. (1992) *Methods Enzymol* 209:98–104).

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

Another aspect of the present invention relates to isolated DAGAT polynucleotides. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro- protein sequence. The polynucleotide can also include non-coding sequences, including for example, but not limited to, non-coding 5' and 3 sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

$$X\text{-}(R_1)_n\text{-}(R_2)\text{-}(R_3)_n\text{-}Y$$

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably SEQ ID NOs: 37, 44 and 46–72. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook, et al., Molecular Cloning: A Laboratory Manual, Second Edition, cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to identify members of the library which hybridize to the probe. For example, synthetic oligonucleotides are prepared which correspond to the DAGAT peptide sequences. The oligonucleotides are used as primers in polymerase chain reaction (PCR) techniques to obtain partial DNA sequence of DAGAT genes. The partial sequences so obtained are then used as probes to obtain DAGAT clones from a gene library prepared from *Mortierella ramanniana* tissue. Alternatively, where oligonucleotides of low degeneracy can be prepared from particular DAGAT peptides, such probes may be used directly to screen gene libraries for DAGAT gene sequences. In particular, screening of cDNA libraries in phage vectors is useful in such methods due to lower levels of background hybridization.

Typically, a DAGAT sequence obtainable from the use of nucleic acid probes will show 60–70% sequence identity between the target DAGAT sequence and the encoding sequence used as a probe. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80% sequence homology) from the sequences used as probe. Oligonucleotide probes can be considerably shorter than the entire nucleic acid sequence encoding an DAGAT enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related DAGAT genes. Shorter probes are often particularly useful for polymerase chain reactions (PCR), especially when highly conserved sequences can be identified. (See, Gould, et al., *PNAS USA* (1989) 86:1934–1938.).

The polynucleotides and polypeptides of the invention can be used, for example, in the transformation of plants, as research reagents, and for the discovery of treatments of and diagnostics for disease, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called proproteins.

Plant Constructs and Methods of Use

Of particular interest is the use of the nucleotide sequences in recombinant DNA constructs to direct the transcription or transcription and translation (expression) of the acyltransferase sequences of the present invention in a host plant cell. The expression constructs generally comprise a promoter functional in a host plant cell operably linked to a nucleic acid sequence encoding a diacylglycerol acyltransferase of the present invention and a transcriptional termination region functional in a host plant cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810–812; Rogers, U.S. Pat. No. 5,378,619). In addition, it may also be preferred to bring about expression of the acyltransferase gene in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean α' subunit of β-conglycinin (soy 7s, (Chen et al., *Proc. Natl. Acad. Sci.*, 83:8560–8564 (1986))) and oleosin.

It may be advantageous to direct the localization of proteins conferring DAGAT to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression. the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9:104–126; Clark et al. (1989) *J. Biol. Chem.* 264: 17544–17550: della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481.

Depending upon the intended use, the constructs may contain the nucleic acid sequence which encodes the entire DAGAT protein, or a portion thereof. For example, where antisense inhibition of a given DAGAT protein is desired, the entire DAGAT sequence is not required. Furthermore, where DAGAT sequences used in constructs are intended for use as probes, it may be advantageous to prepare constructs containing only a particular portion of a DAGAT encoding sequence, for example a sequence which is discovered to encode a highly conserved DAGAT region.

The skilled artisan will recognize that there are various methods for the inhibition of expression of endogenous sequences in a host cell. Such methods include, but are not limited to antisense suppression (Smith, et al. (1988) *Nature* 334:724–726) , co-suppression (Napoli, et al. (1989) *Plant Cell* 2:279–289), ribozymes (PCT Publication WO 97/10328), and combinations of sense and antisense Waterhouse, et al. (1998) *Proc. Natl. Acad. Sci. USA* 95:13959–13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the diacylglycerol acyltransferase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the DAGAT sequences directly from the host plant cell plastid. Such constructs and methods are known in the art and are generally described, for example, in Svab, et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a DAGAT nucleic acid sequence.

Plant expression or transcription constructs having a plant DAGAT as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of plant DAGAT constructs in plants which have been genetically engineered to produce a particular fatty acid in the plant seed oil, where TAG in the seeds of nonengineered plants of the engineered species, do not naturally contain that particular fatty acid. Thus, the expression of novel DAGAT in plants may be desirable for the incorporation of unique fatty acyl groups into the sn-3 position.

Further plant genetic engineering applications for DAGAT proteins of this invention include their use in preparation of structured plant lipids which contain TAG molecules having desirable fatty acyl groups incorporated into particular positions on the TAG molecules.

It is contemplated that the gene sequences may be synthesized, either completely or in part, especially where it is desirable to provide plant-preferred sequences. Thus, all or a portion of the desired structural gene (that portion of the gene which encodes the DAGAT protein) may be synthesized using codons preferred by a selected host. Host-preferred codons may be determined, for example, from the codons used most frequently in the proteins expressed in a desired host species.

One skilled in the art will readily recognize that antibody preparations, nucleic acid probes (DNA and RNA) and the like may be prepared and used to screen and recover "homologous" or "related" DAGATs from a variety of plant sources. Homologous sequences are found when there is an identity of sequence, which may be determined upon comparison of sequence information, nucleic acid or amino acid, or through hybridization reactions between a known DAGAT and a candidate source. Conservative changes, such as Glu/Asp, Val/Ile, Ser/Thr, Arg/Lys and Gln/Asn may also be considered in determining sequence homology. Amino acid sequences are considered homologous by as little as 25% sequence identity between the two complete mature proteins. (See generally, Doolittle, R. F., *OF URFS and ORFS* (University Science Books, California, 1986.)

Thus, other DAGATs may be obtained from the specific exemplified Mortierella protein preparations and sequences provided herein. Furthermore, it will be apparent that one can obtain natural and synthetic DAGATs, including modified amino acid sequences and starting materials for synthetic-protein modeling from the exemplified DAGATs and from DAGATs which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

For immunological screening, antibodies to the DAGAT protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the *Mortierella ramanniana* DAGAT.

When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.).

Many plants utilize DAGAT proteins in production of storage TAG in seeds, and thus any such plant species can be considered as a source of additional DAGAT proteins. Plants having high amounts of TAG with palmitate or stearate acyl groups at the sn-1 and sn-3 positions with oleate or linoleate at sn-2 are preferred candidates to obtain plant DAGATs capable of incorporating saturated fatty acids at the sn-3 position of TAG which show special selectivity for synthesis of structured TAG of the form S-U-S, where S represents a saturated fatty acid and U represents an unsaturated fatty acid. For example, oils from several tropical plants including cocoa, illipe, sal, shea, and Garcinia species such as kokum have been shown to accumulate high amounts of TAG in this form.

Plants having significant medium-chain fatty acids in their seed oils are preferred candidates to obtain plant DAGATs capable of incorporating medium-chain fatty acids into the sn-3 position of TAG. Several species in the genus Cuphea accumulate triglycerides containing medium-chain fatty acids in their seeds, e.g., *procumbens, lutea, hookeriana, hyssopifolia, wrightii* and *inflata*. Another natural plant source of medium-chain fatty acids are seeds of the Lauraceae family. In addition to the exemplified California Bay (*Umbellularia californica*), Pisa (*Actinodophne hookeri*), Sweet Bay (*Laurus nobilis*) and *Cinnamomum camphora* (camphor) accumulate medium-chain fatty acids. Other plant sources include *Ulmaceae* (elm), *Palmae, Myristicaceae, Simarubaceae, Vochysiaceae,* and *Salvadoraceae*.

Also of particular interest are DAGATs from plant species which incorporate unusual long-chain fatty acids in the storage TAG. For example nasturtium and meadowfoam contain 22:1 acyl groups in the seed.

It should also be noted that plant DAGATs from a variety of sources can be used to investigate TAG biosynthesis events of plant lipid biosynthesis in a wide variety of in vivo applications. Because all plants appear to synthesize lipids via a common metabolic pathway, the study and/or application of one plant DAGAT to a heterologous plant host may be readily achieved in a variety of species. In other applications, a plant DAGAT can be used outside the native plant source of the DAGAT to enhance the production and/or modify the composition of the TAG produced or synthesized in vitro.

In addition to isolation of other DAGATs, it is considered that genes for other related acyltransferase proteins may also be obtained using sequence information from the DAGAT and related nucleic acid sequences. For example, other acyltransferase enzymes are involved in plant lipid biosynthesis, including plastidial DAGAT, mitochondrial DAGAT, lysophosphatidylcholine acyltransferase (LPCAT), lysophosphatidylserine acyltransferase (LPSAT), lysophosphatidylethanolamine acyltransferase (LPEAT) phosphatidylcholine diacylglyercol acyltransferase (PDAT), and lysophosphatidylinositol acyltransferase (LPIAT). While many of these enzymes catalyze acyltransferase reactions involving the sn-2 position of lysophospholipids, the genes encoding these sequences may also be related to the plant acyl-CoA DAGAT sequences of the instant invention and obtainable therefrom.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, such as Northern or Southern blots, or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266–285). A useful probe and appropriate hybridization and washing conditions having been identified as described above, cDNA or genomic libraries are screened using the labeled sequences and optimized conditions.

The nucleic acid sequences associated with plant DAGAT proteins will find many uses. For example, recombinant constructs can be prepared which can be used as probes, or which will provide for expression of the DAGAT protein in host cells to produce a ready source of the enzyme and/or to modify the composition of triglycerides found therein. Other useful applications may be found when the host cell is a plant host cell, either in vitro or in vivo. For example, by increasing the amount of a respective medium-chain preferring DAGAT available to the plant TAG biosynthesis pathway, an increased percentage of medium-chain fatty acids may be obtained in the TAG. In a like manner, for some applications it may be desired to decrease the amount of DAGAT endogenously expressed in a plant cell by anti-sense technology. For example. to allow for more opportunity for an inserted foreign DAGAT to transfer saturated acyl groups, or medium-chain or unusual longer-chain fatty acyl groups to sn-3 position, decreased expression of a native Brassica long-chain preferring DAGAT may be desired.

As discussed above, nucleic acid sequence encoding a plant DAGAT of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

Once the desired plant DAGAT nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant DAGAT of this invention may be combined with other non-native, or "heterologous", sequences in a variety of ways. By "heterologous" sequences is meant any sequence which is not naturally found joined to the plant DAGAT, including, for example, combinations of nucleic acid sequences from the same plant which are not naturally found joined together.

The DNA sequence encoding a plant DAGAT of this invention may be employed in conjunction with all or part of the gene sequences normally associated with the DAGAT. In its component parts, a DNA sequence encoding DAGAT is combined in a DNA construct having, in the 5' to 3' direction of transcription, a transcription initiation control region capable of promoting transcription and translation in a host cell, the DNA sequence encoding plant DAGAT and a transcription and translation termination region.

Potential host cells include both prokaryotic and eukaryotic cells. A host cell may be unicellular or found in a multicellular differentiated or undifferentiated organism depending upon the intended use. Cells of this invention may be distinguished by having a plant DAGAT foreign to the wild-type cell present therein, for example, by having a recombinant nucleic acid construct encoding a plant DAGAT therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Saccharomyces cerevisiae*, including genes such as beta-galactosidase, T7 polymerase, tryptophan E and the like.

The methods used for the transformation of the host plant cell are not critical to the present invention. The transformation of the plant is preferably permanent, i.e. by integration of the introduced expression constructs into the host plant genome, so that the introduced constructs are passed onto successive plant generations. The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to calcium-phosphate-DNA co-precipitation, electroporation, microinjection, Agrobacterium infection, liposomes or microprojectile transformation. The skilled artisan can refer to the literature for details and select suitable techniques for use in the methods of the present invention.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming host plant cells, the expression or transcription construct bordered by the T-DNA border region (s) will be inserted into a broad host range vector capable of replication in E. coli and Agrobacterium, there being broad host range vectors described in the literature. Commonly used is pRK2 or derivatives thereof. See, for example, Ditta, et al., (Proc. Nat. Acad. Sci., U.S.A. (1980) 77:7347–7351) and EPA 0 120 515, which are incorporated herein by reference. Alternatively, one may insert the sequences to be expressed in plant cells into a vector containing separate replication sequences, one of which stabilizes the vector in E. coli, and the other in Agrobacterium. See, for example, McBride and Summerfelt (Plant Mol. Biol. (1990) 14:269–276), wherein the pRiHRI (Jouanin, et al., Mol. Gen. Genet. (1985) 201:370–374) origin of replication is utilized and provides for added stability of the plant expression vectors in host Agrobacterium cells.

Included with the expression construct and the T-DNA will be one or more markers, which allow for selection of transformed Agrobacterium and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a DNA sequence encoding the diacylglycerol acyltransferase of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the DAGAT expression construct, or alternatively, transformed plants, one expressing the DAGAT construct and one expressing the second construct, can be crossed to bring the constructs together in the same plant.

Other Constructs and Methods of Use

The invention also relates to vectors that include a polynucleotide or polynucleotides of the invention, host cells that are genetically engineered with vectors of the invention and the production of polypeptides of the invention by recombinant techniques. Cell free translation systems can be employed to produce such protein using RNAs derived from the DNA constructs of the invention.

For recombinant production, host cells can be genetically engineered to incorporate expression systems or portions thereof or polynucleotides of the present invention. Introduction of a polynucleotide into a host cell can be effected by methods described in many standard laboratory manuals, such as Davis et al., Basic Methods in Molecular Biology, (1986) and Sambrook et al, Molecular Cloning: A Laboratory Manual, $2^{nd}$ Edition, Cold Spring Harbor Laboratory Press, Cold Spring Harbor N.Y. (1989). Such methods include, but are not limited to, calcium phosphate transfection, DEAE dextran mediated transfection, transvection, microinjection, cationic lipid-mediated transfection, electroporation, transduction, scrape loading ballistic introduction and infection.

Representative examples of appropriate hosts include bacterial cells, such as streptococci, staphylococci, enterococci, E. coli, streptomyces, and Bacillus subtilis cells; fungal cells, such as yeast cells and Aspergillus cells; insect cells, such as Drosophila S2 and Spodoptera Sf9 cells; animal cells such as CHO, COS, HeLa, C127, 3T3, BHK, 293 and Bowes melanoma cells; and plant cells as described above.

A variety of expression systems can be used to produce the polypeptides of the invention. Such vectors include, but are not limited to, chromosomal, episomal, and virus derived vectors, for example vectors from bacterial plasmids, bacteriophage, transposons, yeast episomes, insertion elements, yeast chromosomal elements, viruses such as baculoviruses, papova viruses, such as SB40, vaccinia viruses, adenoviruses, fowl pox viruses, pseudorabies viruses and retroviruses, and vectors derived from combinations of such viruses, such as those derived from plasmid and bacteriophage genetic elements, such as cosmids and phagemids. The expression system constructs may contain control regions that regulate as well as engender expression. Generally, any system or vector which is suitable to maintain, propagate or express polynucleotides and/or to express a polypeptide in a host can be used for expression. The appropriate DNA sequence can be inserted into the chosen expression by any of a variety of well-known and routine techniques, such as, for example, those set forth in Sambrook et al, Molecular Cloning, A Laboratory Manual, (supra).

Appropriate secretion signals, either homologous or heterologous, can be incorporated into the expressed polypeptide to allow the secretion of the protein into the lumen of the endoplasmic reticulum, the periplasmic space or the extracellular environment.

The polypeptides of the present invention can be recovered and purified from recombinant cell cultures by any of a number of well known methods, including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. It is most preferable to use high performance liquid chromatography (HPLC) for purification. Any of the well known techniques for protein refolding can be used to regenerate an active confirmation if the polypeptide is denatured during isolation and/or purification.

This invention is also related to the use of the polynucleotides of the invention as diagnostic reagents. Detection of a mutated form of a gene can be used as a diagnostic tool that to assist in the diagnosis of a disease or of susceptibility to a disease which results from under-expression, over-expression or altered expression of the gene. A variety of well known techniques can be used to detect, at the DNA level, an individual who has a mutation in the gene.

Nucleic acids for diagnosis may be obtained from an infected individual's cells and tissues, such as bone, blood, muscle, cartilage and skin. Genomic DNA can be used directly for detection or can be amplified prior to analysis using PCR or other amplification techniques. RNA or cDNA can also be used in the same manner. Deletions and insertions can be detected by a change in the size of the amplified product as compared to the genotype of a reference sequence. Point mutations can be identified by hybridizing amplified DNA to labeled polynucleotide sequences of the invention. Sequences that are perfectly matched can be distinguished from mismatched duplexes by RNase digestion or by differences in the melting temperature. Sequence differences can also be detected, at the DNA level, by comparing electrophoretic mobility of DNA fragments in gels, with or without denaturing agents; or by direct DNA sequencing (See, for example, Myers et al., *Science* 230: 1242 (1985)). A sequence change at a particular location can also be detected using nuclease protection assays, such as RNase and S1 protection or a chemical cleavage method (See, for example, Cotton et al., *Proc. Natl. Acad. Sci., USA,* 85: 4397–4401 (1985). It is anticipated that an array of oligonucleotide probes comprising a DAGAT nucleotide sequence or fragments thereof can be used for screening, particularly for genetic mutations. Array technology methods are well known and are useful in gene expression, genetic linkage and genetic variability analyses (See, for example, M. Chee et al., *Science,* 274: 610–613 (1996)).

The invention further provides a method for diagnosing or determining a susceptibility to a disease associated with DAGAT activity, particularly diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis, by determining from a sample an abnormally altered level of polypeptide or mA. Altered expression can be measured at the RNA level by any of the techniques well known in the art for quantitation of polynucleotides, including, but not limited to, amplification, PCR, RT-PCR. RiNase protection, Northern blotting and other hybridization methods. Diagnostic assays are also contemplated which detect levels of protein expression including, but not limited to radioimmunoassays, competitive-binding assays, Western Blot analysis and ELISA assays.

The nucleotide sequences of the present invention can also be used in chromosome identification.

The polypeptides of the invention or variants thereof, or cells expressing them can be used as an immunogen to produce antibodies which are immunospecific for polypeptides of the present invention. "Immunospecific" means that the antibodies have a substantially greater affinity for the polypeptides of the present invention as compared to the affinity of the antibodies for other related polypeptides. "Antibodies" includes monoclonal and polyclonal antibodies, including chimeric, single chain, simianized, humanized, resurfaced and other types of complementarity determining region (CDR) replaced antibodies, as well as Fab fragments, including products of an Fab immunoglobulin expression library.

Antibodies can be obtained by administering the polypeptides or epitope bearing fragments, analogs or cells to an animal, preferably non-human, using routine protocols. Any of the well known techniques continuous cell culturing techniques can be used to prepare monoclonal antibodies including hybridoma technology (See for example, Kohler, G. and Milstein, C., *Nature* 256:495–497 (1975)); trioma technology; human B-cell hybridoma technology (Kozbor et al., *Immunology Today* 4:72 (1983)); and the EBV-hybridoma technology (Cole et al., *Monoclonal Antibodies and Cancer Therapy*, Alan R. Liss, 77–96, (1985)).

Single chain, humanized, resurfaced, simianized and other types of CDR replaced antibodies can be produced according to techniques which are well known in the art.

The described antibodies can be used to isolate or identify clones that express the polypeptide or to purify polypeptides by affinity chromatography. The antibodies can also be used to treat diseases associated with DAGAT activity, particularly diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis.

The present invention also relates to genetically engineered soluble fusion proteins which comprises a polypeptide of the present invention, or a fragment thereof, fused to portions of the constant regions of the heavy or light chains of immunoglobulins of the various subclasses (IgG, IgM, IgA and IgE). Preferably the constant portion of the heavy chain of human IgG, particularly IgG1, is used with fusion at the hinge region. Particularly preferred is the use of Fc portion. (See, for example, WO 94129458 and WO 94/22914)

Polypeptides of the present invention can also be used to identify compounds which bind to the polypeptide, and in particular, inhibit or stimulate the activity of the polypeptide by binding. The binding of small molecule substrates and ligands can be assessed in, for example, cells, cell-free preparations, chemical libraries, and natural product mixtures. The agonists or antagonists/inhibitors can be natural substrates or ligands or can be structural or functional mimetics thereof. See, for example, Coligan et al., Curr Prot in Immuno, 1(2):Chapter 5 (1991).

The invention also provides a method for screening compounds to identify those compounds that bind to the polypeptides or polynucleotides of the present invention and particularly those compounds that enhance (agonist) or inhibit (antagonist) the action of polypeptides or polynucleotides of the invention. High throughput screening techniques can be used. As an example, to screen for agonists or antagonists, a synthetic reaction mix, a cellular compartment, such as a membrane, cell envelope or cell wall, or a preparation of any of these, comprising a polypeptide of the invention and a labeled substrate or ligand of such polypeptide is incubated in the absence or presence of a candidate compound that is being screening. The ability of the candidate compound to agonize or antagonize a polypeptide of the invention is detected by a decrease in binding of the labeled ligand or a decrease in the production of product from the substrate. Candidate compounds that bind gratuitously, without inducing the effects of a polypeptide of the invention, are most likely to be good antagonists. On the other hand, compounds that bind well and increase the rate of product production from substrate are considered agonists. The detection of the rate or level of production of product from substrate can be enhanced by using a reporter system such as, but not limited to, colorimetric labeling, inclusion of a reporter gene that is responsive to changes in polynucleotide or polypeptide activity and binding assays known in the art.

Competitive assays that combine a polypeptide of the invention and a potential antagonist with a compound that binds the polypeptide, natural substrates or ligands, or substrate or ligand mimetics can also be used to screen for antagonist compounds. The polypeptide of the invention can be label, such as by radioactivity or colorimetric compound, such that the number of such polypeptide molecules that bound to the binding molecule or converted to product can be determined to assess the effectiveness of the potential antagonist.

Potential antagonists can include, but are not limited to, small organic molecules, peptides, polypeptides and antibodies that bind to a polynucleotide or polypeptide of the invention and thereby inhibit or partially or completely block its activity. Antagonists can also include small organic molecules, peptides, polypeptides and antibodies that bind to the same site on a binding molecule without inducing the activities that are induced by a polypeptide of the invention, thereby preventing the action of the polypeptide by blocking it from binding. Potential antagonists also include small molecules that bind to and occupy the binding site of the polypeptide thereby preventing the polypeptide from binding to cellular binding molecules, so as to prevent or reduce normal biological activity of the polypeptide. Examples of such small molecules include, but are not limited to, small organic molecules, peptides and peptide like molecules. Other potential antagonists include antisense molecules (see, for example, Okano, *J. Neurochem,* 56: 560 (1991); Oligodeoxynucleotides as Antisense Inhibitors of Gene Expression, CRC Press, Boca Raton, Fla. (1988)).

Antagonists and agonists of DAGAT activity are particular useful as DAGAT is important in the formation of chylomicra in small intestine, VLDL in liver, and for storage of energy as triacylglycerol in adipose tissue. Thus, inhibiting DAGAT activity in small intestine, liver, and adipose tissues will reduce lipid absorption and plasma triglyceride levels and will decrease adipogenesis. Further, hypertriglyceridemia has been shown to be an independent risk factor for atherosclerosis (Kugiyama, K., et al., (1998) *Circulation* 97:2519–2526,) and is a marker for increased risk of coronary artery disease and can serve as a marker for several atherogenic factors. (Grundy, S. M., (1998) *Am. J. Cardiol,* 81:18B–25B). Compounds that inhibit DAGAT activity are also useful in controlling intestinal fat absorption, altering TAG rich lipoprotein secretion and controlling serum TAG and reducing adipogenesis (Owen M R, et al. (1997) *Biochem J* 323:17-2 1, Jamdar S C and Cao W F (1995) *Biochim Biophys Acta* 1255:237–243). Furthermore, the diacylglycerol substrate of DAGAT is a signal transducing molecule within the cell and is a known modulator of protein kinase C activity. Altered cellular diacylglycerol concentration and PROTEIN KINASE C activity has been associated with cancer (da Costa et al.,(1993) *J. Biol. Chem.* 268:2100–2105), diabetes (Koya D and King G L (1998) *Diabetes* 47:859–866), heart failure (Okumura, et al., (1991) *J. Mol. Cell. Cardiol.* 23:409–416), adipocyte (Baldo et al., (1995) *J. Lipid Res.,* 36:1415–1426), leukemia and skin carcinoma cells (Goldkom T., and Ding, T. (1997) *Adv. Exp. Med. Biol.,* 400A:461–472), and rat fibroblasts (Pai et al., (1991) *Proc. Natl. Acad. Sci.,* 88:598–602). As such, agonists and antagonists of the invention are particularly useful in treating or ameliorating diseases associated with DAGAT activity, including diseases associated with altered cellular diacylglycerol concentration or protein kinase C activity, including, but not limited to cancer; diabetes; cardiopulmonary diseases including, but not limited to heart failure, and atherosclerosis; adipocytosis; leukemia and skin carcinoma; fibroblastoma; metabolic disorders; obesity; diseases associated with abnormal lipid metabolism; diseases associated with abnormal fat absorption, lipoprotein secretion and adipogenesis.

The invention also relates to compositions comprising the polynucleotide or the polypeptide, or variants, agonists or antagonists thereof. The polypeptides of the invention can be used in combination with a sterile or non-sterile carrier or carriers for use with cells, tissues or organisms, such as a pharmaceutical carrier suitable for administration to a subject. Such compositions comprise, for example, a therapeutically effective amount of a polypeptide or other compound of the invention and a pharmaceutically acceptable carrier or excipient. Such carriers include, but are not limited to, saline, buffered saline, dextrose, water, glycerol, ethanol and combinations thereof. The formulation should be consistent with the mode of administration. The invention further relates to diagnostic and pharmaceutical packs or kits comprising one or more containers filled with one or more of the ingredients of the aforementioned compositions of the invention.

Polypeptides and other compounds of the invention may be administered alone or in combination with other compounds.

The pharmaceutical compositions can be administered in any effective, convenient manner including, but not limited to, topical, oral, anal, vaginal, intravenous, intraperitoneal, intramuscular, subcutaneous, intranasal or intradermal routes.

The required dosage range will depend on the peptide or other compound of the present invention that is used, the route of administration, the nature of the formulation, the nature of the subject's condition and the judgment of the practitioner. Suitable dosages will generally be in the range of approximately 0.1 to 100 $\mu$g/kg. The large variation in the dosage is expected due to the variety of compounds and the differences in the efficacy of administration. As an example, it is expected that oral administration would require higher dosages than intravenous administration. The skilled practitioner can determine the appropriate dosage using standard empirical methods.

Polypeptides can also be generated endogenously in the subject, which is generally referred to as "gene therapy" For example, cells from a subject may be engineered with a polynucleotide, such as a DNA or RNA, to encode a polypeptide, ex vivo, and by the use of a retroviral plasmid vector. The cells are then introduced into the subject.

The polynucleotide and polypeptide sequences can also be used to identify additional sequences which are homologous to the sequences of the present invention. The most preferable and convenient method is to store the sequence in a computer readable medium, for example, floppy disk, CD ROM, hard disk drives, external disk drives and DVD, and then to use the stored sequence to search a sequence database with well known searching tools. Examples of public databases include the DNA Database of Japan (DDBJ) (http://www.ddbj.nig.ac.jp/); Genebank (http://www.ncbi.nlm.nih.gov/web/Genbank/Index.htlm); and the European Molecular Biology Laboratory Nucleic Acid Sequence Database (EMBL) (http://www.ebi.ac.uk/ebi docs/embl db.html). A number of different search algorithms are available to the skilled artisan, one example of which are the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). Additional programs are available in the art for the analysis of identified sequences, such as sequence alignment programs, programs for the identification of more distantly related sequences, and the like, and are well known to the skilled artisan.

The invention now being generally described, it will be more readily understood by reference to the following examples which are included for purposes of illustration only and are not intended to limit the present invention.

EXAMPLES

Example 1

Diacylglycerol Acyltransferase (DAGAT) Assays

Methods to assay for DAGAT activity in non-solubilized or solubilized protein preparations are described for *Mortierella ramanniana*.

A. Non-solubilized Samples

DAGAT activity is assayed with 3.67 $\mu$M 1-$^{14}$C-18:1-Coenzyme A (53.5–54.5 Ci/mole, New England Nuclear, Boston, Mass.) and 1.5 mM 1,2-18:1 diacylglycerol (DAG) (Sigma D-0138, prepared as a 150 mM stock in 2-methoxyethanol) in a buffer containing 10 mM potassium phosphate (pH 7.0), 100–150 mM KCl, and 0.1% TX-100 (w/v) in a total volume of 100 $\mu$l as similarly described by Kamisaka et al. (1993) supra and Kamisaka et al. (1994) supra. Assays are performed at 30° C. for 5 min and terminated with the addition of 1.5 ml of heptane:isopropanol:0.5M H$_2$SO$_4$ (10:40:1, v/v/v). If necessary, samples may be diluted with buffer prior to assay in order to maintain a linear rate of product formation during the assay.

B. Solubilized Samples

The assay is performed as described for non-solubilized samples with the following changes: the amount of 1,2-18:1 DAG is reduced to 0.5 mM, the amount of Triton X-100 is increased to 0.2%, and the KCl concentration is maintained between 100–125 mM. It is also necessary to include L-α-phosphatidic acid (Sigma P-9511, prepared as a 50 mM stock in 1% Triton X-100 (w/v)) to recover activity following solubilization with detergent as described by Kamisaka et al. (1996 and 1997) supra, with the following modifications of the protocol. The use of 300 $\mu$M phosphatidic acid rather than 500 $\mu$M gives a higher stimulation of DAGAT activity following treatment by Triton X-100. In addition, the DAGAT activity is sensitive to the amount of KCl introduced in the assay with the optimum level between 100–125 mM. Assays are performed at 30° C. for 5–30 minutes and terminated as described for non-solubilized samples.

C. Processing of Sample Assays

After the assays are terminated, the samples can be stored at 4° C. for processing at a later date or immediately processed by addition of 0.1 ml 1 M NaHCO$_3$ followed by 1 ml of heptane containing 15 nmoles/ml triolein as a carrier for extraction. The samples are vortexed and, after separation of aqueous and organic phases, the upper organic phase is removed to a new glass vial and washed with 1 ml 1 M NaCl. Forty percent of the final organic phase is removed for liquid scintillation counting and the remaining organic phase is transferred to a clean vial and evaporated to dryness under nitrogen gas. The residue is resuspended in 45 $\mu$l hexane and spotted onto a silica gel-G, glass, thin-layer chromatography (TLC) plate with a pre-adsorbent loading zone (Analtech #31011, Newark, Del.). The TLC plate is developed in hexane:diethyl ether:acetic acid (50:50:1, v/v/v) to the top then dried and scanned by a radio-image analyzer (AMBIS 3000, San Diego, Calif.) to determine the portion of radioactivity incorporated into triacylglycerol. Activity is reported in units as pmole/min.

Example 2

*Mortierella ramanniana* Culture Conditions

*Mortierella ramanniana* is cultured by inoculating 1 liter of Defined Glucose Media (30 g glucose, 1.5 g (NH$_4$)$_2$SO$_4$, 3 g K$_2$HPO$_4$, 0.3 g MgSO$_4$. 7H2O, 0.1 g NaCl, 5 gCH$_3$COONa.3H$_2$O, 10 mg FeSO$_4$.7H$_2$O, 1.2 mg CaCl$_2$.2H$_2$O, 0.2 mg CuSO$_4$. 5H$_2$O, 1.0 mg ZnSO$_4$.7H$_2$O, 1.0 mg MnCl$_2$.4H$_2$O, 2 mg thiamine-HCl and 0.02 mg biotin in 1 L of water purified by reverse osmosis (pH 5.7)) with 1.5–3×10$^6$ spores and incubating at 30° C. with shaking at 200 rpm for 9–11 days Cultures are harvested by filtration through one layer of Miracloth (Calbiochem, La Jolla, Calif.). Excess liquid is removed by hand squeezing. The average yield of packed cells per liter harvested is 22.5 g.

Example 3

SDS-PAGE Analysis

Samples from the column fractions are diluted in SDS-PAGE sample buffer (1×buffer=2% SDS w/v, 250 mM β-mercaptoethanol, 0.0025% bromphenol blue) and analyzed by electrophoresis. Polyacrylamide gradient gel electrophoresis (10–13%) is carried out according to the method of Laemmli ((1970) *Nature* 227:680–685) with some of the modifications of Delepelaire (1979) *Proc. Natl. Acad. Sci. USA* 76:111–115. Sodium dodecyl sulfate is used in the upper reservoir buffer at 0.1% but is omitted from the lower reservoir buffer, stacking and resolving gels. The stacking gel contains 5% of a 30% acrylamide stock (acrylamid:N, N'-Methylenacrylamid, 37.5:1, Bio-Rad, Hercules, Calif.), 0.06% ammonium persulfate and 0.1% TEMED (v/v). The resolving gel contains a 10–13% linear gradient of acrylamide stock stabilized by a 0–10% linear gradient of sucrose. Electrophoresis is carried out at room temperature at 150V, constant voltage, for 7–9 hours. Proteins are visualized by staining with silver according to the method of Blum et al. (1987) *Electrophoresis* 8:93–99, or with Coomassie Blue (0.1% Coomassie Blue R-250, 50% methanol (v/v), 10% acetic acid (v/v)).

Example 4

Evaluation of the Chromatography Used by Kamisaka et al. (1997) in the Purification of DAGAT

A. Preparation of the Lipid Body Fraction

The following steps are performed at 4° C.

Typically, 70–75 g of wet packed *Mortierella ramanniana* cells (stored at −70° C.) are used for each lipid body preparation. Just prior to use, cells are thawed on ice and resuspended in 150 ml of Buffer A (10 mM potassium phosphate (pH 7.0), 0.15 M KCl, 0.5 M sucrose, and 1 mM EDTA). The following protease inhibitors are added to reduce proteolysis: 0.1 µM Aprotinin, 1 µM Leupeptin, and 100 µM Pefabloc (all from Boehringer Mannheim, Germany). Cells are divided into five, 50-ml tubes and lysed with a Polytron Tissue Homogenizer (Kinematic GmbH, Brinkman Insruments, Switzerland) on setting #7 with a 1 cm diameter probe for 7×1 min. The resulting slurry is transferred to centrifuge tubes (29×104 mm) and solid debris made to pellet by spinning at 1500×g (Beckman Instruments, J2–21, JA-20 rotor, 3500 rpm) for 10 min at 4° C. The supernatant is removed and the pellets washed with another 5 ml of Buffer A. Following centrifugation, the supernatant volumes are combined. This fraction is referred to as the 'S1'. The S1 is divided into six ultracentrifuge tubes (25×89 mm, Beckman Instruments, Fullerton, Calif.) and each is overlayed with 5 ml of Buffer B (10 mM potassium phosphate, pH 7.0,0.15 M KCl, 0.3 M sucrose, and 1 mM EDTA). Samples are centrifuged at 100,000×g (Beckman Instruments. L8-M, SW-28 rotor, 21000 rpm) at 4° C. for 3 hours. The Lipid Body Fraction (LBF), floating on top of the overlay, is recovered with a spatula and transferred to a glass homogenizer (Potter-Elvehjem). Small amounts of LBF remaining in the centrifuge tube are recovered with a pipette by removing 4 ml of the Buffer B overlay and combining it with the LBF in the homogenizer. The final LBF is homogenized in 40 ml of Buffer B. The remaining fractions are collected as follows: Interface fraction (the interface between the 0.3 and 0.5 M sucrose buffers), Soluble fraction (the liquid volume beneath the interface), and the Membrane fraction (a tan/brown pellet at the bottom of each tube). All are frozen and stored at −70° C. for solubilization and further purification.

B. Solubilization of DAGAT Activity

The LBF is thawed on ice and solubilization is achieved by addition of Triton X-100 (Boehringer Mannheim, Mannheim, Germany) from a 10% (w/v) stock to a final concentration of 1.3% (w/v). Solid sucrose (Mallinckrodt, Paris, Ky.) is added to achieve a final concentration of 0.5M. The detergent-treated sample is rocked at 4° C. for one hour then divided into six ultracentrifuge tubes (25×89 mm, Beckman Instruments). Each tube is overlayed with 5 ml of Buffer B. Samples are centrifuged at 100,000×g (Beckman Instruments, L8-M, SW-28 rotor, 21000 rpm) at 4° C. for 3 hours. The solubilized material, referred to as the 'Triton X-100 extract', is recovered by inserting a thin tube through the overlay to within 1 cm of the bottom of each ultracentrifuge tube and removing the lower, 0.5M sucrose, layer with gentle suction while leaving the upper 0.3M sucrose overlay (including a floating fat layer) and the pellet behind.

In the protocol described by Kamisaka et al. (1997) supra, the Lipid Body Fraction was solubilized with 0.1% (w/v) Triton X-100 and further centrifuged at 100,000×g or filtered through a 0.2 µm filter. As described in Kamisaka et al. (1997) supra it was necessary to increase the Triton X-100 concentration to 1.5% for DAGAT activity to bind the first column.

C. Chromatography used in the Purification of DAGAT

Buffer C, used for chromatography, contains 10 mM potassium phosphate (pH 7.0), 0.1% Triton X-100 (w/v) (Boehringer Mannheim, Mannheim, Germany), 10 % glycerol (w/v), 0.1 µM Aprotinin, 1 µM Leupeptin, 100 µM Pefabloc (all from Boehringer Mannheim, Mannheim, Germany) and varying amounts of potassium chloride (75–500mM). This buffer differs from the corresponding column buffer used by Kamisaka et al.( 1997) supra, in that glycerol is substituted for ethylene glycol and EDTA, DTT, and PMSF are omitted while Aprotinin, Leupeptin and Pefabloc are included. Following the protocol by Kamisaka et al. (1997) supra, a Yellow 86-Agarose (Sigma R-8504, St. Louis, Mo.) column is prepared (1.5 cm×5.8 cm) and equilibrated with 150 mM KCl in Buffer C. The majority of the DAGAT activity present in the Triton X-100 extract did not bind the Yellow 86-Agarose column. However, a significant portion of the DAGAT activity was bound to the column by diluting the KCl concentration of the applied sample to 75 mM with an equal volume of Buffer C (without KCl). In accordance, the Yellow 86-Agarose column is also equilibrated in 75 mM KCl in Buffer C. Following application of the sample at 0.56 ml/min, the column is washed with 4 column volumes of equilibration buffer. DAGAT activity and proteins bound to the column are eluted with 500 mM KCl in Buffer C (FIG. 1).

Figure 2A:
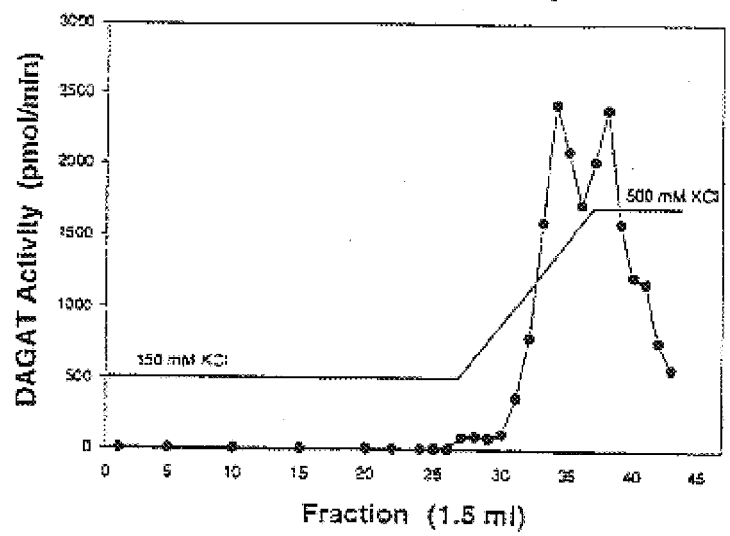
FIG. 2A shows the results of chromatography of *Mortierella ramanniana* DAGAT activity from the Yellow 86-Agarose column on a column of Heparin Sepharose CL6B.

DAGAT activity eluted from the Yellow 86-Agarose column (fractions 17–20) is diluted 1:3.33 with Buffer C to reduce the KCl concentration to 150 mM. The diluted pool (103 ml) is applied to a Heparin-Sepharose CL-6B column (Pharmacia, Uppsala, Sweden, 0.5 cm×4.8 cm) equilibrated with 150 mM KCl in Buffer C at 0.2 ml/min. The column is washed with 5 volumes of equilibration buffer and DAGAT activity and protein are eluted in a 15 ml linear gradient of 150–500 mM KCl in Buffer C. DAGAT activity elutes in two overlapping peaks. The first peak elutes during the gradient, as found by Kamisaka et al. (1997) supra, and a second peak, not found by Kamisaka et al., elutes at the end of the gradient with much less protein (FIG. 2A).

A portion (250 µl) of the two peak fractions from the Heparin column are further purified by size exclusion chromatography on a Superdex-200 column (1×30 cm, Bio-Rad, Hercules, Calif.) at 0.2 ml/min equilibrated with 150 mM KCl in Buffer C. For calibration only, the column is equilibrated with 150 mM KCl in a Modified Buffer C in which Triton X-100 is replaced with Triton X-100 R (Calbiochem, La Jolla, Calif.). The column is calibrated using Bio-Rad Gel Filtration Standards. The DAGAT activity from each of the two peaks from Heparin-Sepharose CL-6B elutes at an estimated molecular mass of 99 kDa.

Figure 3A:
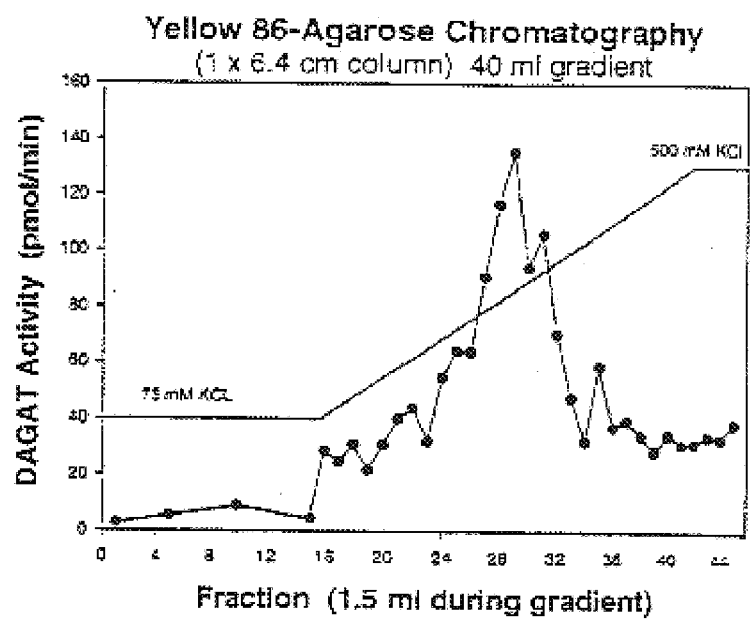
FIG. 3A shows the results of chromatography of *Mortierella ramanniana* DAGAT activity from the second activity peak of the Heparin Sepharose CL6B column chromatographed on a Yellow 86-Agarose column where protein was eluted during a gradient of 75–150 mM KCl.

Additional chromatography is performed on the later eluting peak from the Heparin column, which contained DAGAT at a higher specific activity. In this case, the second peak from the Heparin column (fractions 36–41) is diluted 1:6.6 with Buffer C to a volume of 46.7 ml. The sample is applied to a Yellow 86 Agarose column (1.0 cm×6.4 cm) equilibrated with 75 mM KCl in Buffer C at 0.5 ml/min. After washing with 5 column volumes of equilibration buffer, bound proteins and all of the DAGAT activity elute in a 40 ml linear gradient of 75–500 mM KCl in Buffer C. DAGAT activity elutes as a single peak (FIG. 3A).

Figure 2B:
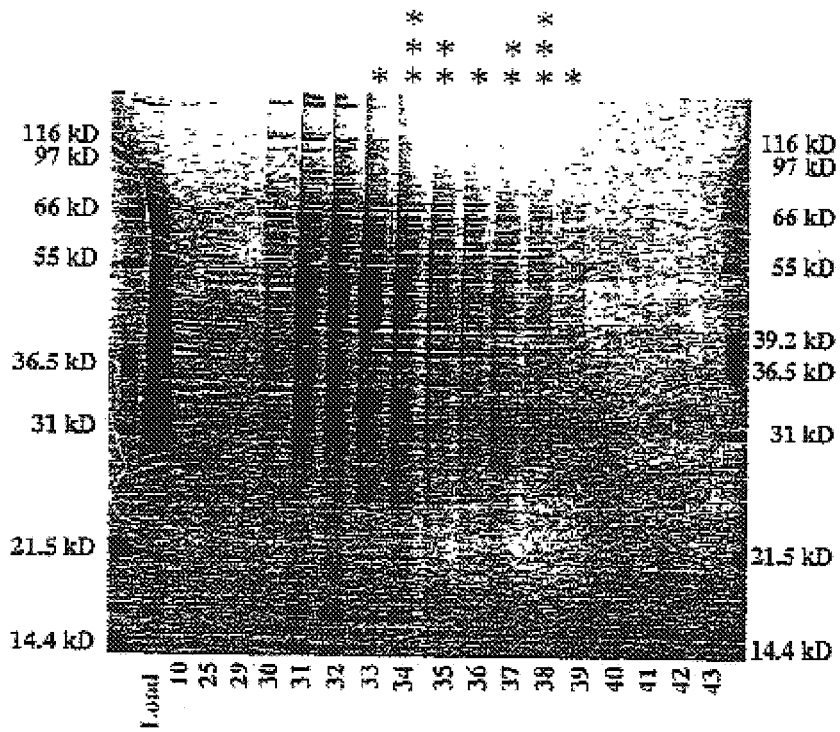
FIG. 2B shows SDS-PAGE analyses of fractions from the Heparin Sepharose CL6B column. Protein bands are detected by silver stain.
Figure 3B:
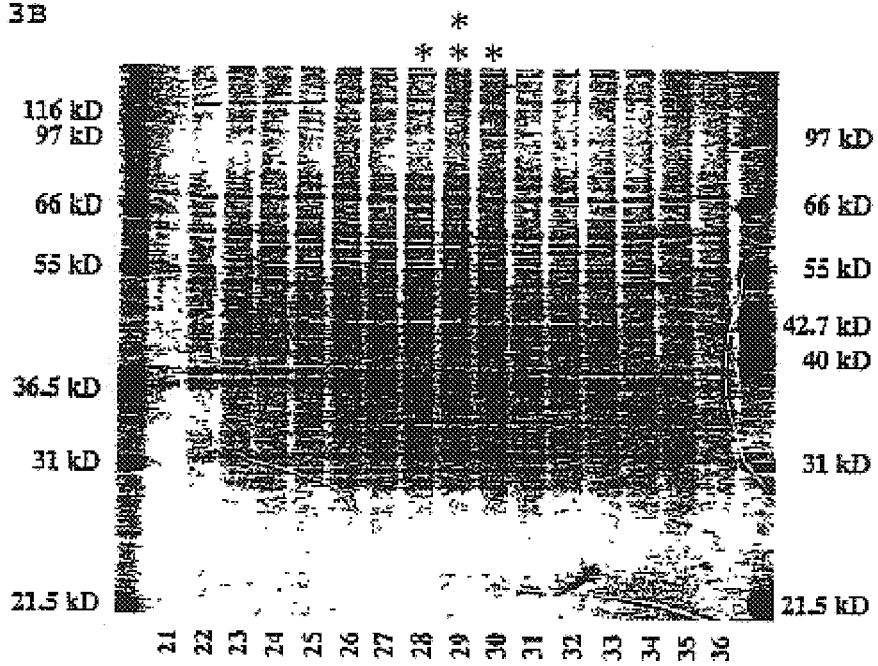
FIG. 3B shows SDS-PAGE analyses of fractions from the Yellow 86-Agarose column. Protein bands are detected by silver stain.

The protein composition of the fractions containing DAGAT activity from the Heparin and second Yellow 86 columns are analyzed by gradient SDS-PAGE according to the protocol in Example 3. Protein bands are detected by silver-staining. The pattern of bands eluting from these columns is compared, fraction by fraction, to the respective DAGAT activity profile. Many protein candidates are present that correlate with the presence of DAGAT activity. This purification protocol is insufficient to identify a particular protein candidate associated with DAGAT activity (FIG. 2B, 3B).

Example 5

New Purification Protocol for Identifying DAGAT Protein Candidates

A. Preparation of the Lipid Body Fraction

The following steps are performed at 4° C.

Typically, 70–75 g of wet packed *Mortierella ramanniana* cells (stored at −70° C.) are used for each lipid body preparation. Just prior to use, cells are thawed on ice and resuspended in 150 ml of Buffer A (10 mM potassium phosphate (pH 7.0), 0.15 M KCl, 0.5 M sucrose, 1 mM EDTA). The following protease inhibitors are added to reduce proteolysis: 0.1 $\mu$M Aprotinin, 1 $\mu$M Leupeptin, and 100 $\mu$M Pefabloc (all from Boehringer Mannheim, Germany). Samples are lysed with a cell disrupter (Bead-Beater, Biospec Products, Bartlesville, Okla.) using 0.5 mm glass beads. The sample chamber is filled with 180 ml of glass beads. Wet-packed cells are thawed on ice and resuspended in 150 ml of Buffer A. The cell slurry is poured over the glass beads. In general, an additional 40–50 ml of Buffer A are needed to fill the chamber for proper functioning. This volume is used to rinse the remains of the cell slurry from its original container so that it can be combined with the rest of the sample. Cells are ground ('Homogenize' setting) for 45–90 seconds depending on the viscosity of the sample. The cell slurry containing glass beads is divided into tubes (29×104 mm) and centrifuged at 500×g (Beckman Instruments, GP centrifuge, GH 3.7 Horizontal rotor at 1500 rpm) and 4° C. The supernatant is removed and the pellets washed with another 5 ml of Buffer A. Following centrifugation the supernatant volumes are combined. This fraction is referred to as the 'S1'. The S1 is divided into six ultracentrifuge tubes (25×89 mm, Beckman Instruments) and each is overlayed with 5 ml of Modified Buffer B (10 mM potassium phosphate, pH 7.0, 0.15 M KCl, and 0.3 M sucrose). EDTA is omitted from Buffer B (see Example 4) since it interferes with hydroxylapatite chromatography. Samples are centrifuged at 100,000×g (Beckman Instruments, L8-M, SW-28 rotor, 21000 rpm) at 4° C. for 3 hours. The Lipid Body Fraction (LBF), floating on top of the overlay, is recovered with a spatula and transferred to a glass homogenizer. Small amounts of LBF remaining in the centrifuge tube are recovered with a pipette by removing 4 ml of the Buffer B overlay and combining it with the LBF in the homogenizer. The final LBF is homogenized in 40 ml of Buffer B. The remaining fractions are collected as follows: Interface fraction (the interface between the 0.3 and 0.5 M sucrose buffers), Soluble fraction (the liquid volume beneath the interface), and the Membrane fraction (a tan/brown pellet at the bottom of each tube). All are frozen and stored at −70° C. for solubilization and further purification.

B. Solubilization of DAGAT Activity from the Lipid Body Fraction

Prior to solubilization, a protein determination is made with an aliquot of the Lipid Body Fraction by the method of Bradford (Bio-Rad Reagent, Hercules, Calif.) using bovine serum albumin as a standard. The LBF is thawed on ice, then diluted to a concentration of 1 mg protein/ml and treated with Triton X-100 at a detergent to protein ratio of 15:1 (w/w, equivalent to 1.3% Triton X-100). Solid sucrose (Mallinckrodt, Paris, Kentucky) is added to achieve a final concentration of 0.5M. The detergent-treated sample is rocked at 4° C. for one hour then divided into six ultracentrifuge tubes (25×89 mm, Beckman Instruments). Each tube is overlayed with 5 ml of Modified Buffer B. Samples are centrifuged at 100,000×g (Beckman Instruments, L-8M, SW-28 rotor, 21000 rpm) at 4° C. for 3 hours. The solubilized material, referred to as the 'Triton X-100 extract', is recovered by inserting a thin tube through the overlay to within 1 cm of the bottom of each ultracentrifuge tube and removing the lower, 0.5M sucrose, layer with gentle suction while leaving the upper 0.3M sucrose overlay (including a floating fat layer) and the pellet behind.

C. DAGAT Column Chromatography

A purification method of Yellow 86-Agarose followed by hydroxylapatite chromatography is used to further purify the protein. The method is performed in two ways. In Protocol A, activity is bound to the first column and after elution, fractions are assayed for activity. The active fractions are then pooled and applied to the second column (also referred to as a sequential run). In Protocol B, activity is bound to the first column then elutes and flows directly onto the second column without pooling and assaying in between (also referred to as a tandem run).

Figure 4:
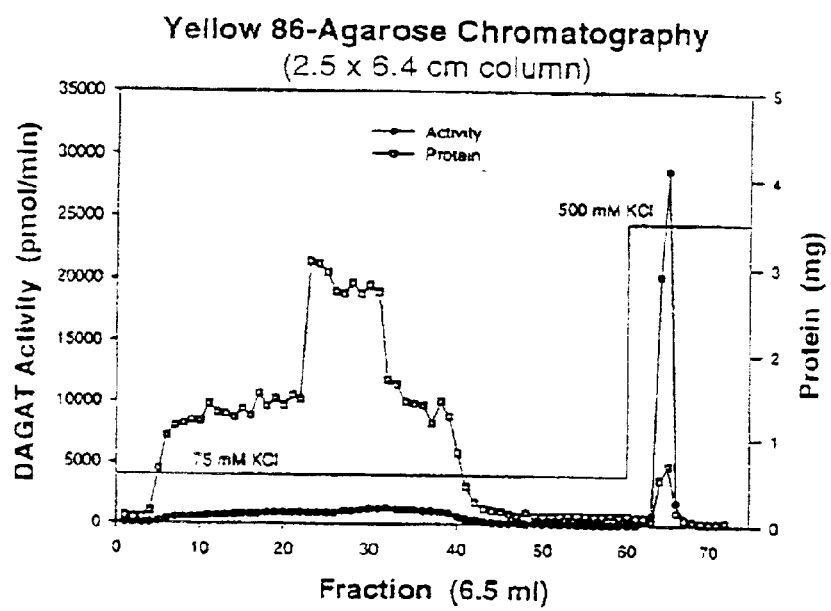
FIG. 4 shows the results of chromatography of *Mortierella ramanniana* DAGAT activity on a Yellow 86-Agarose column.
Figure 5A:
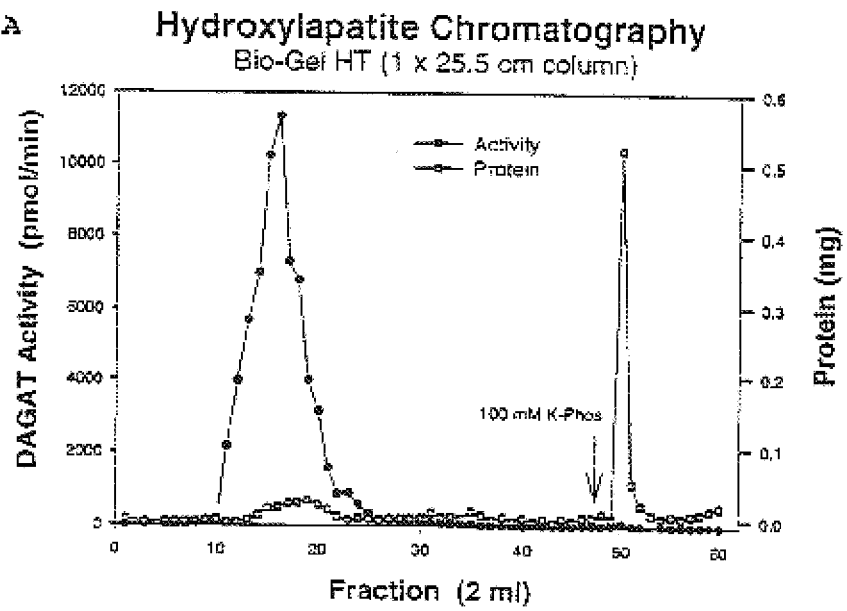
FIG. 5A shows the results of chromatography of *Mortierella ramanniana* DAGAT activity from the Yellow 86-Agarose column on a column of hydroxylapatite (Bio-Gel HT).
Figure 5B:
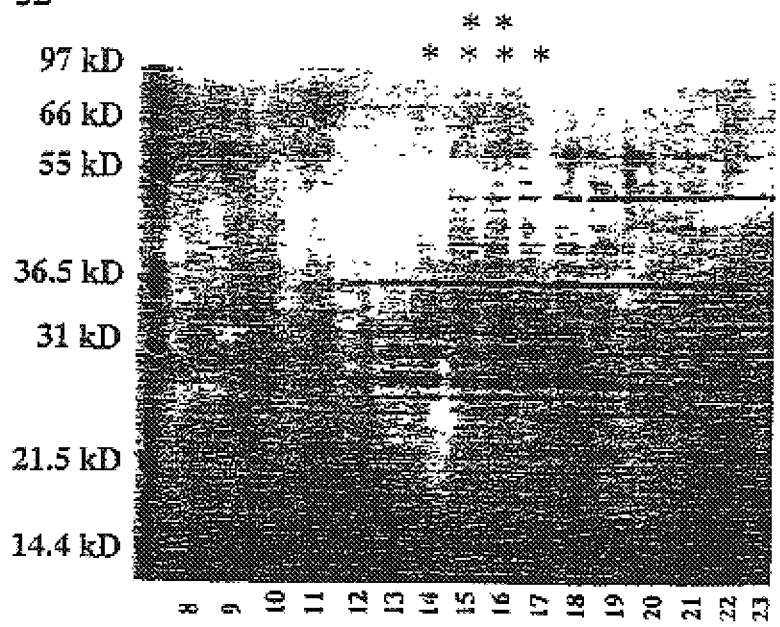
FIG. 5B shows SDS-PAGE analyses of fractions from the hydroxylapatite column. Protein bands are detected by silver stain.

In Protocol A, the Triton X-100 extract is applied to a Yellow 86-Agarose column (2.5 cm×6.4 cm) equilibrated with 75 mM KCl in Buffer C (Example 4.C) at 2 ml/min. The column is washed with 5 column volumes of equilibration buffer then eluted with 500 mM KCl in Buffer C at 0.5 ml/min (FIG. 4). The two most active fractions (64 and 65), containing 93% of the eluted activity, are pooled and loaded onto a hydroxylapatite column (Bio-Gel HT, Bio-Rad, 1 cm×25.5 cm) equilibrated with 500 mM KCl in Buffer C at 0.5 ml/min. DAGAT activity flows through the column whereas the majority of the proteins bind the column. The column is washed with 3 volumes of equilibration buffer. Bound proteins are eluted with 100 mM dipotassium phosphate and 500 mM KCl in Buffer C at 0.5 ml/min (FIG. 5A). A portion of the fractions containing the DAGAT activity peak are run on gradient gel SDS-PAGE as described in Example 9. The proteins are stained with silver and the pattern of the bands are compared, fraction by fraction, to the activity profile (FIG. 5B). Several DAGAT protein candidates correlate with activity. In particular, attention is called to bands migrating at positions corresponding approximately to 43 kD, 36.5 kD, 33 kDa, 29 kD, 28 kD and 27 kD. There does not appear to be a candidate protein in the region of 53 kD that correlates with activity.

In Protocol B, the Triton X-100 extract is applied to a Yellow 86-Agarose column (1.5 cm×5.8 cm) equilibrated with 75 mM KCl in Buffer C at 1 ml/min. The column is washed with column volumes of equilibration buffer. Then, the outlet from the Yellow 86-Agarose column is connected to the inlet of a hydroxylapatite column (1.0 cm×26.2 cm, Bio-Gel HT, Bio-Rad, Hercules, Calif.) equilibrated with 500 mM KCl in Buffer C. DAGAT activity bound to the Yellow 86 column is eluted with 110 ml of Buffer C containing 500 mM KCl and passes directly through the hydroxylapatite column at 0.2 ml/min. Finally, the hydroxylapatite column is disconnected from the Yellow 86-Agarose column and proteins bound to the hydroxylapatite column are eluted with 100 mM dipotassium phosphate and 500 nM KCl in Buffer C. DAGAT activity is found in fractions from the hydroxylapatite column collected during the 110-ml wash with Buffer C containing 500 mM KCl.

Figure 6A:
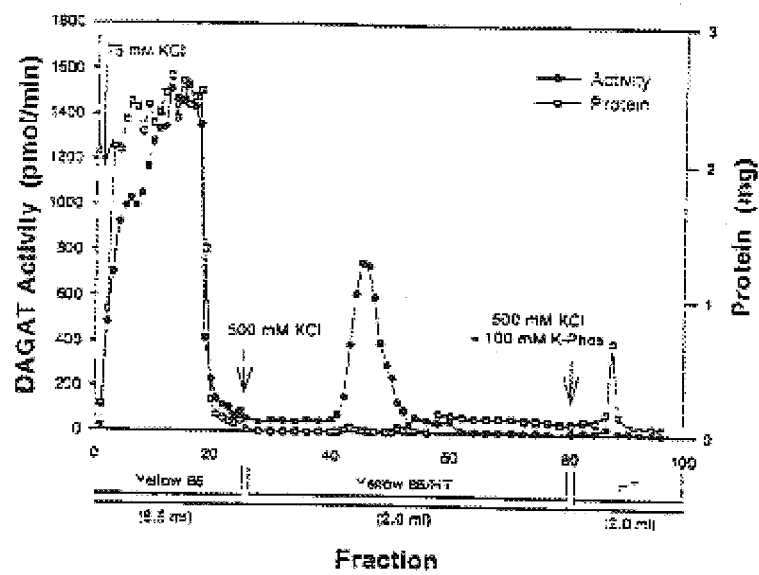
FIG. 6A provides results of tandem Yellow 86-Agarose/Hydroxylapatite chromatography.

The majority of the protein in the Triton X-100 extract does not bind the Yellow 86-Agarose column and is discarded. A small subset of proteins, including DAGAT, do bind the Yellow 86-Agarose column and are eluted with 500 mM KCl in Buffer C. When this eluate is applied to the hydroxylapatite column, DAGAT activity flows through while most of the remaining proteins bind the column and are separated (FIG. 6A). A portion of the fractions containing the DAGAT activity peak are run on gradient gel SDS-PAGE and are silver-stained. The pattern of bands eluting from these columns is compared, fraction by fraction, to the respective DAGAT activity profile. Examination of the stained protein bands indicate a protein at approximately 33 kDa correlates best with DAGAT activity (FIG. 6B).

Figure 6B:
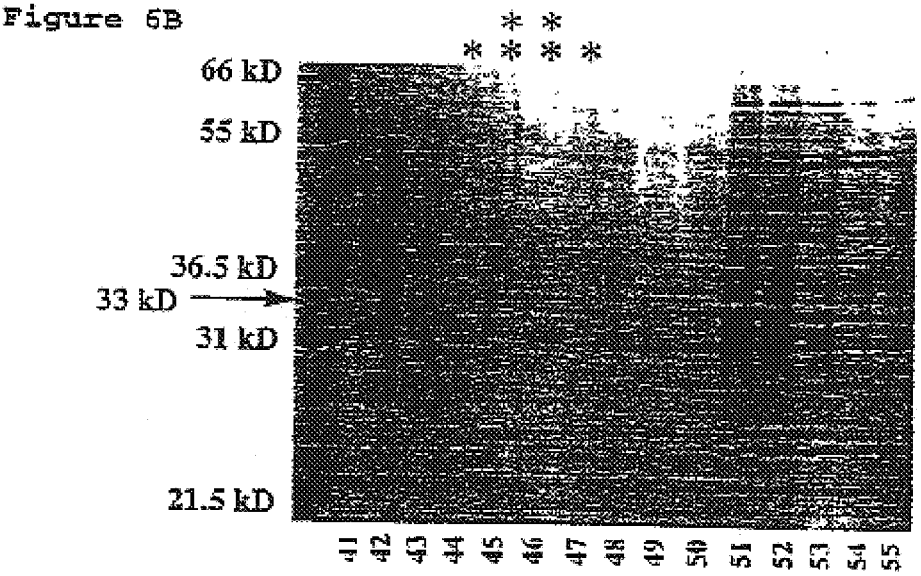
FIG. 6B provides results of SDS-PAGE analysis of the peak fractions from the tandem chromatography. Protein bands are detected by silver stain.

Protein sequence from the 36.5 kDa candidate seen in FIG. 5B and from the 33 kDa candidate seen in FIG. 6B are obtained as described in Examples 8 and 9 and the peptides are used to search the databases. Peptides generated from the 36.5 kDa candidate matched glyceraldehyde-3-phosphate (GAP) dehydrogenase. The best match to the peptides from the 33 kDa candidate is RNA helicase.

Example 6

Modified Protocol for Identifying DAGAT

A. Preparation of the Lipid Body Fraction

The following steps are performed at 4° C.

Typically, 70–75 g of wet *Mortierella ramanniana* packed cells (stored at −70° C.) are used for each lipid body preparation. Just prior to use, cells are thawed on ice and resuspended in 150 ml of Buffer A (10 mM potassium phosphate (pH 7.0), 1 M KCl, 0.5 M sucrose, 1 mM EDTA). The KCl concentration is increased from 0.15 M to 1 M in order to reduce the non-specific binding of soluble proteins with the Lipid Body Fraction. The following protease inhibitors are added to reduce proteolysis: 0.1 $\mu$M Aprotinin, 1 $\mu$M Leupeptin, and 100 $\mu$M Pefabloc (all from Boehringer Mannheim. Germany). Samples are lysed with a cell disrupter (Bead-Beater, Biospec Products, Bartlesville, Okla.) using 0.5 mm glass beads. The sample chamber is filled with 180 ml of glass beads. Wet-packed cells are thawed on ice and resuspended in 150 ml of Buffer A. The cell slurry is poured over the glass beads. In general, an additional 40–50 ml of Buffer A are needed to fill the chamber for proper functioning. This volume is used to rinse the remains of the cell slurry from its original container so that it can be combined with the rest of the sample. The chamber is surrounded by ice in order to keep the sample cool during lysis. Cells are ground ('Homogenize' setting) for 15 seconds then cooled for 1 minute and the process repeated 2 times. The cell slurry containing glass beads is divided into tubes (29×104 mm) and centrifuged at 1500×g (Beckman Instruments, GP centrifuge, GH 3.7 Horizontal rotor at 2460 rpm) for 10 minutes at 4° C. The supernatant is removed and the pellets washed with another 5 ml of Buffer A. Following centrifugation the supernatant volumes are combined. This fraction is referred to as the 'S1'. The S1 is divided into six ultracentrifuge tubes (25×89 mm, Beckman Instruments) and each is overlayed with 5 ml of Modified Buffer B (10 mM potassium phosphate, pH 7.0, 1 M KCl, and 0.3 M sucrose). EDTA is omitted from Buffer B (see Example 4) since it interferes with hydroxylapatite chromatography. Samples are centrifuged at 100,000×g (Beckman Instruments, L8-M, SW-28 rotor, 21000 rpm) at 4° C. for 3 hours. The Lipid Body Fraction (LBF), floating on top of the overlays, are recovered with a spatula and transferred to a glass homogenizer for solubilization. The remaining fractions are collected as follows: the Soluble fraction (the liquid volume beneath the Lipid Body Fraction) and the Membrane fraction (a tan/brown pellet at the bottom of each tube) is pooled from each tube and saved for assay. The membrane fraction is resuspended in 3.8–4 ml of Modified Buffer A (in which the KCl concentration has been reduced to 75 mM KCl).

B. Solubilization of DAGAT Activity from the Lipid Body Fraction

On the same day the final LBF is homogenized in 50 ml of Solubilization Buffer (10 mM potassium phosphate (pH 7.0), 75 mM KCl, 0.5M Sucrose, 1.5% Triton X-100) and the homogenate is centrifuged at 90,000×g for 1.8 hours SW-28 at 27k rpm). Following centrifugation the floating lipid layer is discarded and the solubilized layer (Triton X-100 extract) is pooled and stored at −70° C. awaiting further purification. The Triton X-100 extract is ready to load onto the first column without further dilution.

C. DAGAT Column Chromotography using Yellow 86-Agarose and HA in Tandem Mode (Protocol B)

Figure 7A:
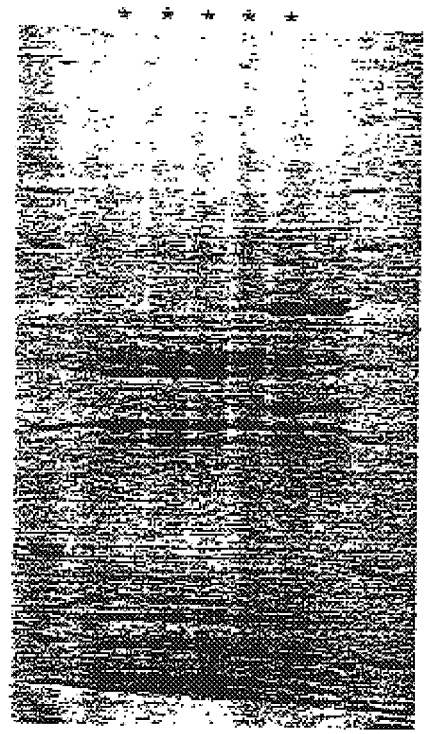
FIGS. 7A and 7B shows SDS-PAGE analyses of high salt and low salt preparation of lipid body fraction purified through Yellow 86-Agarose/Hydroxylapatite chromatography. Protein bands are detected by Coomassie Blue stain.

For comparison with the protocol described in Example 5, one Lipid Body Fraction is prepared as described in Example 5B (low salt) and another Lipid Body Fraction is prepared as described in Example 6B (high salt). Each preparation is solubilized with Triton X-100. The Triton X-100 extracts are chromatographed through Yellow 86-Agarose and hydroxylapatite as described in Example 5C, Protocol B. The amount of protein recovered in the high salt preparation is greater than that recovered in the low salt preparation as shown in FIG. 7A (high salt) and 7B (low salt). All subsequent preparations are made using the high salt protocol described in Example 6A/B.

Figure 7B:
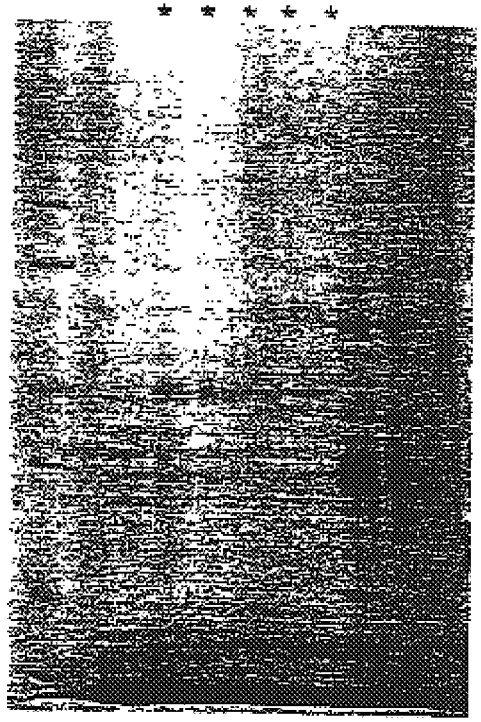

These two comparative preparations also reveal additional DAGAT protein candidates after SDS-PAGE analysis that are not seen previously, especially using the high salt protocol. Active fractions from the two purifications are prepared for in-gel digestion by precipitating fractions from the HA column as described in Example 8B and separated by gradient gel SDS-PAGE as described in Example 8C. Coomassie stained proteins of approximate sizes 55, 50, 39, 36.5, 36, 33, 32.5, 32, 29, and 27 kDa are excised from the gel made from the high salt preparation (FIG. 7A). Coomassie stained proteins of approximate sizes 39, 36.5, 36, 35, 32, 30 31, 29, and 27 kDa are excised from the gel made from the low salt preparation (FIG. 7B). These candidates are stored at −70° C. for later use in protein sequencing. The 36 kDa band from the high salt preparation was designated Mr18. The 36 kDa band from the low salt preparation was designated Mr19.

Figure 8A:
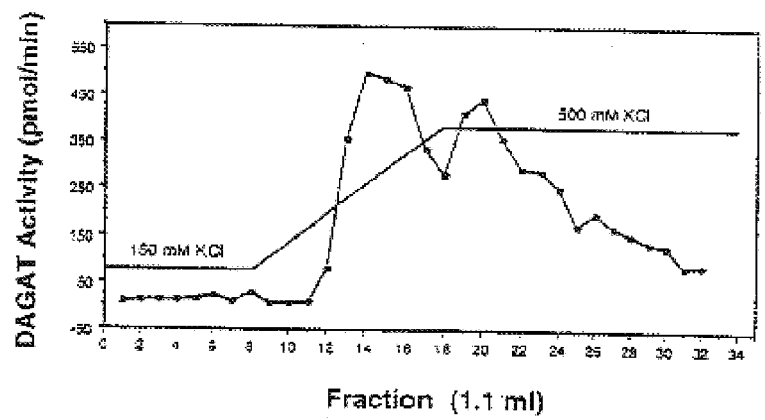
FIG. 8A shows the results of chromatography of *Mortierella ramanniana* DAGAT activity from the Heparin column following chromatography on Yellow 86-Agarose and hydroxylapatite (Bio-Gel HT).
Figure 8B:
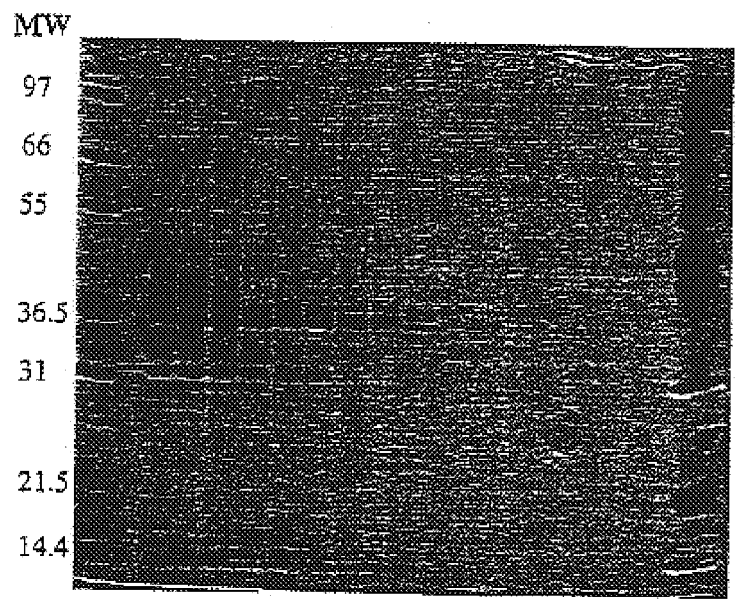
FIG. 8B shows SDS-PAGE analyses of fractions from the Heparin column. Protein bands are detected by silver stain.

D. DAGAT Column Chromatography Using Yellow 86-Agarose, Hydroxylapatite and Heparin The Triton X-100 extract described in Example 6B is thawed and applied to a Yellow 86-Agarose column (2.5 cm×6.4 cm) equilibrated with 75 mM KCl in Buffer C (10 mM potassium phosphate (pH 7.0), 0.1% (w/v) Tx-100, 10% (w/v) glycerol) at 2 ml/min. Most of the protein does not bind the column but a portion of the protein and DAGAT activity bind the column. The column is washed with 5 column volumes of equilibration buffer then bound protein and DAGAT activity are eluted over a 120 ml linear gradient of 75–500 mM KCl in Buffer C at 2 ml/min. Fractions are assayed immediately and active fractions are pooled and concentrated 8 fold by ultrafiltration using a pressurized stirred cell (Amicon) fitted with a YM-30 membrane. The concentrate is loaded onto a hydroxylapatite column (approximately 1.0 cm×26 cm, Bio-Gel HT, Bio-Rad, Hercules. Calif.) equilibrated with 500 mM KCl in Buffer C at 0.5 ml/min and the column is washed with 40 ml of equilibration buffer. Since DAGAT activity is found in the flow-through and wash, bound proteins are not eluted in this experiment. Active fractions are pooled and diluted 1:3.3 to reduce the KCl concentration from 500 to 150 mM. The diluted sample is applied to a Heparin column (0.55×4.7 cm) equilibrated with 150 mM KCl in Buffer C at 0.5 ml/min. The column is washed with 5 volumes of equilibration buffer and bound protein is eluted in a 10 μl linear gradient of 150–500 mM KCl in Buffer C at 0.25 ml/min. After the gradient the column is washed with 15 volumes of 500 mM KCl in Buffer C at 0.25 ml/min. DAGAT activity elutes in two peaks, one during the gradient and one during the 500 mM KCl wash after the gradient. Fractions over the column profile, including those containing DAGAT activity, are concentrated by precipitation as in Example 8. The precipitated samples are separated by gradient gel SDS-PAGE and the gel is stained with silver as in Example 3. The pattern of bands eluting from the column are compared, fraction by fraction, to the respective DAGAT activity profile (FIG. 8A). Examination of the stained protein bands indicate a protein in the size range of about 36 kDa to about 37 kDa correlates best with DAGAT activity found in the peak eluting during the 500 mM KCl wash (FIG. 8B). Based on this information, the 36 to about 37 kDa protein bands excised from the two gels described in Example 6C are sent for in-gel digestion and protein sequencing.

Example 7

Scale-up of the Purification Protocol for Identifying DAGAT Protein Candidates from *Mortierella ramanniana*

The purification protocol described in Example 6D indicates two possible forms of DAGAT may be present in this preparation, however, there is insufficient protein at the final step of purification to proceed with protein sequencing therefore a scale-up of the protocol was performed.

A. Scale-up Through Yellow 86-Agarose

Figure 9:
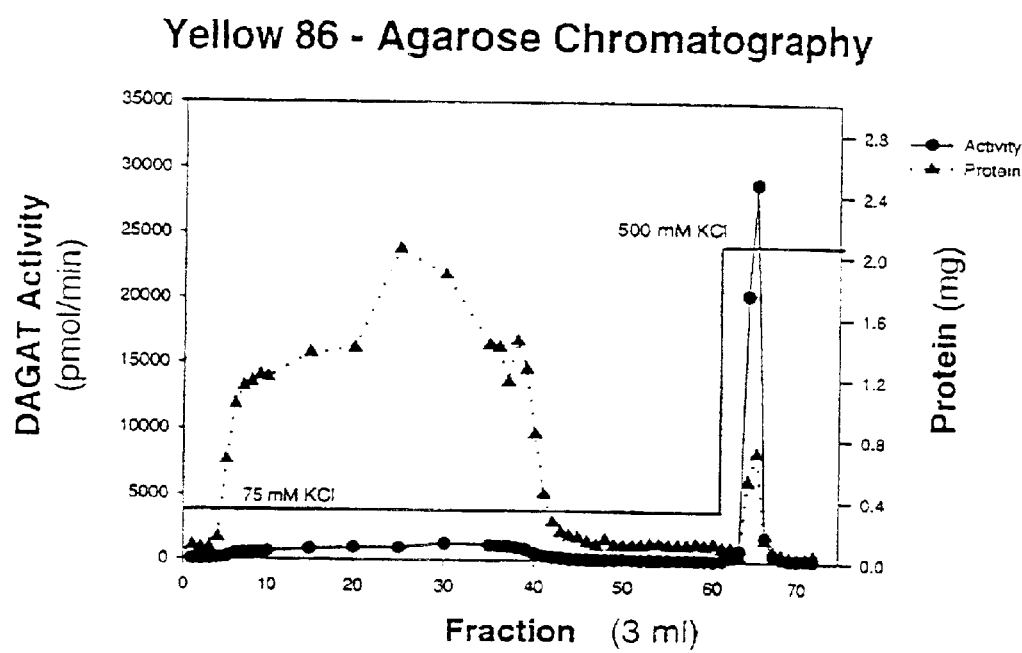
FIG. 9 shows the results of chromatography of *Mortierella ramanniana* DAGAT activity on a Yellow 86-Agarose column.

The Triton X-100 extract described in Example 6A and 6B is thawed and applied to a Yellow 86-Agarose column (2.5 cm×6.4 cm) equilibrated with 75 mM KCl in Buffer C (10 mM potassium phosphate (pH 7.0), 0.1% (w/v) Tx-100, 10% (w/v) glycerol) at 2 ml/min. Most of the protein does not bind the column but a portion of the protein and DAGAT activity bind the column. The column is washed with 5 column volumes of equilibration buffer then bound protein and DAGAT activity are eluted with 500 mM KCl in Buffer C at 2 ml/min (FIG. 9). The DAGAT activity is stable to freeze/thaw at this stage of purification so eluted fractions are typically stored at −70° C. at this stage. Eluted fractions are also assayed for DAGAT activity according to Example 1B.

B. Chromatography on Hydroxylapatite

Figure 10A:
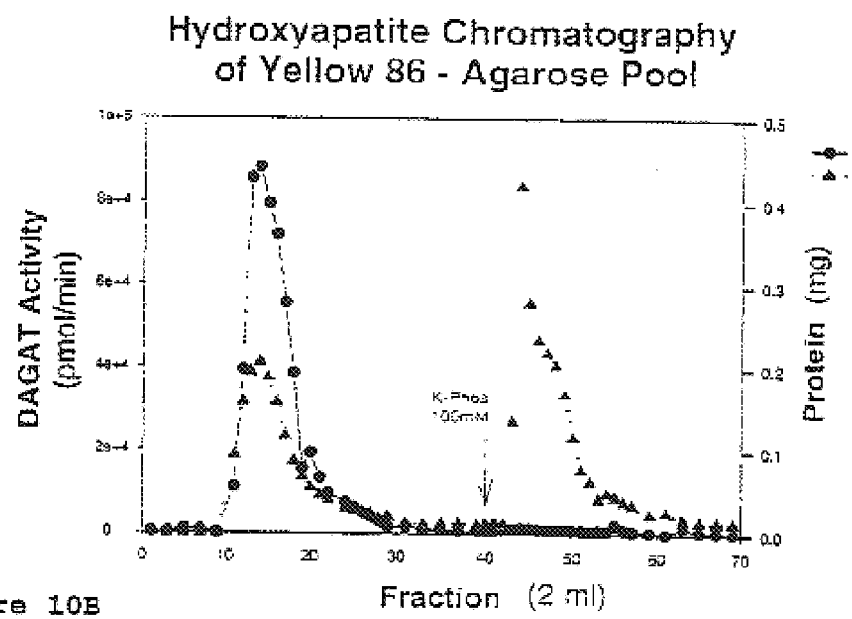
FIG. 10A shows the results of chromatography of *Mortierella ramanniana* DAGAT activity pooled from four Yellow 86-Agarose columns on a column of hydroxylapatite (Bio-Gel HT).
Figure 10B:
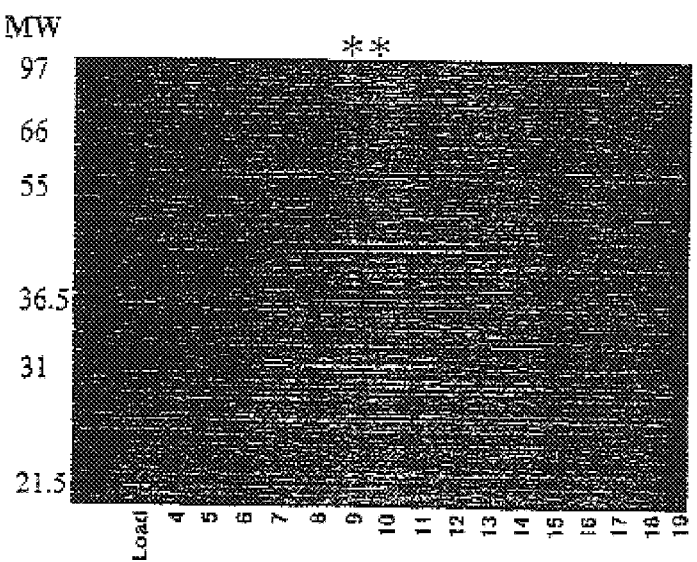
FIG. 10B shows SDS-PAGE analyses of fractions from the hydroxylapatite column. Protein bands are detected by silver stain.

After four preparations are purified through Yellow 86-Agarose, the most active fractions are pooled, concentrated 12–14 fold by ultrafiltration (Amicon stirred cell, YM-30 membrane) and applied (0.5 ml/min) to a hydroxylapatite column (Bio-Gel HT, Bio-Rad, 1 cm×25.5 cm) equilibrated with 500 mM KCl in Buffer C. Concentration of the sample is performed prior to HA chromatography in order to reduce the time required for loading of the sample. DAGAT activity flows through the column whereas the majority of the remaining proteins bind the column and are separated. The column is washed with 3 volumes of equilibration buffer. Bound proteins are eluted with 100 mM dipotassium phosphate and 500 mM KCl in Buffer C at 0.5 ml/min (FIG. 10A). A portion of the fractions containing the DAGAT activity peak are run on gradient gel SDS-PAGE as described in Example 3. The proteins are stained with silver and the pattern of the bands are compared, fraction by fraction, to the activity profile (FIG. 10B). Several DAGAT protein candidates correlate with activity. In particular, attention is called to bands migrating at positions corresponding approximately to 36.5 kD, 36 kD, 35 kDa, 34 kD, 33 kD and 31 kD. Again, there does not appear to be a candidate protein in the region of 53 kD previously described that correlates with activity.

C. Chromatography on Heparin

Figure 11A:
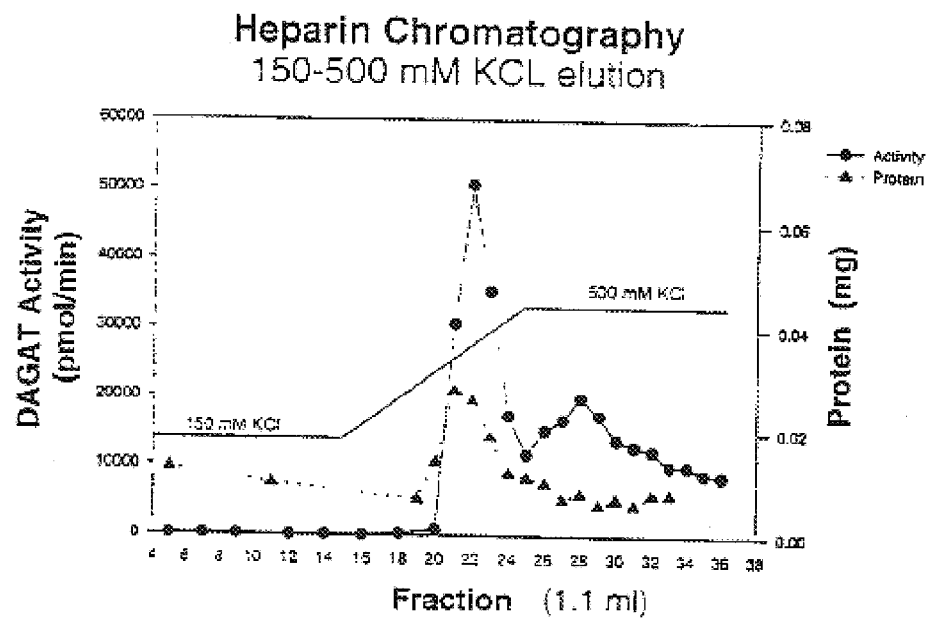
FIG. 11A shows the results of chromatography of *Mortierella ramanniana* DAGAT activity from the hydroxylapatite column on a column of Heparin Sepharose CL6B.
Figure 11B:
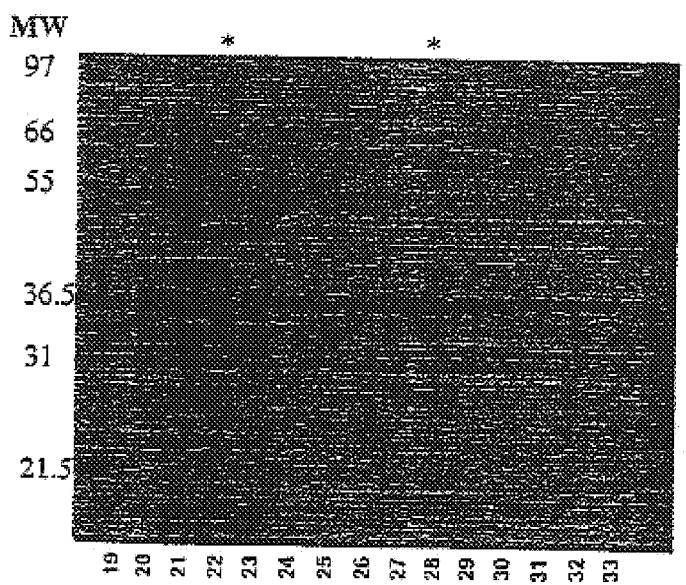
FIG. 11B shows SDS-PAGE analyses of fractions from the Heparin Sepharose CL6B column. Protein bands are detected by Coomassie Blue stain.

Following hydroxylapatite chromatography, DAGAT activity is not stable to freeze/thaw so fractions are assayed immediately and active fractions are pooled for further chromatography. The pool is diluted with Buffer C to lower the KCl concentration from 500 mM to 150 mM KCl. The diluted pool is loaded on a Heparin column (0.55×4.7 cm) equilibrated with 150 mM KCl in Buffer C. Protein and DAGAT activity are eluted during a 10 ml gradient of 150–500 mM KCl in Buffer C followed by a 10 ml wash with 500 mM KCl in Buffer C. DAGAT activity elutes in two peaks, a sharp peak is found during the KCl gradient and another broader peak during the wash (FIG. 11A). A portion of the fractions containing the DAGAT activity peak are run on gradient gel SDS-PAGE and are silver-stained. The pattern of bands eluting from the column is compared, fraction by fraction, to the respective DAGAT activity profile. Examination of the stained protein bands indicate a protein at 36 kDa correlates best with DAGAT activity found in the broad peak (FIG. 11B). Several proteins (of approximately 36.5 kDa, 35 kDa, 34 kDa) are associated with activity found in the sharp peak. The candidates at about 33 kDa and about 31 kDa do not appear to correlate with DAGAT activity. Table 1 demonstrates the fold purification from the 1500×g fraction through Heparin.

TABLE 1

| Fraction | Protein mg | Activity nmol/min | Specific activity nmol/min/mg | Fold Purification |
|---|---|---|---|---|
| 1500 g | 585.3 | 304.5 | 0.5 | 1.0 |
| LBF/Tx-100 | 67.4 | 714.8 | 10.6 | 20.4 |
| TX-100 extract | 29.4 | 517.3 | 17.6 | 33.8 |
| Yellow Load | 15.9 | 364.7 | 22.9 | 44.1 |
| Yellow Ft/wash | nd | 179.8 | nd | nd |
| Yellow Eluted | 0.4 | 169.5 | 440.3 | 846.2 |
| Four Yellow columns were pooled for further chromatography | | | | |
| Yellow Pool | 1.54 | 437.1 | 283.9 | 545.5 |
| HA Pool | 0.56 | 340.2 | 607.6 | 1167.6 |
| Heparin | 0.20 | 264.6 | 1323.0 | 2646.0 |
| Heparin#22 MR-2 | 0.026 | 51.0 | 1961.5 | 3769.5 |
| Heparin#28 MR-1 | 0.0076 | 20.0 | 2631.6 | 5057.2 |

The four candidates identified (at about 36.5 kDa, 36 kDa, 35 kDa and 34 kDa) are prepared for in-gel digestion by precipitating fractions from the Heparin column as described in Example 8B and separated by gradient gel SDS-PAGE as described in Example 8C. In this manner, peptide maps are obtained from each of the DAGAT candidates and individual peptides are selected for protein sequencing.

D. Chromatography on Yellow 86-Agarose with Gradient Elution

Figure 12A:
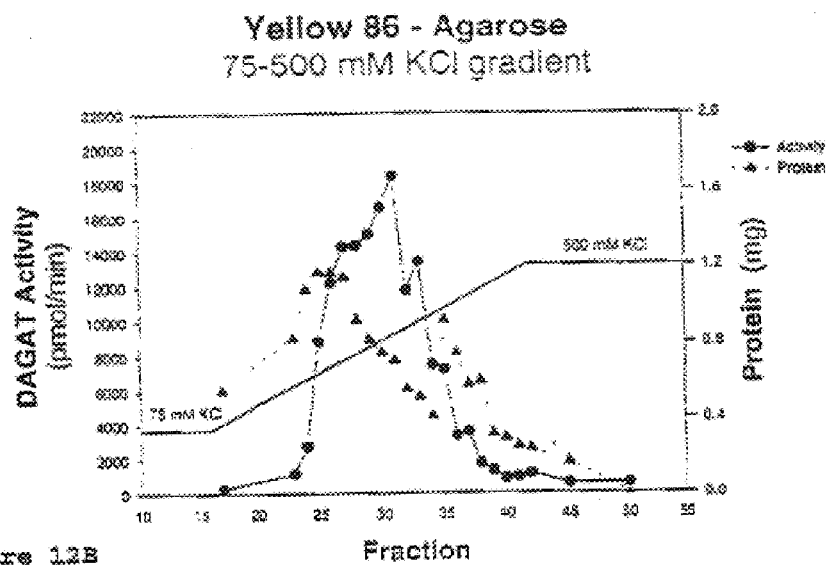
FIG. 12A shows the results of chromatography of *Mortierella ramanniana* DAGAT activity from the first activity peak of the Heparin Sepharose CL6B column chromatographed on a Yellow 86-Agarose column where protein was eluted during a gradient of 75–150 mM KCl.
Figure 12B:
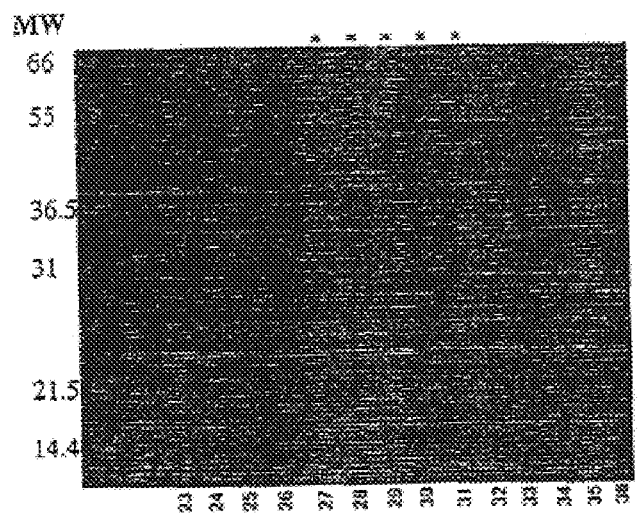
FIG. 12B shows SDS-PAGE analyses of fractions from the Yellow 86-Agarose column. Protein bands are detected by Coomassie Blue stain.

In order to examine another purification protocol DAGAT is purified through hydroxylapatite as described in Example 6A, diluted to 75 mM KCl and then applied to a Yellow 86-Agarose column (1.3×6.3 cm) equilibrated with 75 mM KCl in Buffer C. The column is washed with 25 ml of equilibration buffer and bound proteins are eluted over a 40 ml gradient of 75–500 mM KCl in Buffer C. Fractions are assayed for DAGAT activity as in Example 1B. DAGAT activity appears as a single peak in the middle of the gradient. Fractions containing DAGAT activity are concentrated by precipitation as in Example 8B and are separated by SDS-PAGE as in Example 8C, The pattern of bands eluting from the column are compared, fraction by fraction, to the respective DAGAT activity profile (FIG. 12A). The 34 kDa protein candidate elutes early in the gradient and does not appear to correlate with DAGAT activity (FIG. 12B). Three remaining protein candidates (of about 36.5 kDa, 36 kDa, and 35 kDa, designated Mr21, Mr22, Mr23, respectively) correlate with DAGAT activity.

Example 8

Preparation of Protein for In-Gel Digestion

After a protein candidate has been identified, it is necessary to prepare sufficient amounts for sequencing. Protein sequencing can be performed using a wide variety of methods known in the art. One technique involves digestion of the protein, using enzymes such as trypsin, while still in an SDS-polyacrylamide gel. Several commercial enterprises have established protocols for obtaining peptides in this manner. Following the generation of peptides, standard techniques are employed to separate and sequence them.

In order to gel-purify a protein candidate, it is often necessary to concentrate the liquid sample first so that it can be loaded on the gel. Samples containing high amounts of detergent may pose special problems. Depending on the micelle size of the detergent, it may concentrate during ultrafiltration and pose problems during electrophoresis. An alternative method of concentrating the protein sample must then be employed.

A. Preparation of Samples for SDS-PAGE by Concentration

Fractions can be concentrated in a pressure cell fitted with a membrane of the appropriate molecular weight retention limit. Alternatively, the sample may be concentrated using filtration by centrifugation in individual units, for example a product such as Centricon-30 (Amicon, Inc., Beverly, Mass.), to volumes of approximately 50 µl. Following concentration, samples can be treated with a loading buffer, for example, Laemmli.

B. Preparation of Samples for SDS-PAGE by Precipitation

Sometimes it is desirable to concentrate samples by precipitation. This can be achieved using acid and/or acetone. A typical protocol would be to add trichloroacetic acid (TCA) from a concentrated stock (40%–50% (w/v)) to a final concentration of 7–10% (w/v). After about 10 minutes on ice the samples are centrifuged (12,000×g, 15 minutes at 4 C.) to pellet the precipitated protein. The supernatants are removed and in order to remove the precipitated detergent, the pellets are washed with ice cold acetone and centrifuged again. Precipitates can be resuspended with a sample loading buffer (i.e. Laemmli or SDS-PAGE sample buffer as in Example 3). SDS-PAGE may be performed using gels cast in the laboratory, as described in Example 3 or from gels prepared by commercial sources.

C. SDS-Page

Heating of the samples prior to loading the gel may or may not be performed. It has been observed that some membrane proteins have a tendency to aggregate upon heating. In this case, samples are generally applied to the gel after sitting at room temperature for 15 minutes. Acrylamide gels may be purchased commercially or prepared in the laboratory. One protocol for preparing 10–13% (w/v) acrylamide gels is described in Example 3. Following electrophoresis, the gel can be stained with 0.1% (w/v) Coomassie Blue in 50% (v/v) methanol, 10% (v/v) acetic acid then destained. Destaining can be accomplished with the use of a commercial product, such as Gel-Clear (Novex, San Diego, Calif.) or in 50% (v/v) methanol, 10% (v/v) acetic acid. Protein candidates can then be excised from the gel and sent for in-gel digestion with or without further destaining.

Example 9

Determination of Amino Acid Sequence

Commercial facilities have been established which provide protein sequencing as a service. Among the techniques which are available, the generation of peptides by in-gel digestion using an endopeptidase, such as trypsin, followed by HPLC purification, has proved the most useful. N-terminal sequencing on PVDF, and to a lesser degree the generation of peptides by limited cyanogen bromide treatment of the PVDF proteins, has also proved successful. Procedures for in-gel digestion may include amino acid analysis of a portion (10–15%) of the gel slice for quantitation and amino acid composition, digestion of the protein with one of the proteolytic enzymes (trypsin or lysyl endopeptidase), and fractionation of the products by reverse phase HPLC. Absorbance peaks may be selected from the HPLC run and subjected to laser desorption mass spectrometry to determine the presence, amount, and mass of the peptide prior to protein sequencing. The longest peptides are selected for microsequencing. In particular, DAGAT candidates are gel purified and sent to Argo Bioanalytica (a commercial service) for in-gel digestion and microsequencing.

Example 10

Amino Acid Sequence of Trypsin Generated Peptides

Amino acid sequence of peptides generated from the approximately 36 kDa protein, also designated MR1, (see Examples 6C and 6D) by trypsin digestion as described in Example 9, are as follows (the first two digits of the sequence number designates the Mr bands described in examples 6C and 7C):

| sequence # | amino acid sequence | SEQ ID NO: |
|---|---|---|
| 19-138 | ELHDSYMAV | 1 |
| 19-169 | kIqHALgFTMplFhgr | 2 |
| 19-181 | HPIYTiv | 3 |
| 18-146 | NAAwpk | 4 |
| 18-151 | VKELEFVE | 5 |
| 18-159-1 | FGF | 6 |
| 18-159-2 | yxhDayphave | 7 |
| 18-164 | ELHDSYMHAVQDLYDR | 8 |
| 18-208-1 | GVFNYDFGLLPHR | 9 |
| 18-208-2 | xlagifpa | 10 |
| 18-219-1 | IAVQTGAGLVPTLsF | 11 |
| 18-219-2 | sIAIVVgSASEsINA | 12 |

-continued

| sequence # | amino acid sequence | SEQ ID NO: |
|---|---|---|
| 18-219-3 | gffNYDFxxl | 13 |
| 22-158 | ELHDSYMHAV | 14 |

Amino acid sequence of peptides generated from the approximately 36.5 kDa protein, also designated MR2, (see Example 7B) by trypsin digestion as described in Example 9, are as follows:

| sequence # | amino acid sequence | SEQ ID NO: |
|---|---|---|
| 21-134 | VHWAPLR | 15 |
| 21-149-1 | KLPLFk | 16 |
| 21-149-2 | VDIDxAPpR | 17 |
| 21-160-1 | ITGFTVPHAH | 18 |
| 21-160-2 | ELHDSHMLxV | 19 |
| 21-213 | GIFNYNAGFIPFR | 20 |
| 21-178 | hPIYTIVGKpipv | 21 |
| 21-101 | gsCEAILR | 22 |
| 21-221 | hPIVTVVGKPIAVpLLAegeteppse | 23 |
| 21-197 | sRDsTPVITEHKQPMeQvqvtalldhipv | 24 |

The amino acid sequence is represented using the one letter code. Amino acids represented by lower case letters represent residues which were identified with a lesser degree of confidence. The peptide map from the 35 kDa candidate, Mr23 in Example 7C, substantially similar to the peptide map of the 36.5 candidate, Mr21 in Example 7C.

The amino acid sequences in the peptides above are compared to known protein sequences in public and proprietary data bases. No significant homology is found between the DAGAT peptides and any sequence encoding an enzyme of known function including any portion of glyceraldehyde 3-phosphate (GAP) dehydrogenase which is known to migrate at about 36 kDa by SDS-PAGE.

Example 11

Identification of *Mortierella ramanniana* DAGAT Nucleic Acid Sequences

In general, for use as polymerase chain reaction (PCR) primers from single stranded DNA template reverse-transcribed from mRNA, oligonucleotides containing the sense orientation sequence corresponding to DAGAT peptide encoding sequences are prepared. For the "reverse" reaction for amplification of the encoding DNA strand, an oligonucleotide may be designed which contains sequence complementary to DAGAT peptide encoding sequence.

Alternatively, an oligonucleotide may be designed to be identical to a portion of a primer used to prepare DNA template for PCR. This oligonucleotide may be used as either the "forward" or "reverse" primer as described above.

Where the DAGAT peptide sequences contain amino acids which may be encoded by a number of different codons, the forward or reverse primers may be "degenerate" oligonucleotides, i.e. containing a mixture of all or some of the possible encoding sequences for a particular peptide region. To reduce the number of different oligonucleotides present in such a mixture, it is preferable to select peptide regions which have the least number of possible encoding sequences when preparing the synthetic oligonucleotide for PCR primers.

A. Identification of DAGAT MR1

To identify the nucleic acid sequence for *Mortierella ramanniana* DAGAT MR1, peptide 18-151 is used to design degenerate primer 5'-CACTGCAGACRAAYTCNARYTCYTTNAC-3' (SEQ ID NO:25), peptide 18-208-1 is used to design primers 5'-CCAAGCTTGGNGTNTTYAAYTAYGAYTTYG-3' (SEQ ID NO:26) and 5'-CACTGCAGCRAARTCRTARTTRAANACNCC-3' (SEQ ID NO:27), peptide 18-164 is used to design primer 5'-CACTGCAGCYTGNACNGCNGCRTGCATRTA-3' (SEQ ID NO:28), peptide 18-219-1 is used to design primer 5'-CCAAGCTTATHGCNGTNCARACNGGNGC-3' (SEQ ID NO:29), peptide 19-181 is used to design primers 5'-CCAAGCTTAARCAYCCNATHTAYACNAT-3' (SEQ ID NO:30) and 5'-CACTGCAGACDATNGTRTADATNGGRTG-3' (SEQ ID NO:31), peptide 19-169 is used to design primers 5'-CCAAGCTTGCNYTNGGNTTYACNATGCC-3' (SEQ ID NO:32), 5'-CCAAGCTTTTYACNATGCCNYTNTTYCA-3' (SEQ ID NO:33) and 5'-CACTGCAGAARTGRAANARNGGCATNGT-3' (SEQ ID NO:34).

DNA fragments obtained by PCR are analyzed for nucleic acid sequence encoding amino acid sequence found in the peptides in Example 10. To obtain the entire coding region corresponding to the *Mortierella ramanniana* DAGAT MR1 protein, synthetic oligo-nucleotide primers are designed to amplify the 5' and 3' ends of partial cDNA clones containing MR1 sequences. Primers are designed according to the *Mortierella ramanniana* DAGAT MR1 sequence and are used in Rapid Amplification of cDNA Ends (RACE) reactions (Frohman et al. (1988) *Proc. Natl. Acad. Sci. USA* 85:8998–9002). Amplification of flanking sequences from cDNA clones are performed using the Marathon cDNA Amplification kit (Clontech, Calif.). For example, PCR reactions can be performed with 3' RACE primer 5'-GGTTTGCTCCCCCATCGCCATCCTATC-3' (SEQ ID NO:35) and 5' RACE primer 5'-GATAGGATGGCGATGGGGGAGCAAACC-3' (SEQ ID NO:36). In this manner the complete MR1 encoding sequence of 1065 nucleotides is determined (SEQ ID NO:37). The predicted protein sequence for the MR1 DAGAT is also determined (SEQ ID NO:38) DAGAT nucleic acid sequences are obtained which may be analyzed for nucleic acid sequence and used for expression of DAGAT in various hosts, both procaryotic and eucaryotic.

The primers 5-AATTCGCGGCCGCATGGCCAGCAAGGATCAACATTTACAGC-3' (SEQ ID NO:39)and 5'-TGCTGCAGCTATTCGACGAATTCTAGTTCTTTTACCCGATCC-3' (SEQ ID NO:40) are used to PCR amplify the open reading frame (ORF) from *Mortierella ramanniana* Marathon cDNA library made according to the manufacturer's protocol Clonetech). These primers introduce NotI and Pst1 restriction sites at the 5' and 3' ends of the ORF, respectively. The PCR product is cloned into plasmid pCR2.1 according to the manufacturer's protocol (Invitrogen) to yield plasmid pCGN8707. Double stranded DNA sequence is obtained to verify that no errors are introduced by PCR amplification. For expression of the *M. ramanniana* DAGAT MR1 protein in insect cells using a baculovirus expression system, the NotI-PstI fragment of pCGN8707 is cloned into NotI-PstI digested plasmid pFASTBAC1 (Gibco), and the resultant plasmid, pCGN8708, is transformed into *E. coli* DH10BAC (Gibco). The bacmid DNA is used to transfect insect cells. For expression of the *Mortierella ramanniana* DAGAT MR1 sequence in plants, the NotI-PstI fragment of pCGN8708 is cloned into NotI-PstI digested binary vector pCGN8622 to yield plasmid pCGN8709 under control of a napin promotor. Plasmid pCGN8709 is introduced in *Agrobacterium tumefaciens* EHA105.

B. Identification of DAGAT MR-2

To identify the nucleic acid sequence for *Mortierella ramanniana* DAGAT MR2, peptide 21-221 is used to design degenerate primer 5'-GGCACNGCDATN GGYTTNCCNAC-3' (SEQ ID NO:41) and peptide 21-218 is used to design primer 5'-CCNGCRTTRT ARTTRAADATNCC-3' (SEQ ID NO:42). These are used in a nested PCR as antisense primers in Rapid Amplification of cDNA Ends (RACE) reactions (Frohman et al. (1988) *Proc. Natl. Acad. Sci. USA* 85:8998–9002) using a cDNA library constructed with the Marathon cDNA Amplification kit (Clontech) according to the manufacturers instructions.

RACE amplification of the 5' region corresponding to the *Mortierella ramanniana* DAGAT MR2 protein is performed with primer 5'-TGCCTAGTGACATCATGAAATCTCG-3' (SEQ ID NO:43) using a cDNA library constructed with the Marathon cDNA Amplification kit (Clontech) according to the manufacturers instructions. In this manner the partial encoding sequence of nucleotides is determined (SEQ ID NO:44). A partial amino acid sequence for the MR2 protein is also predicted (SEQ ID NO:45).

Those skilled in the art will recognize that further RACE reactions will lead to the cloning the complete nucleic acid sequence which may be used for expression of DAGAT in various hosts, both procaryotic and eucaryotic.

C. Comparison of MR1 and MR2 Sequences

Analysis of the protein sequence alignments between the protein sequences of the *Mortierella ramanniana* DAGAT sequences MR1 (SEQ ID NO:38) and MR2 (SEQ ID NO:45) (FIG. 13) shows that they share 55% similarity.

Example 12

Identification of DAGAT Related Sequences

Since plant DAGATs are unknown in the art, the *Mortierella ramanniana* DAGAT nucleic acid and protein sequences are used to search public and proprietary EST databases as well as public genomic databases to identify other DAGAT-like sequences.

Three EST sequences can be identified by tblastn in the maize proprietary database, which are assembled into two contigs using the GCG assembly program(SEQ ID NO:46–47). One EST can be identified in each of the *Brassica napus* (SEQ ID NO:48) and soybean proprietary databases (SEQ ID NO:49). Two EST sequences can be identified in *Arabidopsis thaliana* proprietary databases (SEQ ID NO:50–51), and one proprietary genomic sequence (SEQ ID NO:52).

The MR1 protein sequence is used to search proprietary mouse and human databases. Results of this search identified approximately 45 EST sequences from Human. which are assembled into 5 contigs using the GCG assembly program (SEQ ID NO:53–57) and 12 from mouse, which are assembled into 3 contigs using the GCG assembly program (SEQ ID NO:58–60). Searches of proprietary *Aspergillus fumigatus* (SEQ ID NO:61 and 62), *Aspergillus oraceus* (SEQ ID NO:63), *Candida albicans* (SEQ ID NO:64), *Fusarium graminearum* (SEQ ID NO:65), *Mortierella alpina* (SEQ ID NO:66), and *Schizochytrium aggregatum* (SEQ ID NO:67), yield additional EST sequences.

Along with these EST sequences, database searches of the public predicted proteins from the genomic and amino acid sequence databases of *C. elegans* yield four similar sequences, W01A11.2 (SEQ ID NO:68), K07B1.4 (SEQ ID NO:69), F59A1.10 (SEQ ID NO:70), well as the protein sequence y53G8B_93.B (SEQ ID NO:71). Similar searches of the public *S. cerevisae* predicted protein database yields one sequence, YOR245c (SEQ ID NO:72).

Total RNA was collected from these two organisms, and a 1$^{st}$ strand cDNA library was created using the Marathon cDNA library kit (Clontech.) The primers 5'-GCGCGGCCGCCTGCAGTCACTGGAAGATGAG-3' (SEQ ID NO:73) and 5'-GCGCGGCCGCATGAG ACTCCGGCTGAGCTCG-3' (SEQ ID NO:74) are used to PCR amplify the W01A11.2 from the *C. elegans* cDNA library. Primers 5'-GAGCGGCCGCATGCCACA TCTACTAGGAGTTGA-3' (SEQ ID NO:75) and 5'-CGGCGGCCGCCTGCAGTTAATTGATAACAAG TTGT-3' (SEQ ID NO:76) are used to PCR amplify the CEK07B1.42 from the *C. elegans* cDNA library. 5'-GCGCGGCCGCATGCTAAACTACCAAATTCACA-3' (SEQ ID NO:77) and 5'-TGGCGGCCGCCTGCAGTCAC TGAAAAACGAGCC-3' (SEQ ID NO:78) are used to PCR amplify the CEF59A1.102 from the *C. elegans* cDNA library. Primers 5'-CAGCGGCCGCATGTCA GGAACATTC-3' (SEQ ID NO:79) and 5'-CACTGCAGTTACCCAACTATCTTCAA-3' (SEQ ID NO:80) are used to PCR amplify the YOR245C from the *S. cerevisae* cDNA library. The PCR products were cloned into pCR2.1 TOPO according to the manufacturer's protocol (Invitrogen), and these sequences were verified.

Example 13

Sequence Comparisons

Sequence alignments between DAGAT-like sequences from several different sources are compared to identify the similarity between the sequences.

The longer sequences are aligned using the Clustal Algorithm in DNASTAR. The following percent similarity values are obtained as compared to the MR1 sequence:

| | |
|---|---|
| ATgC-A1X01ds10429d10a1 | 19.8% |
| ATLIB22-029-Q1-E1-G7 | 19.0% |
| ATLIB24-124-Q1-E1-E2 | 16.8% |
| BNLIB3034-036-Q1-E1-C3 | 18.2% |
| CEF59A1.10 | 37.1% |
| CEK07B1.4 | 36.3% |
| CEW01A11.2 | 39.0% |
| HS4371967H1CON | 42.0% |
| HS4818474H1 | 25.9% |
| MALIB26-037-Q1-E1-D8 | 41.6% |
| MMg2813274 | 32.4% |
| MMg2892216 | 30.2% |
| MMg2989686 | 38.7% |
| MR2 | 53.9% |
| ZMLIB3136-059-Q1-K1-F10 | 14.6% |
| GM701121562H1 | 15.2% |

The protein sequences that contain a conserved region corresponding to bases 355 to 796 of MR1 are aligned and truncated to this region, the following percent similarity is achieved.

| | |
|---|---|
| AF804547551F1 | 35.1% |
| ATgC-A1X01ds10429d10a1 | 22.3% |
| ATLIB22-029-Q1-E1-G7 | 20.0% |
| ATLIB24-124-Q1-E1-E2 | 18.8% |
| BNLIB3034-036-Q1-E1-C3 | 19.0% |
| CA803535474F1 | 33.6% |
| CEF59A1.10 | 44.9% |
| CEK07B1.4 | 46.3% |
| CEW01A11.2 | 50.3% |
| GM701121562H1 | 25.4% |
| HS4371967H1CON | 52.4% |
| MALIB26-037-Q1-E1-D8 | 55.6% |
| MMg2989686 | 49.7% |
| MR2 | 60.3% |
| SCYOR245c | 42.4% |
| ZMLIB3136-059-Q1-K1-F10 | 26.3% |

Example 14

Expression Constructs

A. Baculovirus Expression Constructs

Constructs are prepared to direct the expression of the *M. ramanniana* DAGAT protein in cultured insect cells. The NotI-PstI fragment of pCGN8707 is cloned into NotI-PstI digested plasmid pFASTBAC1 (Gibco), and the resultant plasmid, pCGN8708, is transformed into *E. coli* DH10BAC (Gibco). The bacmid DNA is used to transfect insect cells.

B. Plant Expression Construct Preparation

Constructs which provide for expression of DAGAT sequences in plant cells may be prepared as follows.

A plasmid containing the napin cassette derived from pCGN3223 (described in U.S. Pat. No. 5,639,790, the entirety of which is incorporated herein by reference) is modified to make it more useful for cloning large DNA fragments containing multiple restriction sites, and to allow the cloning of multiple napin fusion genes into plant binary transformation vectors. An adapter comprised of the self annealed oligonucleotide of sequence 5'-CGCGATTT AAATGGCGCGCCCTGCAGGCGGCCGCCTGCAGGG GCGCCATTTAAAT-3' (SEQ ID NO:81) is ligated into the cloning vectorpBC SK+ (Stratagene) after digestion with the restriction endonuclease BssHII to construct vector pCGN7765. Plasmids pCGN3223 and pCGN7765 are digested with NotI and ligated together. The resultant vector, pCGN7770, contains the pCGN7765 backbone with the napin seed-specific expression cassette from pCGN3223.

The plasmid pCGN8618 is constructed by ligating oligonucleotides 5'-TCGAGGATCCGCGGCCGCAAGCTTCCTGCAGG-3' (SEQ ID NO:82) and 5'-TCGACCTGCAGGAAGC TTGCGGCCGCGGATCC-3' (SEQ ID NO:83) into SalI/XhoI-digested pCGN7770. A fragment containing the napin promoter, polylinker and napin 3' region is excised from pCGN8618 by digestion with Asp718I; the fragment is blunt-ended by filling in the 5' overhangs with Klenow fragment then ligated into pCGN5139 that has been digested with Asp718I and HindIII and blunt-ended by filling in the 5' overhangs with Klenow fragment. A plasmid containing the insert oriented so that the napin promoter is closest to the blunted Asp718I site of pCGN5139 and the napin 3' is closest to the blunted HindIII site is subjected to sequence analysis to confirm both the insert orientation and the integrity of cloning junctions. The resulting plasmid is designated pCGN8622.

The NotI/PstI fragment of pCGN8708 containing the entire DAGAT encoding region is ligated into NotI/PstI digested pCGN8622 to provide the expression construct pCGN8709 having the *Mortierella ramanniana* DAGAT encoding sequence positioned for transcription of the sense sequence under regulation of the napin promoter.

In addition, the MR1 nucleic acid sequence is resynthesized (SEQ ID NO:84) for plant preferred codon usage and used to produce expression constructs for transformation into host plant cells.

Binary vector constructs are transformed into Agrobacterium cells, such as of strain EHA105 (Hood et al., *Transgenic Research* (1993) 2: 208–218), by the method of Holsters et al. (*Mol. Gen. Genet.* (1978) 163: 181–187) and used in plant transformation methods as described below.

Example 15

Expression of DAGATs in Insect Cell Culture

A baculovirus expression system is used to express the full length 36 kDa *Mortierella ramanniana* cDNA encoding a putative DAGAT in cultured insect cells.

The baculovirus expression construct pCGN8708 (see Example 14A) is transformed and expressed using the BAC-to-BAC Baculovirus Expression System (Gibco-BRL, Gaithersburg, Md.) according to the manufacturers directions, except harvesting of recombinant viruses was done 5 days post-transfection. The supernatant from the transfection mixture is used for generating virus stock which in turn is used for infecting Sf9 cells for use in the assay.

A. Assay of DAGAT Enzyme Activity in Insect Cell Culture Membranes

The transformed insect cells can be assayed for DAGAT or other acyltransferase activities using methods described herein. Insect cells are centrifuged and the resulting pelletted cells may either be used immediately or be stored at –70° C. for later analysis. Cells are resuspended in Medium I (100 mM Tricine/NaOH, pH 7.8, 10% (w/v) glycerol, 280 mM NaCl with: 0.1 $\mu$M Aprotinin, 1 $\mu$M Leupeptin, and 100 $\mu$M Pefabloc (all from Boehringer Mannheim, Germany) and lysed by sonication (2×10 sec). Cell walls and other debris are pelleted by centrifugation (14,000×g, 10 min, 4° C.). The supernatant is transfered to a new vial and membranes are pelleted by centrifugation (100,000×g, Ti 70.1 rotor, 46,000 rpm for 1 hour at 4° C.). Total membranes are resuspended in Medium I. DAGAT activity is assayed in a 0.1 ml reaction mixture containing 30 mM Tricine/NaOH, pH 7.8, 56 mM NaCl, 10 mM MgCl2, 0.2 mM 1,2-diolein in 2-methoxyethanol, 25 mM 1-$^{14}$C-palmitoyl-CoA (17,600dpm/nmole), and 0.2–30 mg of membrane protein. The 5 minute reaction is terminated by addition of a 1.5 ml solution of isopropanol:heptane:0.5M sulfuric acid (80:20:2, v/v/v). The reaction mixture may be stored at 4° C. or processed immediately as described in Example 1C.

Figure 14:
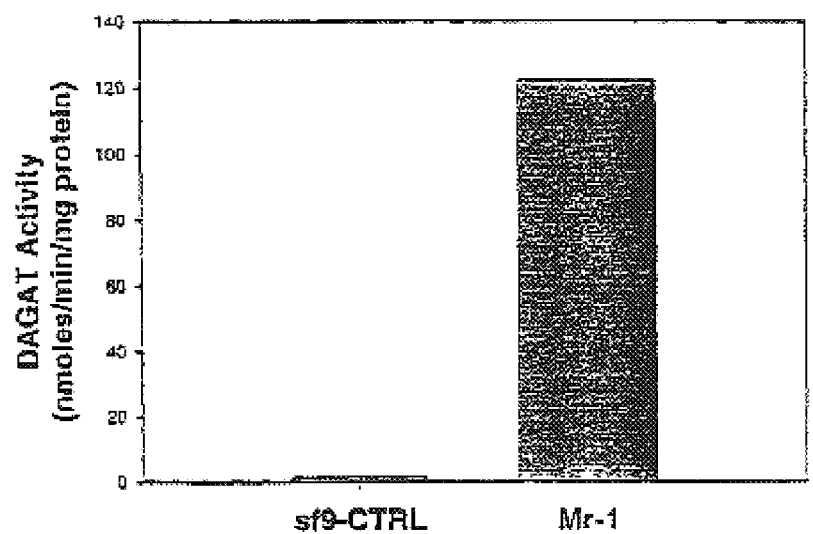
FIG. 14 shows DAGAT activity data on membranes isolated from insect cells infected with either an empty pFASTBAC vector or a pFASTBAC vector containing DNA sequence of the 36 kDa DAGAT sequence identified in *Mortierella ramanniana*.

The 36 kDa Mortierella candidate, when expressed in insect cells, demonstrates a 94-fold greater DAGAT activity than the control membranes isolated from insect cells infected with an empty vector (FIG. 14). The result of the DAGAT activity assay demonstrates that this *Mortierella ramanniana* DNA sequence encodes a protein with DAGAT activity.

Figure 15:
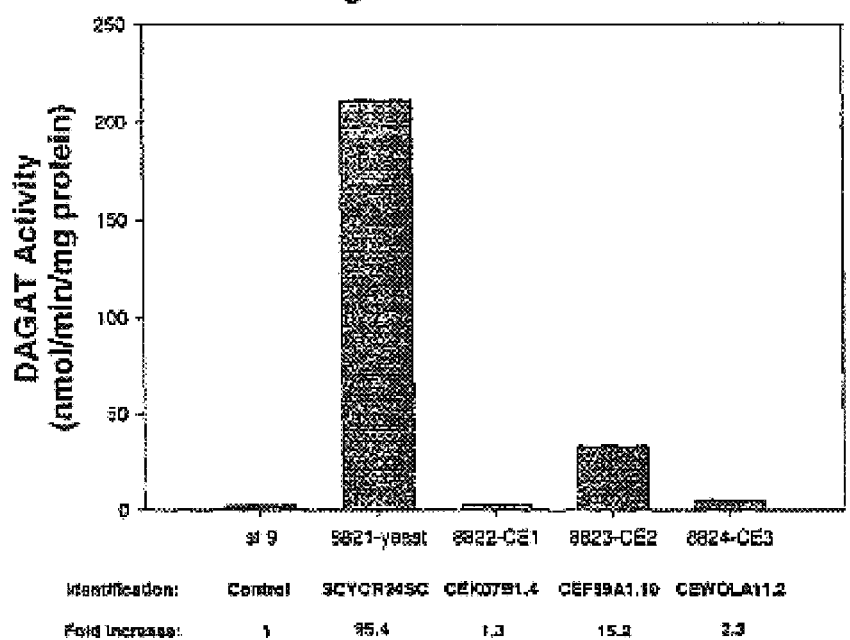
FIG. 15 shows DAGAT activity data on membranes isolated from insect cells infected with either an empty pFASTBAC vector or a pFASTBAC vector containing DNA sequence of DAGAT homologues from yeast and *C. elegans*.

Similarly, homologues of DAGAT identified from yeast (SCYOR245c) and *C. elegans* (CEK07B 1.4, CEF59A1.10, AND CEW0LA11.2) were also cloned into the pFAST-BAC1 (Gibco) vector to create baculoviral expression constructs pCGN8821, pCGN8822, pCGN8823, and pCGN8824, respectively. Results of DAGAT enzyme activity assays demonstrate significant increases in DAGAT enzyme activity over control vectors when expressed in insect cells (FIG. 15). For example, membranes isolated from insect cells infected with a vector for the expression of the yeast homologue sequence have greater than a 95 fold increase in DAGAT enzyme activity compared to control membranes isolated from insect cells infected with an empty vector (FIG. 15). Furthermore, membranes isolated from insect cells infected with a vector for the expression of the C. elegans homologue sequence (pCGN8823) have about a 15 fold increase in DAGAT enzyme activity (FIG. 15). Thus, additional DAGAT encoding sequences can now be readily identified using the sequences of the present invention.

B. Triacylglycerol Production in Insect Cell Culture

The transformed insect cells can be assayed for triacylglycerol, phosphotidyl choline or other lipid classes by methods described herein. An insect cell culture suspension is diluted to a standard optical density of 0.3 to 0.6 at an absorbance of 600 nm with culture medium. A sample of 4.5 ml of culture suspension in culture medium is added 200 µl glacial acetic acid, internal standards consisting of 12.5 µg c17:0 TAG and 25 µg c15:0 PC, and 10 ml of chloroform::methanol (1;1, v/v). After vortexing, the phases are separated by centrifugation (about 500×g, 5 min.). The lower, organic phase (OP1) is saved and the upper, aqueous phase is re-extracted with the lower, organic phase of a mixture of 200 µl glacial acetic acid, 10 ml of cholorform:methanol (1:1, v/v), and 4.5 ml water. The samples are again vortexed and centrifuged to separate the phases. The lower, organic phase is saved (OP2). The OPI is filtered through a 0.45 µm filter and the filter is rinsed with OP2. The filtrates are combined and concentrated under nitrogen gas to a final volume of 0.4 ml. Twenty-five percent of the final volume is spotted onto a hard layer silica gel GHL TLC plate with inorganic binder (Alltech Associates, Inc., Newark, Del.). The TLC plate is developed for 30 minutes in hexane:diethyl ether:acetic acid (80:20:2, v/v/v) containing 20 mg/100 ml propyl gallate as an antioxidant. After the plate is dried, it is sprayed with 0.001% primuline in 80% acetone and the lipid bands are identified under UV light. The TAG and phospholipid bands are scraped from the TLC plate into glass vials. The samples are methanolyzed in 2 ml 5% $H_2SO_4$ in methanol at 90° C. for 2 hours. After samples have cooled, 2 ml 0.9% NaCl and 0.50 ml hexane are added. After the sample is vortexed, centrifuged to separate the phases, and the top hexane layer is taken for analysis of fatty acid methyl esters (FAME) by gas chromatography using methods well known in the art.

Figure 16:
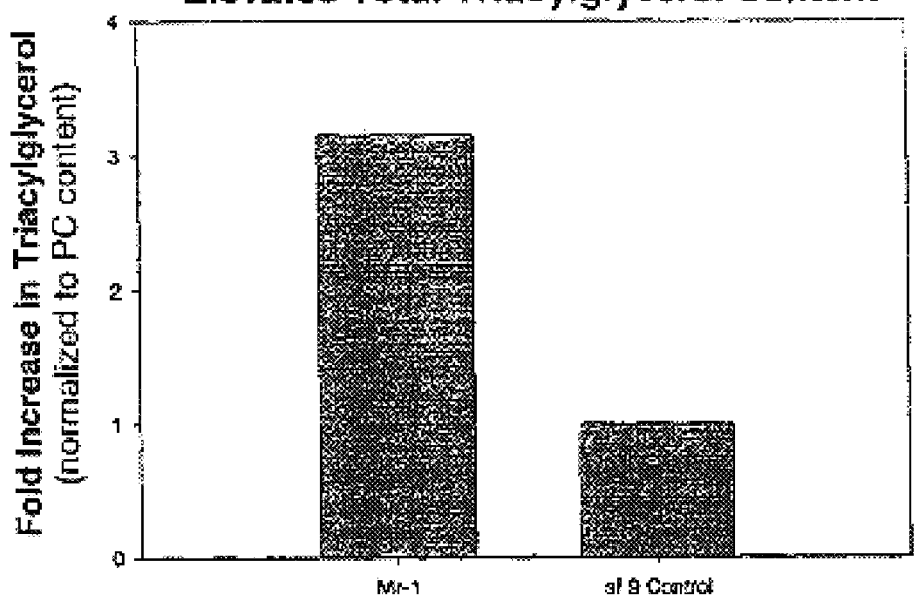
FIG. 16 shows the relative triacylglycerol content in insect cells infected with either an empty pFASTBAC vector or a pFASTBAC vector containing DNA sequence of the 36 kDa DAGAT sequence identified in *Mortierella ramanniana*.

The 36 kDa Mortierella candidate, when expressed in insect cells, demonstrates a 3.15 fold increase in triacylgycerol content compared to control culture of insect cells infected with an empty vector (FIG. 16). For comparison, the assays were normalized for cell phosolipid content. The result of the triacylglycerol analysis demonstrates that this-Mortierella ramanniana DNA sequence encodes a protein that leads to triacylglycerol production.

Example 16

Plant Transformation

A variety of methods have been developed to insert a DNA sequence of interest into the genome of a plant host to obtain the transcription or transcription and translation of the sequence to effect phenotypic changes.

Transgenic Brassica plants are obtained by Agrobacterium-mediated transformation as described by Radke et al. (*Theor. Appl. Genet.* (1988) 75:685–694; *Plant Cell Reports* (1992) 11:499–505). Transgenic *Arabidopsis thaliana* plants may be obtained by Agrobacterium-mediated transformation as described by Valverkens et al., (*Proc. Nat. Acad. Sci.* (1988) 85:5536–5540), or as described by Bent et al. ((1994), *Science* 265:1856–1860), or Bechtold et al. ((1993), *C.R. Acad. Sci, Life Sciences* 316:1194–1199). Other plant species may be similarly transformed using related techniques.

Alternatively, microprojectile bombardment methods, such as described by Klein et al. (*Bio/Technology* 10:286–291) may also be used to obtain nuclear transformed plants.

Seeds or other plant material from transformed plants may be analyzed for DAGAT activity using the DAGAT assay methods described in Examples 1 and 7.

The above results demonstrate the ability to obtain partially purified DAGAT proteins which are active in the formation of triacylglycerols from fatty acyl and diacylglycerol substrates. Methods to obtain the DAGAT proteins and amino acid sequences thereof are provided. In addition DAGAT nucleic acid sequences may also be obtained from the amino acid sequences using PCR and library screening methods provided herein. Such nucleic acid sequences may be manipulated to provide for transcription of the sequences and/or expression of DAGAT proteins in host cells, which proteins can be used for a variety of applications. Such applications include the modification of triacylglycerols levels and compositions in host cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. An isolated nucleic acid molecule encoding a diacylglycerol acyltransferase protein of SEQ ID NO: 38.

2. The isolated nucleic acid molecule of claim 1, wherein the nucleic acid molecule is resynthesized to include therein plant-preferred codons.

3. A plant cell having as operably linked components a promoter, an isolated nucleic acid molecule encoding a diacylglycerol acyltransferase protein of SEQ ID NO: 38, and a transcription termination sequence.

4. The plant cell of claim 3, wherein the nucleic acid molecule is resynthesized to include therein plant-preferred codons.

5. A method of increasing the triacylglycerol in a plant comprising:
   transforming the plant with a construct comprising as operably linked components in the 5' to 3' direction of transcription, a promoter functional in a plant cell, a nucleic acid molecule encoding a diacylglycerol acyltransferase protein of SEQ ID NO: 38, and a transcription termination sequence capable of terminating transcription in a plant cell; and
   expressing said nucleic acid molecule in said plant;
   whereby expression increases the triacylglycerol in the plant.

6. The method of claim 5, wherein the nucleic acid molecule is resynthesized to include therein plant-preferred codons.

7. The method of claim 6, wherein the nucleic acid molecule comprises SEQ ID NO: 84.

8. An isolated nucleic acid sequence that encodes a diacylglycerol acyltransferase protein from *Mortierella ramanniana,* wherein said isolated nucleic acid sequence has been resynthesized to provide plant-preferred codon sequences for encoding said diacylglycerol acyltransferase protein, and wherein the resynthesized sequence comprises SEQ ID NO: 84.

9. The plant cell of claim 4, wherein the resynthesized sequence comprises SEQ ID NO: 84.

* * * * *

SEQUENCE LISTING

<160> NUMBER OF SEQ ID NOS: 84

<210> SEQ ID NO 1
<211> LENGTH: 10
<212> TYPE: PRT
<213> ORGANISM: Mortierella ramanniana -continued

```
<400> SEQUENCE: 1

Glu Leu His Asp Ser Tyr Met His Ala Val
 1               5                  10

<210> SEQ ID NO 2
<211> LENGTH: 16
<212> TYPE: PRT
<213> ORGANISM: Mortierella ramanniana

<400> SEQUENCE: 2

Lys Ile Gln His Ala Leu Gly Phe Thr Met Pro Leu Phe His Gly Arg
 1               5                  10                  15

<210> SEQ ID NO 3
<211> LENGTH: 7
<212> TYPE: PRT
<213> ORGANISM: Mortierella ramanniana

<400> SEQUENCE: 3

His Pro Ile Tyr Thr Ile Val
 1               5

<210> SEQ ID NO 4
<211> LENGTH: 6
<212> TYPE: PRT
<213> ORGANISM: Mortierella ramanniana

<400> SEQUENCE: 4

Asn Ala Ala Trp Pro Lys
 1               5

<210> SEQ ID NO 5
<211> LENGTH: 8
<212> TYPE: PRT
<213> ORGANISM: Mortierella ramanniana

<400> SEQUENCE: 5

Val Lys Glu Leu Glu Phe Val Glu
 1               5

<210> SEQ ID NO 6
<211> LENGTH: 3
<212> TYPE: PRT
<213> ORGANISM: Mortierella ramanniana

<400> SEQUENCE: 6

Phe Gly Phe
 1

<210> SEQ ID NO 7
<211> LENGTH: 11
<212> TYPE: PRT
<213> ORGANISM: Mortierella ramanniana
<220> FEATURE:
<221> NAME/KEY: unsure
<222> LOCATION: (1)..(11)
<223> OTHER INFORMATION: unsure at all Xaa locations

<400> SEQUENCE: 7

Tyr Xaa His Asp Ala Tyr Pro His Ala Val Glu
 1               5                  10

<210> SEQ ID NO 8
<211> LENGTH: 16
<212> TYPE: PRT
```

-continued

<213> ORGANISM: Mortierella ramanniana

<400> SEQUENCE: 8

Glu Leu His Asp Ser Tyr Met His Ala Val Gln Asp Leu Tyr Asp Arg
 1               5                  10                  15

<210> SEQ ID NO 9
<211> LENGTH: 13
<212> TYPE: PRT
<213> ORGANISM: Mortierella ramanniana

<400> SEQUENCE: 9

Gly Val Phe Asn Tyr Asp Phe Gly Leu Leu Pro His Arg
 1               5                  10

<210> SEQ ID NO 10
<211> LENGTH: 8
<212> TYPE: PRT
<213> ORGANISM: Mortierella ramanniana
<220> FEATURE:
<221> NAME/KEY: unsure
<222> LOCATION: (1)..(8)
<223> OTHER INFORMATION: unsure at all Xaa locations

<400> SEQUENCE: 10

Xaa Leu Ala Gly Ile Phe Pro Ala
 1               5

<210> SEQ ID NO 11
<211> LENGTH: 15
<212> TYPE: PRT
<213> ORGANISM: Mortierella ramanniana

<400> SEQUENCE: 11

Ile Ala Val Gln Thr Gly Ala Gly Leu Val Pro Thr Leu Ser Phe
 1               5                  10                  15

<210> SEQ ID NO 12
<211> LENGTH: 15
<212> TYPE: PRT
<213> ORGANISM: Mortierella ramanniana

<400> SEQUENCE: 12

Ser Ile Ala Ile Val Val Gly Ser Ala Ser Glu Ser Ile Asn Ala
 1               5                  10                  15

<210> SEQ ID NO 13
<211> LENGTH: 10
<212> TYPE: PRT
<213> ORGANISM: Mortierella ramanniana
<220> FEATURE:
<221> NAME/KEY: unsure
<222> LOCATION: (1)..(10)
<223> OTHER INFORMATION: unsure at all Xaa locations

<400> SEQUENCE: 13

Gly Phe Phe Asn Tyr Asp Phe Xaa Xaa Leu
 1               5                  10

<210> SEQ ID NO 14
<211> LENGTH: 10
<212> TYPE: PRT
<213> ORGANISM: Mortierella ramanniana

<400> SEQUENCE: 14

Glu Leu His Asp Ser Tyr Met His Ala Val

-continued

```
        1               5                  10
```

<210> SEQ ID NO 15
<211> LENGTH: 7
<212> TYPE: PRT
<213> ORGANISM: Mortierella ramanniana

<400> SEQUENCE: 15

```
Val His Trp Ala Pro Leu Arg
 1               5
```

<210> SEQ ID NO 16
<211> LENGTH: 6
<212> TYPE: PRT
<213> ORGANISM: Mortierella ramanniana

<400> SEQUENCE: 16

```
Lys Leu Pro Leu Phe Lys
 1               5
```

<210> SEQ ID NO 17
<211> LENGTH: 9
<212> TYPE: PRT
<213> ORGANISM: Mortierella ramanniana
<220> FEATURE:
<221> NAME/KEY: unsure
<222> LOCATION: (1)..(9)
<223> OTHER INFORMATION: unsure at all Xaa locations

<400> SEQUENCE: 17

```
Val Asp Leu Asp Xaa Ala Pro Pro Arg
 1               5
```

<210> SEQ ID NO 18
<211> LENGTH: 10
<212> TYPE: PRT
<213> ORGANISM: Mortierella ramanniana

<400> SEQUENCE: 18

```
Ile Thr Gly Phe Thr Val Pro His Ala His
 1               5                  10
```

<210> SEQ ID NO 19
<211> LENGTH: 10
<212> TYPE: PRT
<213> ORGANISM: Mortierella ramanniana
<220> FEATURE:
<221> NAME/KEY: unsure
<222> LOCATION: (1)..(10)
<223> OTHER INFORMATION: unsure at all Xaa locations

<400> SEQUENCE: 19

```
Glu Leu His Asp Ser His Met Leu Xaa Val
 1               5                  10
```

<210> SEQ ID NO 20
<211> LENGTH: 13
<212> TYPE: PRT
<213> ORGANISM: Mortierella ramanniana

<400> SEQUENCE: 20

```
Gly Ile Phe Asn Tyr Asn Ala Gly Phe Ile Pro Phe Arg
 1               5                  10
```

<210> SEQ ID NO 21
<211> LENGTH: 13

-continued

```
<212> TYPE: PRT
<213> ORGANISM: Mortierella ramanniana

<400> SEQUENCE: 21

His Pro Ile Tyr Thr Ile Val Gly Lys Pro Ile Pro Val
  1               5                  10

<210> SEQ ID NO 22
<211> LENGTH: 8
<212> TYPE: PRT
<213> ORGANISM: Mortierella ramanniana

<400> SEQUENCE: 22

Gly Ser Cys Glu Ala Ile Leu Arg
  1               5

<210> SEQ ID NO 23
<211> LENGTH: 26
<212> TYPE: PRT
<213> ORGANISM: Mortierella ramanniana

<400> SEQUENCE: 23

His Pro Ile Val Thr Val Val Gly Lys Pro Ile Ala Val Pro Leu Leu
  1               5                  10                  15

Ala Glu Gly Glu Thr Glu Pro Pro Ser Glu
             20                  25

<210> SEQ ID NO 24
<211> LENGTH: 29
<212> TYPE: PRT
<213> ORGANISM: Mortierella ramanniana

<400> SEQUENCE: 24

Ser Arg Asp Ser Thr Pro Val Ile Thr Glu His Lys Gln Pro Met Glu
  1               5                  10                  15

Gln Val Gln Val Thr Ala Leu Leu Asp His Ile Pro Val
             20                  25

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: degenerate
      primer for peptide in SEQ ID NO: 5
<220> FEATURE:
<221> NAME/KEY: unsure
<222> LOCATION: (1)..(28)
<223> OTHER INFORMATION: unsure at all n locations

<400> SEQUENCE: 25
cactgcagac raaytcnary tcyttnac                                            28

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Degenerate
      primer to SEQ ID NO: 9
<220> FEATURE:
<221> NAME/KEY: unsure
<222> LOCATION: (1)..(30)
<223> OTHER INFORMATION: unsure at all n locations

<400> SEQUENCE: 26
```

```
ccaagcttgg ngtnttyaay taygayttyg                              30
```

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: degenerate
      primer to SEQ ID NO: 9
<220> FEATURE:
<221> NAME/KEY: unsure
<222> LOCATION: (1)..(30)
<223> OTHER INFORMATION: unsure at all n locations

<400> SEQUENCE: 27

```
cactgcagcr aartcrtart traanacncc                              30
```

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: degenerate
      primer to SEQ ID NO: 8
<220> FEATURE:
<221> NAME/KEY: unsure
<222> LOCATION: (1)..(30)
<223> OTHER INFORMATION: unsure at all n locations

<400> SEQUENCE: 28

```
cactgcagcy tgnacngcng crtgcatrta                              30
```

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 11
<220> FEATURE:
<221> NAME/KEY: unsure
<222> LOCATION: (1)..(28)
<223> OTHER INFORMATION: unsure at all n locations

<400> SEQUENCE: 29

```
ccaagcttat hgcngtncar acnggngc                                28
```

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 3
<220> FEATURE:
<221> NAME/KEY: unsure
<222> LOCATION: (1)..(28)
<223> OTHER INFORMATION: unsure at all n locations

<400> SEQUENCE: 30

```
ccaagcttaa rcayccnath tayacnat                                28
```

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 3
<220> FEATURE:

```
<221> NAME/KEY: unsure
<222> LOCATION: (1)..(28)
<223> OTHER INFORMATION: unsure at all n locations

<400> SEQUENCE: 31
cactgcagac datngtrtad atnggrtg                                            28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 2
<220> FEATURE:
<221> NAME/KEY: unsure
<222> LOCATION: (1)..(28)
<223> OTHER INFORMATION: unsure at all n locations

<400> SEQUENCE: 32
ccaagcttgc nytnggntty acnatgcc                                            28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 2
<220> FEATURE:
<221> NAME/KEY: unsure
<222> LOCATION: (1)..(28)
<223> OTHER INFORMATION: unsure at all n locations

<400> SEQUENCE: 33
ccaagctttt yacnatgccn ytnttyca                                            28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: degenerate
      primer to SEQ ID NO: 2
<220> FEATURE:
<221> NAME/KEY: unsure
<222> LOCATION: (1)..(28)
<223> OTHER INFORMATION: unsure at all n locations

<400> SEQUENCE: 34
cactgcagaa rtgraanarn ggcatngt                                            28

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: RACE PCR
      primer for MR1

<400> SEQUENCE: 35
ggtttgctcc cccatcgcca tcctatc                                             27

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: RACE PCR
``` primer for MR1

<400> SEQUENCE: 36
gataggatgg cgatggggga gcaaacc                     27

<210> SEQ ID NO 37
<211> LENGTH: 1065
<212> TYPE: DNA
<213> ORGANISM: Mortierella ramanniana

<400> SEQUENCE: 37

| atggccagca | aggatcaaca | tttacagcag | aaggtcaagc | atacgctaga | agctatccca | 60 |
| tccctcgct | atgctccatt | gcgagtgcca | ttaagacgga | gattacaaac | attggcagta | 120 |
| tttattatgg | tgttccatga | tgtcaatatg | catgtcatat | tcttcttttt | atgctcattc | 180 |
| ctgttctcct | ttggttccca | ttatctttat | ttgacctgga | tcttggtgtg | ggataaggcg | 240 |
| ccagagaacg | gtgaagacc | tattcgctgc | ctgcggaatg | ctgcttggtg | aagctgttt | 300 |
| gcagggtatt | tcccgcaca | tatcatcaag | gaagccgatt | tagatccatc | aagaacaca | 360 |
| atctttggtt | atcaccccca | tggaatcata | tccatgggct | cgttctgtac | ttttaagtcc | 420 |
| aatgctactg | gctttgatga | cttgttccca | ggcatccggc | catcgctttt | gacattaaca | 480 |
| tctaatttta | atatcccact | ttatcgtgat | tatttgatgg | cgtgcggact | ttgctccgtc | 540 |
| tccaaaacat | cctgtcaaaa | tattttaacc | aaaggtggtc | cgggccgttc | cattgccatt | 600 |
| gtcgtgggag | gtgcttccga | gtctctcaat | gctagacccg | tgtcatgga | ccttgtgttg | 660 |
| aagagacgct | ttggttttat | caagattgct | gttcaaaccg | gtgcaagtct | agtgcccact | 720 |
| atcagttttg | gtgaaaatga | gctgtacgaa | cagattgaaa | gcaatgaaaa | ctcaaagttg | 780 |
| catagatggc | aaaagaagat | tcaacatgct | cttggtttta | ctatgccgct | ctttcatgga | 840 |
| cgcggtgtat | tcaattatga | ctttggtttg | ctcccccatc | gccatcctat | ctacacgatt | 900 |
| gttggaaagc | ccatccccgt | ccctagcatc | aagtatggac | agacaaagga | tgagattata | 960 |
| agagaactac | atgactcgta | catgcatgcc | gtgcaggatc | tctatgatcg | ttacaaggat | 1020 |
| atctatgcaa | aggatcgggt | aaaagaacta | gaattcgtcg | aatag | | 1065 |

<210> SEQ ID NO 38
<211> LENGTH: 354
<212> TYPE: PRT
<213> ORGANISM: Mortierella ramanniana

<400> SEQUENCE: 38

Met Ala Ser Lys Asp Gln His Leu Gln Gln Lys Val Lys His Thr Leu
 1               5                  10                  15

Glu Ala Ile Pro Ser Pro Arg Tyr Ala Pro Leu Arg Val Pro Leu Arg
             20                  25                  30

Arg Arg Leu Gln Thr Leu Ala Val Phe Ile Met Val Phe His Asp Val
         35                  40                  45

Asn Met His Val Ile Phe Phe Phe Leu Cys Ser Phe Leu Phe Ser Phe
     50                  55                  60

Gly Ser His Tyr Leu Tyr Leu Thr Trp Ile Leu Val Trp Asp Lys Ala
 65                  70                  75                  80

Pro Glu Asn Gly Gly Arg Pro Ile Arg Cys Leu Arg Asn Ala Ala Trp
                 85                  90                  95

Trp Lys Leu Phe Ala Gly Tyr Phe Pro Ala His Ile Ile Lys Glu Ala
            100                 105                 110

-continued

```
Asp Leu Asp Pro Ser Lys Asn Thr Ile Phe Gly Tyr His Pro His Gly
        115                 120                 125

Ile Ile Ser Met Gly Ser Phe Cys Thr Phe Lys Ser Asn Ala Thr Gly
    130                 135                 140

Phe Asp Asp Leu Phe Pro Gly Ile Arg Pro Ser Leu Leu Thr Leu Thr
145                 150                 155                 160

Ser Asn Phe Asn Ile Pro Leu Tyr Arg Asp Tyr Leu Met Ala Cys Gly
                165                 170                 175

Leu Cys Ser Val Ser Lys Thr Ser Cys Gln Asn Ile Leu Thr Lys Gly
            180                 185                 190

Gly Pro Gly Arg Ser Ile Ala Ile Val Val Gly Ala Ser Glu Ser
        195                 200                 205

Leu Asn Ala Arg Pro Gly Val Met Asp Leu Val Leu Lys Arg Arg Phe
    210                 215                 220

Gly Phe Ile Lys Ile Ala Val Gln Thr Gly Ala Ser Leu Val Pro Thr
225                 230                 235                 240

Ile Ser Phe Gly Glu Asn Glu Leu Tyr Glu Gln Ile Glu Ser Asn Glu
                245                 250                 255

Asn Ser Lys Leu His Arg Trp Gln Lys Lys Ile Gln His Ala Leu Gly
            260                 265                 270

Phe Thr Met Pro Leu Phe His Gly Arg Gly Val Phe Asn Tyr Asp Phe
    275                 280                 285

Gly Leu Leu Pro His Arg His Pro Ile Tyr Thr Ile Val Gly Lys Pro
290                 295                 300

Ile Pro Val Pro Ser Ile Lys Tyr Gly Gln Thr Lys Asp Glu Ile Ile
305                 310                 315                 320

Arg Glu Leu His Asp Ser Tyr Met His Ala Val Gln Asp Leu Tyr Asp
                325                 330                 335

Arg Tyr Lys Asp Ile Tyr Ala Lys Asp Arg Val Lys Glu Leu Glu Phe
            340                 345                 350

Val Glu
```

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: Primer for
      amplification of MR1 coding sequence

<400> SEQUENCE: 39
aattcgcggc cgcatggcca gcaaggatca acatttacag c                    41

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Primer for
      amplification of MR1 coding sequence

<400> SEQUENCE: 40
tgctgcagct attcgacgaa ttctagttct tttacccgat cc                   42

<210> SEQ ID NO 41
<211> LENGTH: 23
<212> TYPE: DNA
<213> ORGANISM: Artificial Sequence
<220> FEATURE:

```
<223> OTHER INFORMATION: Description of Artificial Sequence: degenerate
      primer for SEQ ID NO: 23
<220> FEATURE:
<221> NAME/KEY: unsure
<222> LOCATION: (1)..(23)
<223> OTHER INFORMATION: unsure at all n locations

<400> SEQUENCE: 41
ggcacngcda tnggyttncc nac                                          23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: degenerate
      primer for SEQ ID NO: 20
<220> FEATURE:
<221> NAME/KEY: unsure
<222> LOCATION: (1)..(23)
<223> OTHER INFORMATION: unsure at all n locations

<400> SEQUENCE: 42
ccngcrttrt arttraadat ncc                                          23

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: primer for
      5' RACE amplification of MR2

<400> SEQUENCE: 43
tgcctagtga catcatgaaa tctcg                                        25

<210> SEQ ID NO 44
<211> LENGTH: 845
<212> TYPE: DNA
<213> ORGANISM: Mortierella ramanniana

<400> SEQUENCE: 44
atggaacaag tccaagtcac tgcattgctc gaccacattc ccaaagtcca ttgggcaccg    60
ctccgcggga tccctttgaa gcgtcgctta caaacgtcgg ctatcgtcac atggctggct   120
tgcttcccta tctgtctcat tatatacctg tacctattca ccattccctt attatggccc   180
atcctcatta tgtatacgat atggctgttt ttcgacaaag cccctgaaaa cggaggcaga   240
cgaatttcgc tggtgaggaa attgccgctg tggaagcatt ttgccaatta tttcccagtc   300
actttgatca aggaaggaga cctcgacccc aagggaaact acatcatgtc atatcatccg   360
catggaataa tatccatggc ggcttttgcc aattttgcga ctgaggcgac tgggttttcc   420
gagcaatatc cggtattgt tccttcatta ctgacgctag catccaattt tcggttgcca   480
ttgtaccgag atttcatgat gtcactaggc atgtgctcgg tatcgcgaca ctcctgtgaa   540
gctatccttc gttcggggcc cggtcgatcc attgtgattg ttacaggcgg agcttcagaa   600
tcccttagcg cacgaccagg caccaacgac ctcaccctca agaaacgatt gggtttcatc   660
cgactagcca ttcgaaatgg tgccagttta gtgcctatct tttcgtttgg agagaacgac   720
atctacgagc aatatgataa caaaaagggc agtttgatat ggcggtacca aaaatggttc   780
caaaaaatta caggattcac ggttcctttg gctcatgccc gtggaatytt caactacaac   840
gcggg                                                              845
```

<210> SEQ ID NO 45
<211> LENGTH: 281
<212> TYPE: PRT
<213> ORGANISM: Mortierella ramanniana

<400> SEQUENCE: 45

Met Glu Gln Val Gln Val Thr Ala Leu Leu Asp His Ile Pro Lys Val
1               5                   10                  15

His Trp Ala Pro Leu Arg Gly Ile Pro Leu Lys Arg Arg Leu Gln Thr
            20                  25                  30

Ser Ala Ile Val Thr Trp Leu Ala Leu Leu Pro Ile Cys Leu Ile Ile
        35                  40                  45

Tyr Leu Tyr Leu Phe Thr Ile Pro Leu Leu Trp Pro Ile Leu Ile Met
    50                  55                  60

Tyr Thr Ile Trp Leu Phe Phe Asp Lys Ala Pro Glu Asn Gly Gly Arg
65                  70                  75                  80

Arg Ile Ser Leu Val Arg Lys Leu Pro Leu Trp Lys His Phe Ala Asn
                85                  90                  95

Tyr Phe Pro Val Thr Leu Ile Lys Glu Gly Asp Leu Asp Pro Lys Gly
            100                 105                 110

Asn Tyr Ile Met Ser Tyr His Pro His Gly Ile Ile Ser Met Ala Ala
        115                 120                 125

Phe Ala Asn Phe Ala Thr Glu Ala Thr Gly Phe Ser Glu Gln Tyr Pro
    130                 135                 140

Gly Ile Val Pro Ser Leu Leu Thr Leu Ala Ser Asn Phe Arg Leu Pro
145                 150                 155                 160

Leu Tyr Arg Asp Phe Met Met Ser Leu Gly Met Cys Ser Val Ser Arg
                165                 170                 175

His Ser Cys Glu Ala Ile Leu Arg Ser Gly Pro Gly Arg Ser Ile Val
            180                 185                 190

Ile Val Thr Gly Gly Ala Ser Glu Ser Leu Ser Ala Arg Pro Gly Thr
        195                 200                 205

Asn Asp Leu Thr Leu Lys Lys Arg Leu Gly Phe Ile Arg Leu Ala Ile
    210                 215                 220

Arg Asn Gly Ala Ser Leu Val Pro Ile Phe Ser Phe Gly Glu Asn Asp
225                 230                 235                 240

Ile Tyr Glu Gln Tyr Asp Asn Lys Lys Gly Ser Leu Ile Trp Arg Tyr
                245                 250                 255

Gln Lys Trp Phe Gln Lys Ile Thr Gly Phe Thr Val Pro Leu Ala His
            260                 265                 270

Ala Arg Gly Ile Phe Asn Tyr Asn Ala
        275                 280

<210> SEQ ID NO 46
<211> LENGTH: 355
<212> TYPE: DNA
<213> ORGANISM: Zea mays

<400> SEQUENCE: 46
tgcctaagac tggttgcttt tcttaaatca agaaaaggtt ttgtcaagat agctatacag    60
tctggatgtc ctttagtccc agttttctgc tttgggcaga gctatgcata caagtggtgg   120
aggcctggtg gtaaattgtt tatcaagatc gctagagcag ttaaatttac tcctattatc   180
ttctgggata gatttggcac accattcccc ttcccaaaac ccatgcatgt ggtcgtgggt   240
aaaccaattg aagtcaataa gattccccat cctacaattg acgagattaa tgaagtccat   300

```
ggacagttca tcattgccat gcgggacctc tttgagagct gtatcatcag tgtct        355

<210> SEQ ID NO 47
<211> LENGTH: 375
<212> TYPE: DNA
<213> ORGANISM: Zea mays

<400> SEQUENCE: 47
cccacgcgtc cgcgagctta tgttttgct tatgaaccgc attcggtgct gcctattggc    60
gtttgtgcgc ttgcggatca tacaggtttt ttgcccctgc cgaagattaa ggctcttgcg   120
agtaccgcgg ttttctatgt gccgtttgtg aggcagatat ggacatggtt ggggcttgtc   180
cctgcgtcga gaaggaattt ttacgagtac ttggcggctg gtatagttg catcatagtg    240 ccgggtggtg tgcaggagtt gttgtatatg aatgtgatt cggaggttgc ttttcttaaa    300
tcaaggaaag gatttgtaaa gatagccatg gagatgggtc aacctcttgt acctgtattc   360
tgctttggtc agagt                                                    375

<210> SEQ ID NO 48
<211> LENGTH: 477
<212> TYPE: DNA
<213> ORGANISM: Brassica napus
<220> FEATURE:
<221> NAME/KEY: unsure
<222> LOCATION: (1)..(477)
<223> OTHER INFORMATION: unsure at all n locations

<400> SEQUENCE: 48
aacnttactt gccaggcacc ggtcaagaan tcccgggtcg acccacgcgt ccgcaaatac    60
ggtcgaatgc tcgctaggta catatgtaaa cacgcgtgta gttatttccc cgttactctc   120
catgtcgagg attacgaagc tttccagcct actcgtgcct atgttttgg ttatgaacca    180 cattcggtgt ggcctattgg agctgttgca cttgctgatc ttacgggtt catgcctctt    240 cctaacatca aagttcttgc tagtactgct gttttctaca cccctttct gaggcaaata    300 tggacgtggt tagggctcgc ccctgcttct aggaagaatt tcgcttccta tttggactct   360
ggctatagtt gtatcctcgt acctggtggt gtccaggaga catttcacat gaaacatgat   420
gttgagaact tattcctttc atccgagaan ggggtttgtg cgcatcgcca tgggagc     477

<210> SEQ ID NO 49
<211> LENGTH: 498
<212> TYPE: DNA
<213> ORGANISM: Glycine max
<220> FEATURE:
<221> NAME/KEY: unsure
<222> LOCATION: (1)..(498)
<223> OTHER INFORMATION: unsure at all n locations

<400> SEQUENCE: 49
nngcttccta tcaacgtgca gtgggatttg gccgaagatt gtcgaggttc atatgcaagc    60
acgcagtgca attactctcc gatcacgctt cacgtagagg atatgaaagc ctttgatcct   120
aaccgtgctt atgttttgg gtatgaacca cattcagttt gccaattgg catacgtnnt    180 gcattggctg accacacagg tttcatgcct cttccaaaag ttaaagttct tgctagcagc   240
acggtgttct acacaccatt ttacacacca ttttgagac acatatggac atggtttggt   300
ctaacgccag tgacaaagaa aaggtttacc tcgctgttgg atgctggcta tagttgtatc   360
ttgatacctg gtggagtgca agaagcattt ctcattgagc atggttctga gattgccttt   420
```

```
cttaaatcaa ggagaggatt tgtccgcata gcaatggaga agggaaaacc cctggttcca    480
gttttctgct ttggtcag                                                  498
```

<210> SEQ ID NO 50
<211> LENGTH: 393
<212> TYPE: DNA
<213> ORGANISM: Arabidopsis thaliana
<220> FEATURE:
<221> NAME/KEY: unsure
<222> LOCATION: (1)..(393)
<223> OTHER INFORMATION: unsure at all n locations

<400> SEQUENCE: 50

```
gcgtccgtcg ccatggccat ctggcttggc gccattcact tcaacgtcgc tcttgttctc     60
tgttctctca ttttccttcc tccttctcta tctctcatgg tcttgggctt gctctctctg    120
tttatcttta tcccaatcga tcatcgtagc aaatatggtc gtaagctcgc taggtacata    180
tgcaagcacg cgtgtaatta ttttccccgtc tctctgtacg tcgaggatta cgaancttc    240 cagcctaatc gtgcctatgt ctttggttat gaaccacatt cggtgctacc gattggantt    300
gtngctcttt tgtgatctcac anggtttatg cctaatccta acattaaagt tcttgcaant   360
agtgctaaat tcaaaattcc ctttcaaagg ata                                 393
```

<210> SEQ ID NO 51
<211> LENGTH: 344
<212> TYPE: DNA
<213> ORGANISM: Arabidopsis thaliana
<220> FEATURE:
<221> NAME/KEY: unsure
<222> LOCATION: (1)..(344)
<223> OTHER INFORMATION: unsure at all n locations

<400> SEQUENCE: 51

```
cttgccgtgc cggtccgaaa taacgggtcg acncacgcgt ccgtgtacgt cgaggattac     60
gaagctttcc agcctaatcg tgcctatgtc tttggttatg aaccacattc ggtgctaccg    120
attggagttg ttgctctttg tgatctcaca gggtttatgc cnattcctaa cattaaagtt    180
cttgcaagta gtgctatatt ctacactccc tttctaaggc atatatggac atggttaggg    240
ctcaccgctg cttctaggaa naatttcact tcccttttgg attctggcta cagttgtgtt    300
cttgtacctg gtgggtgtgc aggagacttt tcanatgcan catg                     344
```

<210> SEQ ID NO 52
<211> LENGTH: 462
<212> TYPE: DNA
<213> ORGANISM: Arabidopsis thaliana

<400> SEQUENCE: 52

```
cgagagaagc acattttggg gtacgcacca catggtatgt tcccgatggg cgcctcttat     60
ctccacaaca cctcgatgtg gatggaactc ttcccaaaca ttgtgcctta tacacttaca    120
gcgacggtga ctcatctggt tccgtttcta agagaagtga ctcagtataa cggaggtgtt    180
gaagtcagtc aaagtagttt tgcaaacgcg ttgatgaaat tcaaaaacgt tttgctggtc    240
cccggaggac aacatgaaat gttactcatc agcgacgacc ataacgaagt gcttttatcc    300
gccaaacaca agggattcat tcgattagcc ttgcaatcgg cagcagaaaa cccagatgaa    360
gtcatcaacc tcgtcccggt gtacgctttt ggagaaaaag acaaaatgta taacgcattc    420
cctgcgagtc tctctctgca gcgatatctg gtggccaagc tg                       462
```

```
<210> SEQ ID NO 53
<211> LENGTH: 489
<212> TYPE: DNA
<213> ORGANISM: Human
<220> FEATURE:
<221> NAME/KEY: unsure
<222> LOCATION: (1)..(489)
<223> OTHER INFORMATION: unsure at all n locations

<400> SEQUENCE: 53
cccagcccca gcttcgggca ggccgtggtc atcatggtgg ggggtgcgca cgaggccctg      60
tattcagtcc ccggggagca ctgccttacg ctccagaagc gcaaaggctt cgtgcgcctg     120
gcgctgaggc acggggcgtn cntggtgccc gtgtactcct ttggggagaa tgacatcttt     180
agacttaagg cttttgccac aggnncctgg cagnattggt gccagctcac cttcaagaag     240
ctcatgggct tntcnccttg catnttctgg ggtngcggtn tcttctcagc cacntcntgg     300
ggcctgctgn nctttgctgt gcccatcacn actgtggtgg nnngnacnat nnccntnaan     360
cagaaccncc acccnaccga ggaggaaatn aatnactatn acgnnntcta catgacggnc     420
ntggagcagn tcttcgagga gnanaaggaa agntgtgggg acccngcttc cacctgcntn     480 accttnatc                                                            489

<210> SEQ ID NO 54
<211> LENGTH: 333
<212> TYPE: DNA
<213> ORGANISM: Human

<400> SEQUENCE: 54
tggcccttct ctgtttttta cttggtgtgg ctctatgtgg actgggacac acccaaccaa      60
ggtggaaggc gttcggagtg gataaggaac cgggcaattt ggagacaact aagggattat     120
tatcctgtca agctggtgaa acagcagag ctgccccgg atcgaacta cgtgctgggc        180 gcccaccctc atgggatcat gtgtacaggc ttcctctgta atttctccac cgagagcaat     240
ggcttctccc agctcttccc ggggctccgg ccctggttag ccgtgctggc tggcctcttc     300 tacctccccgg tctatcgcga ctacatcatg tcc                                 333

<210> SEQ ID NO 55
<211> LENGTH: 222
<212> TYPE: DNA
<213> ORGANISM: Human

<400> SEQUENCE: 55
atcattgtag ggggtgccca ggaggccctg gatgccaggc ctggatcctt cacgctgtta      60
ctgcggaacc gaaagggctt cgtcaggctc gccctgacac acggggcacc cctggtgcca     120
atcttctcct tcggggagaa tgacctattt gaccagattc ccaactcttc tggctcctgg     180
ttacgctata tccagaatcg gttgcagaag atcatgggca tc                        222

<210> SEQ ID NO 56
<211> LENGTH: 827
<212> TYPE: DNA
<213> ORGANISM: Human

<400> SEQUENCE: 56
ctccagtggg tcctgtcctt ccttgtactg ggagtggcct gcagtgccat cctcatgtac      60
atattctgca ctgattgctg gctcatcgct gtgctctact tcacttggct ggtgtttgac     120
tggaacacac ccaagaaagg tggcaggagg tcacagtggg tccgaaactg ggctgtgtgg     180
```

```
cgctactttc gagactactt tcccatccag ctggtgaaga cacacaacct gctgaccacc      240
aggaactata tctttggata ccaccccat ggtatcatgg gcctgggtgc cttctgcaac       300
ttcagcacag aggccacaga agtgagcaag aagttcccag gcatacggcc ttacctggct      360
acactggcag gcaacttccg aatgcctgtg ttgagggagt acctgatgtc tggaggtatc      420
tgccctgtca gccgggacac catagactat ttgctttcaa agaatgggag tggcaatgct      480
atcatcatcg tggtcggggg tgcggctgag tctctgagct ccatgcctgg caagaatgca      540
gtcaccctgc ggaaccgcaa gggctttgtg aaactggccc tgcgtcatgg agctgacctg      600
gttcccatct actcctttgg agagaatgaa gtgtacaagc aggtgatctt cgaggagggc      660
tcctggggcc gatgggtcca gaagaagttc cagaaataca ttggtttcgc cccatgcatc      720
ttccatggtc gaggcctctt ctcctccgac acctgggggc tggtgcccta ctccaagccc      780
atcaccactg ttgtgggaga gcccatcacc atccccaagc tggagca                   827

<210> SEQ ID NO 57
<211> LENGTH: 265
<212> TYPE: DNA
<213> ORGANISM: Human
<220> FEATURE:
<221> NAME/KEY: unsure
<222> LOCATION: (1)..(265)
<223> OTHER INFORMATION: unsure at all n locations

<400> SEQUENCE: 57
agcgattatt tccctctcaa gcttctgaag actcatgaca tctgcccag ccgcaactac       60 atcctcgtct gccaccctca tgggctcttt gcccatggat ggtttggcca ctttgccaca     120
gaggcctcag gcttctccaa gatatttccn ggcatcaccc cttacatact cacactggga    180 gccttttct ggatgccttt cctcagagaa tatgtaatgt ctacaggggc ctgctctgtg      240
agtcgatcct ccattgactt tctgc                                           265

<210> SEQ ID NO 58
<211> LENGTH: 342
<212> TYPE: DNA
<213> ORGANISM: murine

<400> SEQUENCE: 58
ctmgtgcagg tgtgcattgg aattatggtg atgctggtcc tgtacaacta ttggttcctt      60
tacatcccat atctggtctg gttttactat gactggagaa ccccagagca aggaggcaga    120
agatggaact gggtccaaag ctggcctgtg tggaagtatt ttaaggagta ttttccaatc    180
tgtcttgtca aaacgcagga tttggatccg ggtcacaatt atatatttgg gtttcaccct    240
catggaatat tcgtgcctgg agcctttgga aattttgta caaatactc ggacttcaag      300 aagctatttc ctggctttac atcgtatctc cacgtggcca ag                       342

<210> SEQ ID NO 59
<211> LENGTH: 375
<212> TYPE: DNA
<213> ORGANISM: murine
<220> FEATURE:
<221> NAME/KEY: unsure
<222> LOCATION: (1)..(375)
<223> OTHER INFORMATION: unsure at all n locations

<400> SEQUENCE: 59
nttacctccc tcagggtcct gggcatcatg tcttgctcta tgaagactga acacttacag      60
agtctgagcc ttctgcagtg gcccttgagc tacgttgcca tgttttggat tgtgcagcca    120
```

```
ttgttaattt gcctattgtt cacacccttg tggccgctac caacagtttta ctttgtctgg      180 ttacttctcg actggaagac tccagataaa ggtggcaggc gttcagactg ggtacggaac      240
tggaatgtct ggaaccacat cagggactat ttccccatta caatcctgaa gactaaggac      300
ctgtcacctt cagagaacta catcatgggg gtccacccca tnggtctcct gaccttcggt      360
gccttctgca acttc                                                       375

<210> SEQ ID NO 60
<211> LENGTH: 885
<212> TYPE: DNA
<213> ORGANISM: murine
<220> FEATURE:
<221> NAME/KEY: unsure
<222> LOCATION: (1)..(885)
<223> OTHER INFORMATION: unsure at all n locations

<400> SEQUENCE: 60
gtactacaat gggtcctatc cttcctggtg ctaggagtgg cctgcagtgt catcctcatg       60
tacaccttct gcacagactg ctggctgata gctgtgctct acttcacctg ctggcatttt      120
gactggaaca cgcccaagaa aggtggcagg agatcgcagt gggtgcgaaa ctgggccgtg      180
tggcgctact tccgagacta ctttcccatc cagctggtga agacacacaa cctgctgacc      240
accaggaact atatctttgg ataccacccc catggcatca tgggcctggg tgccttctgt      300
aacttcagca cagaggctac tgaagtcagc aagaagtttc ctggcataag gccctatttg      360
gctacgttgg ctggtaactt ccggatgcct gtgcttcgcg agtacctgat gtctggaggc      420
atctggcctg tcaaccgaga caccatagac tacttgctct ccaagaatgg gagtggcaat      480
gctatcatca tcgtggtggg aggtgcagct gagtccctga ctccatgcc tggcaagaac       540 gcagtcaccc tgaagaaccg caaaggcttt gtgaanknyyg gatccmtgcg ccatggagct      600
gatctggttc ccacttattc ctttggagag aatgaggtat acaagcaggt gatctttgag      660
gagggttcct ggggccgatg ggtccagaag aagttccaga gtatattgg tttcgccccc       720 tgcatcttcc atggccgagg cctcttctcc tctgacacct gggggctggt gcctactcca      780
agcccatcac caccgtcgtg ggggagccca tcactgtccc caagctggag cacccgaccc      840
agaaagacat cgacctgtac catgccatgt acatggaggc cctgg                     885

<210> SEQ ID NO 61
<211> LENGTH: 809
<212> TYPE: DNA
<213> ORGANISM: Aspergillus fumigatus
<220> FEATURE:
<221> NAME/KEY: unsure
<222> LOCATION: (1)..(809)
<223> OTHER INFORMATION: unsure at all n locations

<400> SEQUENCE: 61
gtcctcctcn acatcctcta cgtcaaatat ctcgccaaag cacacaaaac cggcacttta       60
gctctccgca acgaccgcct ccgcacgtcc tggatctgga aagcctacgc ctcctacttc      120
cccctccgcc tctaccgctc ggtgcccntc tcccccgca aaaagtacat cttcggctac       180
catccccacg gcatcgccct ccgaggagca ctcgggaccc tagccgccga cgctgccgca      240
ttctccgatc tcttccccgg cgttacgaac acgctcctga tgaaagacga ggcgttctac      300
cagcctatat atagggagta ccttctctct acgggggtga gcggcgtgtc ccactcgtcg      360
tgtatccgac acctgacccg cgcaggacat gatgggcagg gtatgggccg ggcgattacc      420
```

```
atcaccgttg gcggaagtcg cgagtataac attgcgcggc cggggacgat gtgtgtggtc    480
gtccgcatcc gcaanggctt tgtgcgggtg gcggttgaga cgggggcgga tctcgttcct    540
gttattgcct tcgggagaa tgagctcttt gattgtgtga atgtgtcctc gtcgactgtg    600 ctggggttg tggccagggt atgggagtgg gctgttggcc acaaggtggc gttttcgatt    660
gtcggttcaa catttctgtc cgtatcgcgg ccggtgaatg ttgttgtngg gganccgatt    720
cctgtgacgc ancancggtg ggatccgatc aagcgtatan tgaccattgc atggcatata    780
tccanggcac tggaanaatt ttnggaatg                                      809
```

<210> SEQ ID NO 62
<211> LENGTH: 668
<212> TYPE: DNA
<213> ORGANISM: Aspergillus fumigatus
<220> FEATURE:
<221> NAME/KEY: unsure
<222> LOCATION: (1)..(668)
<223> OTHER INFORMATION: unsure at all n locations

<400> SEQUENCE: 62

```
nctgcatttg ctactgaagc actcggattt tcgaggttgt ttccgggaat tacaaacact     60
ttacttaccc ttgattcgaa ttttcgaatt ccgttctaca gagaatatgc tcttgccatg    120
ggactcgcca gtgtttcccg ggagtcctgt gaaaacctgc tatctaaagg tggtgctgat    180
ggggaaggca tgggccgcgc gattacaatt gtcattggtg gggctcgtga gtccctgcat    240
gctttacctc actctctgcg ccttgtttta aaatgccgca aaggattcat aaggctagca    300
attcgcaccg gtgctgatct tgtgccagta cttgctttcg gcgaaaacga tctctatgag    360
caggtgcgat cagatcagca tcccattata cacaagcttc aaatgctcat taagcgtacg    420
atggggttca cagttccgct cttcatgct cgtgggttt caattatga cgtgggactg      480 atgccttatc gacgtccgtt gaatattgtc gttggcagac ctatacaagt cgttcaacag    540
cgtgacagag acaagattga cgaaacgtac attgatgacc ttcatgccaa gtatatacaa    600
gaactttcga cgcttrtngg gancaataca aaagatgtct tttgcggaag acccgaatc     660 ctcctgga                                                            668
```

<210> SEQ ID NO 63
<211> LENGTH: 435
<212> TYPE: DNA
<213> ORGANISM: Aspergillus ochraceus

<400> SEQUENCE: 63

```
atcaccatgc tcattacgtc ttgcttgaag cgacgtatgg ggttcataaa gctagccatc     60
cgcactggtg ctgaccttgt accagtcttg gcttttggag aaaatgatct atacgaacag    120
gtccgttcag atagccatcc ccttattcac aagttccaaa tgttggtgaa acagacactg    180
ggattcacca ttccgctgtt tcatgcacgc ggtgttttca attacgatgt tggcttgatg    240
ccgtaccgcc gccgctgaa tattgttgtc ggccggccaa ttcatgtggt tcagcaacag    300
gacagaaaca aaatcaatga cgactatatt gatcaactcc attcagagta cgtgagagaa    360
cttgagaggc tgtgggaaga gtggaaggac gtctacgcca agaccgggt ttctgaaatt     420 gaaatagtgg cctag                                                    435
```

<210> SEQ ID NO 64
<211> LENGTH: 597
<212> TYPE: DNA
<213> ORGANISM: Candida albicans -continued

```
<400> SEQUENCE: 64
atgaaaaatt tcatcatctg ggattggttt gtcagatatt tccctataaa ggtttataag      60
tctgtcgaat tggaaccaac attcaaagaa gttttggtag aggagactga aagttcagaa     120
gatgatgatg agcaagattt agtgtctgaa cggagcagaa cgttagttga taaagttttc     180 aaatttttg ggttgaaaaa acgtttgaat gacacttctc tggggaagtc agaaacctac      240
aagacagtgt ctactggtcc caggtatatt tttggatacc atcctcatgg agttatttca     300
atgggtgggg ttggtttatt tgctactaat tcattacgta acgagccata tacgccattt     360
ctaaaatttt tgaaaccatt cttccatgac agttccaaag gtgaacgttt atttcctggt     420
cttggaaata ttttcttgtt gacaattacc acacaatttg ccataccatt ttatcgtgat     480
tatttaatgg gattgggggt tactagtgca tcagcaaaga atattagaag tttgattagc     540
aacggtgata attctgtctg tattgtagtt ggtggggcag aagagtcttt gttaaac        597

<210> SEQ ID NO 65
<211> LENGTH: 362
<212> TYPE: DNA
<213> ORGANISM: Fusarium graminearum

<400> SEQUENCE: 65
atgtctattg ccacattggt ttcggccttt tggttgattt gcgccaaccc acttgcctgg      60
cctattatta tcccttattt aattcatctt gctctatcaa ctgccggtac taatggcaac     120
ttgacatacc gctcagaatg ggttcgaagc ctgaagttgt ggaaactttt cgctggatat     180
ttccccatga agttgcacaa aacgcacgat ctgcctaccg atagaaagta cattttttgga    240 taccatcccc acgtatcat ttcccatggt gcctttgccg cttttggtac caatgcccttt    300 ggattccgtg agctcttccc tgggatcaca aacacgttac ttactctaga gggggatcca    360
ct                                                                    362

<210> SEQ ID NO 66
<211> LENGTH: 431
<212> TYPE: DNA
<213> ORGANISM: Mortierella alpina
<220> FEATURE:
<221> NAME/KEY: unsure
<222> LOCATION: (1)..(431)
<223> OTHER INFORMATION: unsure at all n locations

<400> SEQUENCE: 66
cccctgatca tcatgtacct gctctgggcc ttcatactgg accgaggccc agagcgtggt      60
gcacgcccag tgcagtggta tcgtaactgg atcggatgga acactttgc tcaatacttt     120 cccatgactc ttgtcaagga aggagaactg gatccgtcca agaactacat ctttggctac     180
cacccgcacg gcatcatctc cttgggcgcg ttctgcacct tcgggaccga nggccttcat    240
ttctcaaaac gctttcnagg catcaagccg cagctgttga ccctgcatgc caactttcan    300
gttccgctct accgcgaaat ggtcatggcc cacggctgtg cttcggtctc tagagcctct    360
tgtgaacaca ttctgcggtc cggtgaagga tgctcggtcg tgatcgtcnt tgggggggtgc    420 tcaaganant t                                                          431

<210> SEQ ID NO 67
<211> LENGTH: 285
<212> TYPE: DNA
<213> ORGANISM: Schizochytrium aggregatum
<220> FEATURE:
```

<221> NAME/KEY: unsure
<222> LOCATION: (1)..(285)
<223> OTHER INFORMATION: unsure at all n locations

<400> SEQUENCE: 67

| | | | | | |
|---|---|---|---|---|---|
| tctatctcan | nggcctatct | gggaaatccg | cgcatcanng | gcanacggcg | cttgggatcc | 60 |
| cggatattcc | nttttcgcat | tgttgaagac | catttcagcc | tctcgatggt | gcgcacgtct | 120 |
| gaagagcctt | gggacccgga | gcacgagtac | atttgtggct | atcaccctca | cggnctcgtg | 180 |
| cccttgggng | ccgcttacat | gaaaatgacc | ccacaatggt | cggagctcct | ccccaatatt | 240 |
| gtgcccntta | ctctcagcgc | angcattncg | cntcangtac | cnana | | 285 |

<210> SEQ ID NO 68
<211> LENGTH: 1080
<212> TYPE: DNA
<213> ORGANISM: Caenorhabditis elegans

<400> SEQUENCE: 68

| | | | | | |
|---|---|---|---|---|---|
| atgagactcc | ggctgagctc | gatatctgga | aaggcgaagc | ttcccgataa | agaaatatgc | 60 |
| tcatcagttt | cgagaatatt | ggcaccattg | cttgttccat | ggaagcgacg | actcgagact | 120 |
| cttgccgtga | tgggtttcat | tttcatgtgg | gtaatcctac | caatcatgga | cctctgggta | 180 |
| ccattccacg | tcttgttcaa | tactcgatgt | tggttccttg | ttccactcta | cgctgtctgg | 240 |
| ttctactatg | attttgatac | accgaaaaaa | gcttcaagaa | gatggaattg | gccagaaga | 300 |
| cacgtagcct | ggaagtactt | tgccagctac | ttcccattga | gattgatcaa | gactgctgac | 360 |
| cttccggcgg | atcgtaatta | catcattggc | tctcatcctc | atggaatgtt | ctcggttggt | 420 |
| ggttttactg | caatgagcac | caacgcgacc | ggatttgaag | acaagttccc | gggaataaaa | 480 |
| tctcacatca | tgacgctaaa | tgggcaattt | tatttcccat | ttcgtcgaga | attcggaata | 540 |
| atgctcggtg | gaatcgaagt | ttcgaaagaa | tcacttgaat | acactctaac | taaatgtgga | 600 |
| aaaggacgag | catgcgcaat | tgtcattggc | ggagcctcgg | aggctcttga | agctcatccc | 660 |
| aataaaaata | cattgacgtt | gatcaatcga | cgtggtttct | gcaaatatgc | tctgaagttt | 720 |
| ggggcagacc | tcgtaccaat | gtacaatttc | ggagagaatg | atttatacga | gcagtatgaa | 780 |
| aacccgaagg | gatctagatt | gcgagaagtt | caggagaaaa | tcaaggacat | gttcggattg | 840 |
| tgtcccccat | tgctccgcgg | tcgatcgttg | ttcaaccaat | accttatcgg | attgctgccg | 900 |
| ttccgaaaac | cagttacaac | agtcatggga | aggccaattc | gggtcaccca | aaccgacgag | 960 |
| ccaaccgttg | agcagattga | tgagctgcat | gcaaaatatt | gtgatgctct | ctacaatctg | 1020 |
| ttcgaggagt | acaagcatct | tcactccatt | cctcccgaca | ctcatctcat | cttccagtga | 1080 |

<210> SEQ ID NO 69
<211> LENGTH: 1020
<212> TYPE: DNA
<213> ORGANISM: Caenorhabditis elegans

<400> SEQUENCE: 69

| | | | | | |
|---|---|---|---|---|---|
| atgccacatc | tactaggagt | tgagtgggct | ccgctcaata | ttccgttggc | tcggcgtctt | 60 |
| caaactttgg | gagcacttca | tttcttcttc | atcactctct | tcacaccagt | actcgttctc | 120 |
| accgttccat | tctacatgtt | atataccgta | ctctggcctt | tgatctttct | gtatgggctt | 180 |
| tggatgattt | acgattggaa | ttcaccaaag | aagggagcct | atatgagcaa | ttggttccag | 240 |
| agacaaagaa | ttcattcgtg | gtatgccaac | tattttccag | tcaaattgca | cacaacatct | 300 |
| gacatgccag | aagaacataa | ctatttgatt | gggtaccatc | cgcatggaat | aatttcaatg | 360 |

```
gccgcattca tcaactttgc aacaaatgga actggaattc tcgatactct tccacgaatt      420
cgtttccatt tgtgcacact tgttggtcaa ttctggactc cgtggagacg tgagtgggga      480
ttgttgcacg gaatgataga ctgcagtcga gaaagcatca agcacgtttt ggagcatgaa      540
aagaaaggaa aagcagttgt attggtggtt ggtggagctg aagaagcact tgatgcacat      600
ccaggatgcc atattttgac tttgaaaaaa ggaaaggat tcgtgaaaat tgccctgcaa       660
actggagctc aactggttcc atgctattca ttcggtgaaa atgatatttt caatcaagcc      720
gaaaatccaa agggatcaac aattcgacag ttccaaacga taatgaaaag agtcttggga     780
ttctcccctc cagcattcta tgggagagga gtattcaact atacatttgg tcttcttcca     840
ttcaggaaac ctatcaacac tgttctcggc gctccaattt cagtgacaaa gacagtgaat    900
ccaactcaag aacaaatcga cacacttcat cagacataca tggaccgtct tcatgagctt    960
ttcgaggagc acaagacaaa atacgatgtc tctccaacta cacaacttgt tatcaattaa    1020
```

<210> SEQ ID NO 70
<211> LENGTH: 1038
<212> TYPE: DNA
<213> ORGANISM: Caenorhabditis elegans

<400> SEQUENCE: 70

```
atgctaaact accaaattca caaaaagctc accgacatca agtgggtgaa catcttctcc      60
ccatgggatc gccagcgtgc ctacttcgcc ttggtcgtct ggttcgggct catctaccca     120
ttctgctgcc tgtgccaggt ggctccgttt gtgctctttt tcaccggcca gtggattatt     180
ttgggtctct acgcagtttg gtacctttac gatcgagaat ctccgagaag aggaggatat    240
cgggataatt ggttcagaaa tttgtcgctg acaagtggt tcgccgagta ttttcctgtt     300
aaacttcaca aaactgcgga gttggatcca aaccaaaatt atttattcgg atatcatcct    360
catggaattc tcggtgtcgg agcgtggtct tgttttggat ttgatgcgtg caatgtgaag    420
caagtgttca aaggcatccg cttcaacatc tgcaccttgc ccggcaactt caccgcaatg    480
ttccgccgcg agatcctcct cagcatcggt atgatcgaga gctccaaaga atccatcgag    540
cacgtgctca actccgagga aaagggccgt gccgttgtaa ttgtcgtggg tggagccgct    600
gaagctcttg aagctcaccc agggaagcat actctaacac tggcaaatcg caaaggtttc    660
gtgagagaag ccgtgaagac cggagctcat ctggtgccag tttatgcgtt tggagagaat    720
gacatatata agcaaattga acccggaa ggctcgaaat tacggaaaat tcaagaatgg      780
ggaaagaaga aaatgggaat tcactgccca ctaatctacg aagaggata ttttcaaatg     840 gctcttgggc ttcttccaat gagccgagct gtgaatgtag ttgtcggagc gcctattcaa    900
gtggaaaaag agctcgatcc ttctaaggaa gtcattgatg aaattcatgg agtttatatg    960
gaaaagctcg ccgagttatt tgaagagcac aaggcaaagt tcggagtttc caaggacact   1020
cggctcgttt ttcagtga                                                  1038
```

<210> SEQ ID NO 71
<211> LENGTH: 315
<212> TYPE: PRT
<213> ORGANISM: Caenorhabditis elegans
<220> FEATURE:
<221> NAME/KEY: unsure
<222> LOCATION: (1)..(315)
<223> OTHER INFORMATION: unsure at all Xaa locations

<400> SEQUENCE: 71

```
Met Ala Glu Thr His Arg Ala Gly Xaa Ser Ser Pro His Arg Val Ser
1               5                   10                  15

Phe Pro Leu Lys Met Pro Gln Phe Leu Gly Ile Glu Trp Val Asp Leu
                20                  25                  30

Phe Ser Ser Ile Gln Arg Lys Lys Thr Tyr Leu Gly Val Val Tyr His
            35                  40                  45

Phe Met Leu Thr Tyr Pro Leu Ala Leu Phe Val Thr Ile Leu Pro Phe
        50                  55                  60

Phe Leu Leu Phe Thr Phe Gln Trp His Ile Leu Ala Leu Tyr Ala Cys
65                  70                  75                  80

Xaa Val Leu Leu Arg Tyr Gly Phe Ser Glu Xaa Val Asp Ile Pro
                85                  90                  95

Xaa Asp Trp Met Ala Cys Gln Arg Leu Gly Ser Pro Asn Thr Ser Gln
            100                 105                 110

Ser Thr Cys Thr Lys Leu Pro Asn Ser Pro Arg Thr Arg Thr Ile Trp
        115                 120                 125

Leu Glu Ser Ile Xaa His Gly Ile Ile Ser Met Ala Ala Trp Ser Asn
130                 135                 140

Phe Ala Thr Asn Gly Thr Gly Ile Tyr Glu Lys Phe Pro Gly Ile Arg
145                 150                 155                 160

Trp Asn Leu Cys Thr Leu Ala Leu Gln Phe Arg Met Ala Ile Arg Arg
                165                 170                 175

Glu Leu Leu Leu Thr Gly Leu Ile Asp Cys Ser Arg Glu Ser Ile
                180                 185                 190

Glu Tyr Val Leu Asp Lys Cys Gly Gln Lys Gly Arg Ala Val Val Leu
            195                 200                 205

Val Ile Gly Gly Ala Glu Glu Ala Leu Asp Ala His Pro Gly Tyr His
        210                 215                 220

Thr Leu Thr Leu Ala Ser Arg Lys Gly Phe Val Arg Glu Ala Leu Ile
225                 230                 235                 240

Thr Gly Ala Tyr Leu Val Pro Val Tyr Ser Phe Gly Glu Asn Asp Val
                245                 250                 255

Phe Glu Gln Met Glu Asn Pro Val Gly Ser Arg Leu Arg Asn Phe Gln
                260                 265                 270

Glu Trp Cys Lys Ser Ile Phe Gly Ile Ser Tyr Pro Ile Phe His Gly
            275                 280                 285

Arg Gly Phe Phe Gln Leu Thr Phe Gly Tyr Leu Pro Phe Arg Lys Pro
        290                 295                 300

Ile Asp Thr Val Xaa Arg Ser Pro Asn Ser Arg
305                 310                 315
```

<210> SEQ ID NO 72
<211> LENGTH: 1257
<212> TYPE: DNA
<213> ORGANISM: Saccharomyces cerevisiae

<400> SEQUENCE: 72

| | | | | | |
|---|---|---|---|---|---|
| atgtcaggaa | cattcaatga | tataagaaga | aggaagaagg | aagaaggaag | ccctacagcc | 60 |
| ggtattaccg | aaaggcatga | gaataagtct | ttgtcaagca | tcgataaaag | agaacagact | 120 |
| ctcaaaccac | aactagagtc | atgctgtcca | ttggcgaccc | cttttgaaag | aaggttacaa | 180 |
| actctggctg | tagcatggca | cacttcttca | tttgtactct | tctccatatt | tacgttattt | 240 |
| gcaatctcga | caccagcact | gtgggttctt | gctattccat | atatgattta | ttttttttc | 300 |
| gataggtctc | ctgcaactgg | cgaagtggta | aatcgatact | ctcttcgatt | tcgttcattg | 360 |

```
cccatttgga agtggtattg tgattatttc cctataagtt tgattaaaac tgtcaattta      420
aaaccaactt ttacgctttc aaaaaataag agagttaacg aaaaaaatta caagattaga      480
ttgtggccaa ctaagtattc cattaatctc aaaagcaact ctactattga ctatcgcaac      540
caggaatgta cagggccaac gtacttattt ggttaccatc cacacggcat aggagcactt      600
ggtgcgtttg gagcgtttgc aacagaaggt tgtaactatt ccaagatttt cccaggtatt      660
cctatttctc tgatgacact ggtcacacaa tttcatatcc cattgtatag agactactta      720
ttggcgttag gtatttcttc agtatctcgg aaaaacgctt taaggactct aagcaaaaat      780
cagtcgatct gcattgttgt tggtggcgct agggaatctt tattaagttc aacaaatggt      840
acacaactga ttttaaacaa agaaagggt tttattaaac tggccattca acggggaat       900 attaacctag tgcctgtgtt tgcatttgga gaggtggact gttataatgt tctgagcaca      960
aaaaaagatt cagtcctggg taaaatgcaa ctatggttca agaaaacttt tggttttacc     1020
attcccattt tctacgcaag aggattattc aattacgatt tcggtttgtt gccatttaga     1080
gcgcctatca atgttgttgt tggaaggcct atatacgttg aaaagaaaat aacaaatccg     1140
ccagatgatg ttgttaatca tttccatgat ttgtatattg cggagttgaa aagactatat     1200
tacgaaaata gagaaaaata tggggtaccg gatgcagaat tgaagatagt tgggtaa       1257

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: PCR primer
      for SEQ ID NO: 68

<400> SEQUENCE: 73
gcgcggccgc ctgcagtcac tggaagatga g                                     31

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: PCR primer
      for SEQ ID NO: 68

<400> SEQUENCE: 74
gcgcggccgc atgagactcc ggctgagctc g                                     31

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: PCR primer
      for SEQ ID NO: 69

<400> SEQUENCE: 75
gagcggccgc atgccacatc tactaggagt tga                                   33

<210> SEQ ID NO 76
<211> LENGTH: 35
<212> TYPE: DNA
<213> ORGANISM: Artificial Sequence
<220> FEATURE:
<223> OTHER INFORMATION: Description of Artificial Sequence: PCR primer
      for SEQ ID NO: 69
```

```
<400> SEQUENCE: 76
cggcggccgc ctgcagttaa ttgataacaa gttgt                                35

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence: PCR primer
      for SEQ ID NO: 70

<400> SEQUENCE: 77
gcgcggccgc atgctaaact accaaattca ca                                   32

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: PCR primer
      for SEQ ID NO: 70

<400> SEQUENCE: 78
tggcggccgc ctgcagtcac tgaaaaacga gcc                                  33

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: PCR primer
      for SEQ ID NO: 71

<400> SEQUENCE: 79
cagcggccgc atgtcaggaa cattc                                           25

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: PCR primer
      for SEQ ID NO: 71

<400> SEQUENCE: 80
cactgcagtt acccaactat cttcaa                                          26

<210> SEQ ID NO 81
<211> LENGTH: 55
<212> TYPE: DNA
<213> ORGANISM: Artificial Sequence
<220> FEATURE:
<223> OTHER INFORMATION: Description of Artificial Sequence: Cloning
      Adapter

<400> SEQUENCE: 81
cgcgatttaa atggcgcgcc ctgcaggcgg ccgcctgcag ggcgcgccat ttaat          55

<210> SEQ ID NO 82
<211> LENGTH: 32
<212> TYPE: DNA
<213> ORGANISM: Artificial Sequence
<220> FEATURE:
<223> OTHER INFORMATION: Description of Artificial Sequence: Cloning
      Adapter

<400> SEQUENCE: 82
```

```
tcgaggatcc gcggccgcaa gcttcctgca gg                                    32

<210> SEQ ID NO 83
<211> LENGTH: 32
<212> TYPE: DNA
<213> ORGANISM: Artificial Sequence
<220> FEATURE:
<223> OTHER INFORMATION: Description of Artificial Sequence: Cloning
      Adapter

<400> SEQUENCE: 83
tcgacctgca ggaagcttgc ggccgcggat cc                                    32

<210> SEQ ID NO 84
<211> LENGTH: 1068
<212> TYPE: DNA
<213> ORGANISM: Artificial Sequence
<220> FEATURE:
<223> OTHER INFORMATION: Description of Artificial Sequence: Re-
      synthesized MR1 nucleic acid sequence

<400> SEQUENCE: 84
atggctagca aggaccagca cctccaacag aaggtgaagc acaccttga ggccatccca       60 tcccctaggt atgctccact cagggtccca cttaggagaa ggctccaaac ccttgctgtt     120
ctcctctggt gctccatgat gagcatctgc atgttcatct tcttcttcct ctgcagcatc     180
cctgtgctcc tttggttccc aattatcctc tacttgacct ggattttggt gtgggataag     240
gcccctgaga acggaggcag acctatcagg tggctcagga acgcagcttg gtggaagctc     300
tttgctggat acttcccagc tcatgttatc aaggaggctg accttgaccc atccaagaac     360
tacatctttg gttaccaccc acatggtatc atcagcatgg gtagcttctg caccttctcc     420
accaacgcta ctggtttcga tgacctcttc ccaggaatca ggccttcctt gctcaccctc     480
accagcaact tcaacatccc actctacagg gattacctca tggcctgtgg actctgctca     540
gtgtctaaga cctcctgcca gaacatcctc accaagggtg gtccaggaag gtccattgct     600
attgtggtgg gaggtgcctc tgagtccttg aacgccagac caggagtgat ggaccttgtg     660
ttgaagagga ggtttggatt catcaagatt gctgtgcaga ctggtgctag ccttgtccct     720
accatctcct ttggtgagaa tgagctttat gagcagattg agagcaatga gaactctaag     780
cttcacaggt ggcagaagaa gatccagcat gctcttggtt tcaccatgcc actcttccat     840 ggaagggtg tgttcaacta cgactttggt ctcctcccac acaggcaccc aatttacacc     900
attgtgggta agccaatccc agtcccatct atcaagtacg gtcagaccaa ggatgagatc     960
atcagggagc tccatgactc ttacatgcac gctgtgcagg acctctatga caggtacaag    1020
gacatctacg ccaaggacag ggtcaaggag cttgagtttg tggagtga                 1068
```